US010907762B2

(12) United States Patent
Kitahara

(10) Patent No.: US 10,907,762 B2
(45) Date of Patent: Feb. 2, 2021

(54) PHYSICAL QUANTITY MEASUREMENT DEVICE

(71) Applicant: DENSO CORPORATION, Kariya (JP)

(72) Inventor: Noboru Kitahara, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 16/594,414

(22) Filed: Oct. 7, 2019

(65) Prior Publication Data

US 2020/0032946 A1  Jan. 30, 2020

Related U.S. Application Data

(63) Continuation of application No. PCT/JP2018/010141, filed on Mar. 15, 2018.

(30) Foreign Application Priority Data

Apr. 13, 2017 (JP) ................................ 2017-079880

(51) Int. Cl.

| | |
|---|---|
| *G05F 5/00* | (2006.01) |
| *G01F 1/68* | (2006.01) |
| *F16L 55/179* | (2006.01) |
| *A61M 39/22* | (2006.01) |
| *B01F 5/06* | (2006.01) |
| *B01F 15/02* | (2006.01) |
| *B01J 19/00* | (2006.01) |

(Continued)

(52) U.S. Cl.
CPC ......... *F16L 55/179* (2013.01); *A61M 39/223* (2013.01); *B01F 5/0601* (2013.01); *B01F 15/0264* (2013.01); *B01J 19/0093* (2013.01); *F16L 55/265* (2013.01); *G01F 1/00* (2013.01); *G01F 1/684* (2013.01); *G01F 5/005* (2013.01)

(58) Field of Classification Search
None
See application file for complete search history.

(56) References Cited

U.S. PATENT DOCUMENTS

2020/0033172 A1* 1/2020 Mashita ................ G01F 1/6842

FOREIGN PATENT DOCUMENTS

| JP | 2016-31341 | 3/2016 |
|---|---|---|
| WO | 2018/190066 | 10/2018 |

(Continued)

OTHER PUBLICATIONS

U.S. Appl. No. 16/594,403 of Kitahara, filed Oct. 7, 2019 (118 pages).

(Continued)

*Primary Examiner* — Harshad R Patel
(74) *Attorney, Agent, or Firm* — Nixon & Vanderhye P.C.

(57) ABSTRACT

A physical quantity measurement device includes a passage flow channel, a branch flow channel, and a physical quantity detection unit. An inflow region extending from the inflow port and a lateral region laterally arranged to the inflow region are included in at least one of the passage flow channel and the branch flow channel. The physical quantity detection unit is disposed in the lateral region. A guiding surface that guides away from the lateral region in the lateral direction foreign matter is included in at least one of an inner peripheral surface of the passage flow channel and an inner peripheral surface of the branch flow channel at a position upstream of the lateral region.

10 Claims, 40 Drawing Sheets

(51) Int. Cl.
*F16L 55/26* (2006.01)
*G01F 1/684* (2006.01)
*G01F 5/00* (2006.01)
*G01F 1/00* (2006.01)

(56) References Cited

FOREIGN PATENT DOCUMENTS

| | | |
|---|---|---|
| WO | 2018/190067 | 10/2018 |
| WO | 2018/190068 | 10/2018 |

OTHER PUBLICATIONS

U.S. Appl. No. 16/594,382 of Kitahara, filed Oct. 7, 2019 (117 pages).
U.S. Appl. No. 16/594,368 of Kitahara, filed Oct. 7, 2019 (118 pages).

* cited by examiner

PHYSICAL QUANTITY MEASUREMENT DEVICE

CROSS REFERENCE TO RELATED APPLICATIONS

This application is a continuation application of international Patent Application No. PCT/JP2018/010141 filed on Mar. 15, 2018, which designated the U.S. and claims the benefit of priority from Japanese Patent Application No. 2017-079880 filed on Apr. 13, 2017. The entire disclosure of all of the above applications are incorporated herein by reference.

TECHNICAL FIELD

The present disclosure relates to a physical quantity measurement device.

BACKGROUND ART

As a physical quantity measurement device for measuring a physical quantity of a fluid, for example, a physical quantity measurement device for measuring a flow rate of an intake air taken into an internal combustion engine is known. The physical quantity measurement device has a discharge passage for discharging the inflow fluid, and a branch passage branched from the discharge passage, and a flow rate detection unit is provided in the branch passage. While the branch passage is curved to make one turn, the discharge passage is not greatly curved. In this example, a foreign matter having a relatively large mass of the foreign matter flowing into the discharge passage together with the fluid tends to move linearly as compared with the fluid. For that reason, the foreign matter having the relatively large mass tends to be discharged from an outflow port of the discharge passage without entering the branch passage. As a result, the detection accuracy of the flow rate detection unit is inhibited from being lowered by the presence of the foreign matter.

SUMMARY

A first aspect of the present disclosure is a physical quantity measurement device that measures a physical quantity of a fluid. The device includes a passage flow channel that has an inflow port and an outflow port, the fluid entering the passage flow channel through the inflow port and exiting the passage flow channel through the outflow port, a branch flow channel that branches off from the passage flow channel, the branch flow channel discharging the fluid having flowed into the branch flow channel from the passage flow channel through a branch outflow port, and a physical quantity detector that detects a physical quantity of the fluid in the branch flow channel, wherein, an imaginary line connecting a center of the inflow port and a center of the branch outflow port and including at least a part of a center line of the passage flow channel and a center line of the branch flow channel is defined as a flow channel center line, a boundary between the passage flow channel and the branch flow channel is defined as a flow channel boundary portion, a pair of opposing passage surfaces in an inner peripheral surface of the passage flow channel face each other across the flow channel boundary portion and the inflow port, a direction along which the pair of opposing passage surfaces are arranged is defined as a lateral direction, a direction along which the flow channel center line extends is defined as a flow channel direction, a direction orthogonal to both the lateral direction and the flow channel direction is defined as a vertical direction, an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, and a guiding surface that guides away from the lateral region in the lateral direction foreign matter entering through the inflow port together with the fluid is included in at least one of the inner peripheral surface of the passage flow channel and an inner peripheral surface of the branch flow channel at a position upstream of the lateral region.

A second aspect of the present disclosure is a physical quantity measurement device that measures a physical quantity of fluid. The device includes a passage flow channel that has an inflow port and an outflow port, the fluid entering the passage flow channel through the inflow port and exiting the passage flow channel through the outflow port, a branch flow channel that branches off from the passage flow channel, the branch flow channel discharging the fluid having flowed in the branch flow channel from the passage flow channel through a branch outflow port, and a physical quantity detector that detects a physical quantity of the fluid in the branch flow channel, wherein an imaginary line connecting a center of the inflow port and a center of the branch outflow port and including at least a part of a center line of the passage flow channel and a center line of the branch flow channel is defined as a flow channel center line, a boundary between the passage flow channel and the branch flow channel is defined as a flow channel boundary portion, a pair of opposing surfaces in an inner peripheral surface of the passage flow channel face each other across the flow channel boundary portion and the inflow port, a direction along which the pair of opposing surfaces are arranged is defined as a lateral direction, a direction along which the flow channel center line extends is defined as a flow channel direction, and a direction orthogonal to both the lateral direction and the flow channel direction is defined as a vertical direction, an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, a cover portion that covers the physical quantity detector from an upstream side of the detector is disposed in the branch flow channel, the lateral region is disposed at a position downstream of the cover portion in the flow channel direction, and a guiding surface that guides toward the cover portion in the lateral direction foreign matter entering through the inflow port together with the fluid is included in at least one of the inner peripheral surface of the passage flow channel and an inner peripheral surface of the branch flow channel at a position upstream of the lateral region.

A third aspect of the present disclosure is a physical quantity measurement device that measures a physical quantity of fluid. The device includes a passage flow channel that has an inflow port and an outflow port, the fluid entering the passage flow channel through the inflow port and exiting the passage flow channel through the outflow port, a branch flow channel that branches off from the passage flow channel, the branch flow channel discharging the fluid having flowed in the branch flow channel through a branch outflow port, and a physical quantity detector that detects a physical quantity of the fluid in the branch flow channel, wherein an imaginary line connecting a center of the inflow port and a center of the branch outflow port and including at least a part of a center line of the passage flow channel and a center line of the branch flow channel is defined as a flow channel center line, and a boundary between the passage flow channel and the branch flow channel is a flow channel boundary portion, a pair of opposing surfaces in an inner peripheral surface of the passage flow channel face each other across the flow channel boundary portion and the inflow port, a direction along which the pair of opposing surfaces are arranged is defined as a lateral direction, a direction along which the flow channel center line extends is defined as a flow channel direction, a direction orthogonal to both the lateral direction and the flow channel direction is defined as a vertical direction, an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, and a guiding surface that guides away from the lateral region in the lateral direction foreign matter entering through the inflow port together with the fluid is included in the inner peripheral surface of the passage flow channel at a position upstream of the flow channel boundary portion in the passage flow channel.

BRIEF DESCRIPTION OF DRAWINGS

The above and other objects, features and advantages of the present disclosure will become more apparent from the following detailed description made with reference to the accompanying drawings.

The above and other objects, features and advantages of the present disclosure will become more apparent from the following detailed description made with reference to the accompanying drawings. In the drawings.

DESCRIPTION OF EMBODIMENTS

Figure 1:
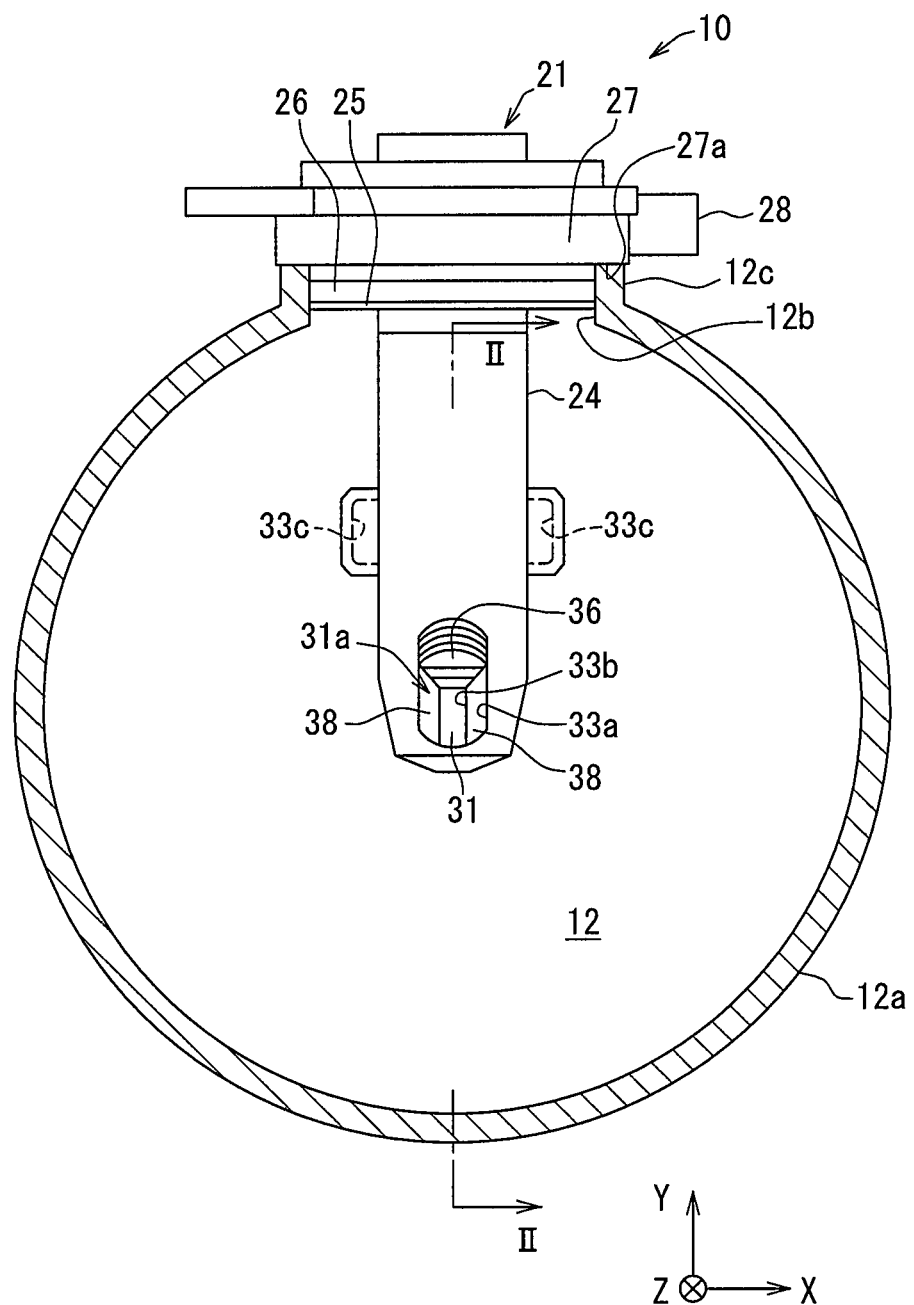
FIG. 1 is a front view of an air flow meter in a state of being attached to an intake pipe as viewed from an upstream side according to a first embodiment.

Hereinafter, a plurality of embodiments of the present disclosure will be described with reference to the drawings. Incidentally, the same reference numerals are assigned to the corresponding components in each embodiment, and thus, duplicate descriptions may be omitted. When only a part of the configuration is described in each embodiment, the configuration of the other embodiments described above can be applied to the other parts of the configuration. Further, not only the combinations of the configurations explicitly shown in the description of the respective embodiments, but also the configurations of the plurality of embodiments can be partially combined with each other even if the combinations are not explicitly shown if there is no problem in the combination in particular. Unspecified combinations of the configurations described in the plurality of embodiments and the modification examples are also disclosed in the following description.

In a conventional physical quantity measurement device as described above, even if the foreign matter easily travels linearly, the foreign matter does not necessarily enter the branch passage, and there is room for an improvement in the configuration in which the foreign matter does not enter the branch passage. In other words, there is room for an improvement in the configuration for reducing an arrival of the foreign matter to the physical quantity detector such as the flow rate detection unit.

First Embodiment

Figure 2:
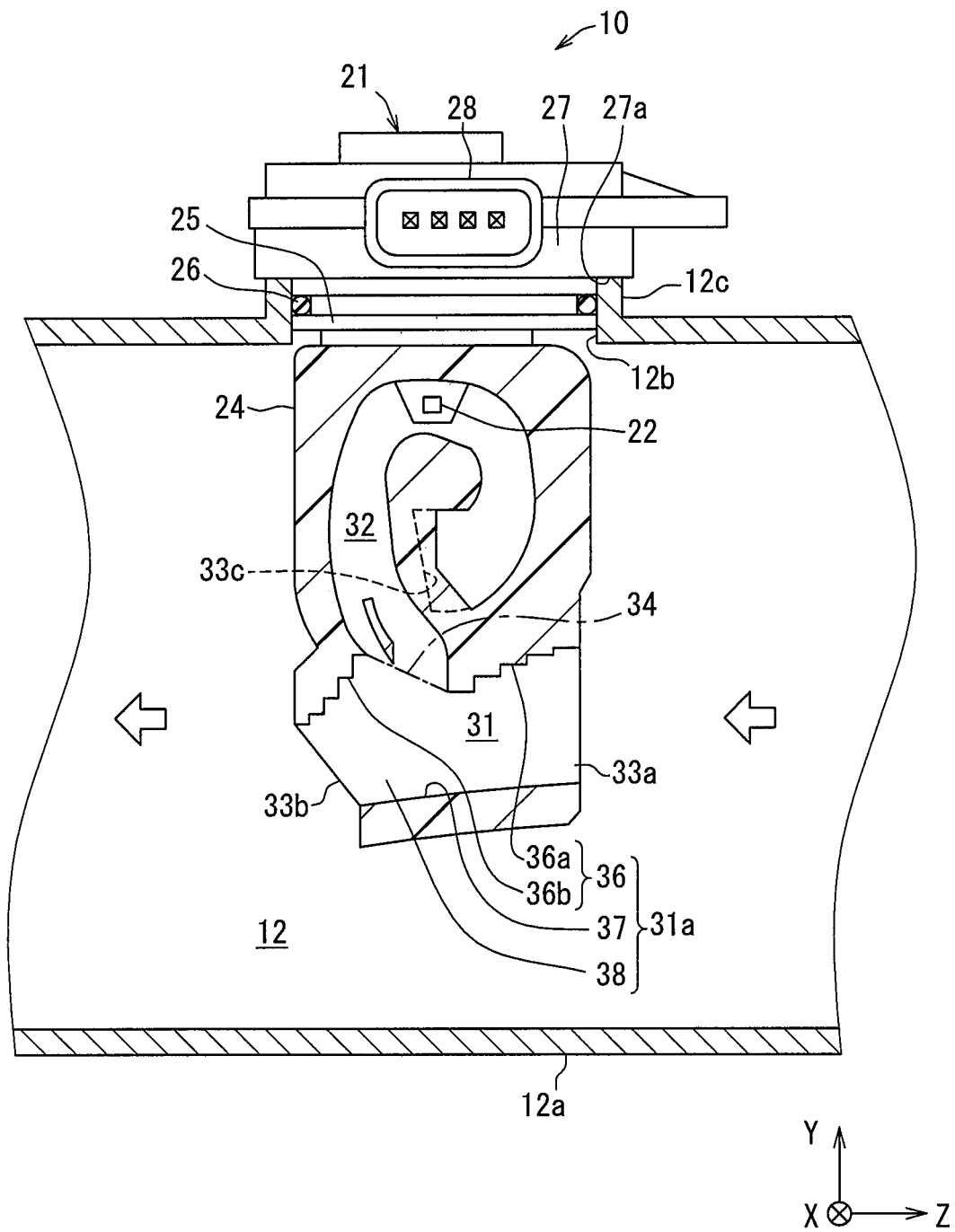
FIG. 2 is a cross-sectional view taken along a line II-II of FIG. 1.

An air flow meter 10 shown in FIGS. 1 and 2 is a physical quantity measurement device that measures a physical quantity such as a flow rate, a temperature, a humidity, and a pressure with respect to a fluid such as air. The air flow meter 10 is mounted on a vehicle having an internal combustion engine 11 such as an engine. The internal combustion engine 11 has an intake passage 12 and an exhaust passage, and the air flow meter 10 is attached to the intake passage 12. In that case, the fluid to be measured by the air flow meter 10 is an intake air flowing through the intake passage 12. The intake air is a gas to be supplied to a combustion chamber of the internal combustion engine 11. The air flow meter 10 is disposed on a downstream side of an air cleaner in the intake passage 12. In that case, in the intake passage 12, the air cleaner is at the upstream side and the combustion chamber is at the downstream side relative to the air flow meter 10.

The air flow meter 10 is detachably attached to an intake pipe 12a defining the intake passage 12. The air flow meter 10 is inserted into a sensor insertion hole 12b provided to penetrate through a cylindrical wall of the intake pipe 12a, and is at least partially positioned in the intake passage 12. The intake pipe 12a has a flange portion 12c extending from the sensor insertion hole 12b toward an outer peripheral side. The flange portion 12c extends along a peripheral portion of the sensor insertion hole 12b, and is, for example, ring-shaped. A tip end face of the flange portion 12c extends in a direction orthogonal to a center line of the flange portion 12c. In that case, the tip end face of the flange portion 12c extends in a longitudinal direction of the intake passage 12, that is, in a direction in which an intake air flows in the intake passage 12.

The air flow meter 10 includes a housing 21 and a flow rate detection unit 22.

The housing 21 is made of, for example, a resin material or the like. In the air flow meter 10, since the housing 21 is attached to the intake pipe 12a, the flow rate detection unit 22 is brought into a state in which the flow rate detection unit 22 can come into contact with the intake air flowing through the intake passage 12. The housing 21 has a flow channel forming portion 24, a fitting portion 25, an O-ring 26, a flange portion 27, and a connector portion 28.

The flow channel forming portion 24 defines flow channels 31 and 32. The flow channels 31 and 32 are provided by an internal space of the flow channel forming portion 24, and introduce a part of the intake air flowing through the intake passage 12 into the housing 21. The passage flow channel 31 penetrates through the flow channel forming portion 24, and an upstream end portion of the passage flow channel 31 is referred to as an inflow port 33a, and a downstream-side end portion of the passage flow channel 31 is referred to as an outflow port 33b. The measurement flow channel 32 is a branch flow channel that branches off from an intermediate portion of the passage flow channel 31, and has a curved portion to circulate around the inside of the flow channel forming portion 24. However, the measurement flow channel 32 does not make one turn, and a portion close to the upstream end portion and a portion close to the downstream end portion of the measurement flow channel 32 do not overlap with each other in the width direction of the flow channel forming portion 24. Also, the passage flow channel 31 and the measurement flow channel 32 do not overlap with each other in the width direction of the flow channel forming portion 24.

The downstream end portion of the measurement flow channel 32 is opened similarly to the downstream-side end portion of the passage flow channel 31, and the downstream-side end portion is referred to as a measurement outlet 33c. The measurement flow channel 32 branches toward the downstream end portion, and thus has two measurement outlets 33c, and those measurement outlets 33c are disposed laterally at positions spaced apart from each other in the width direction of the flow channel forming portion 24. As described above, because the passage flow channel 31 and the measurement flow channel 32 do not overlap with each other in the width direction of the flow channel forming portion 24, each of the measurement outlets 33c and the outflow port 33b do not overlap with each other in the width direction of the flow channel forming portion 24. The intake passage 12 may be referred to as a main passage, and the passage flow channel 31 and the measurement flow channel 32 may be collectively referred to as a secondary passage. The measurement outlet 33c corresponds to a branch outlet.

The fitting portion 25 is a portion that is fitted into the sensor insertion hole 12b through the O-ring 26. The O-ring 26 is a member for sealing the intake passage 12 and the outside of the intake pipe 12a. The O-ring 26 is externally fitted to the fitting portion 25, and is interposed between the fitting portion 25 and the sensor insertion hole 12b in a state of entering the inner peripheral side of the flange portion 12c. The flange portion 27 is disposed on a side opposite to the flow channel forming portion 24 across the fitting portion 25, and covers the sensor insertion hole 12b from an outer peripheral side of the intake pipe 12a. The flange portion 27 is caught by the tip portion of the flange portion 12c of the intake pipe 12a to restrict the housing 21 from excessively entering the intake passage 12. The flange portion 27 has a flange surface 27a which faces the flow channel forming portion 24. The flange surface 27a extends in parallel with the tip end face of the flange portion 12c, and is put on the tip end face of the flange portion 12c.

The connector portion 28 surrounds multiple terminals. A plug portion is inserted into the connector portion 28. The plug portion is provided at an end portion of a connecting line electrically connected directly or indirectly to an engine control device such as an ECU, and mates with the connector portion 28.

The flow rate detection unit 22 is a thermal type flow rate sensor using, for example, a heat generation unit such as a heat generating resistive element or a heater unit and a detection surface of the flow rate detection unit 22 is formed of a membrane.

The flow rate detection unit 22 is disposed at an intermediate position of the measurement flow channel 32. When the housing 21 is attached to the intake pipe 12a, the intake air flowing through the measurement flow channel 32 is supplied to the flow rate detection unit 22. The flow rate detection unit 22 is electrically connected to the multiple terminals provided in the connector portion 28. The flow rate detection unit 22 outputs a sensor signal corresponding to the intake flow rate and corresponding to a flow rate of the air flowing through the measurement flow channel 32 to the engine control device as a flow rate signal. The flow rate detection unit 22 detects the flow rate of the intake air flowing in the intake passage 12 by detecting the flow rate of the intake air flowing in the measurement flow channel 32. The flow rate detection unit 22 corresponds to a "physical quantity detector" that detects the flow rate of the intake air as a physical quantity. Further, the flow rate detection unit 22 is not limited to the thermal type flow rate sensor, and may be a movable flap type flow rate sensor, a Kalman vortex type flow rate sensor, or the like.

The air flow meter 10 has a temperature detection unit for detecting a temperature and a humidity detection unit for detecting a humidity in addition to the flow rate detection unit 22. The temperature detection unit and the humidity detection unit are provided on an outer peripheral side of the housing 21, and output sensor signals corresponding to the temperature and humidity of the intake air flowing through the intake passage 12 as a temperature signal and a humidity signal. For example, the air flow meter 10 has a support for supporting those detection units on the outer peripheral side of the housing 21, and the support is fixed to the housing 21.

In the air flow meter 10, a direction in which the two measurement outlets 33c are aligned is referred to as a width direction X, a direction in which the flow channel forming portion 24 and the flange portion 27 are aligned is referred to as a height direction Y, and a direction in which the passage flow channel 31 extends is referred to as a depth direction Z. The width direction X, the height direction Y, and the depth direction Z are orthogonal to each other, and the flange surface 27a of the flange portion 27 extends in parallel to both the width direction X and the depth direction Z. In a state in which the air flow meter 10 is attached to the intake pipe 12a, the inflow port 33a faces the upstream side of the intake passage 12, and the outflow port 33b and the measurement outlet 33c face the downstream side. In that case, it is considered that the direction in which the intake air flows in the intake passage 12 is the depth direction Z, and the inflow direction of the inflow air from the inflow port 33a is likely to be the same as the depth direction Z. In the air flow meter 10, the intake air flowing in from the inflow port 33a passes through the passage flow channel 31 and the measurement flow channel 32, and flows out from the outflow port 33b and each measurement outlet 33c.

In a flow channel boundary portion 34, which is a boundary between the passage flow channel 31 and the measurement flow channel 32, an intermediate portion of the passage flow channel 31 is opened toward the flange portion 27 in the height direction Y. In the flow channel boundary portion 34, the intermediate portion of the passage flow channel 31 and the upstream end portion of the measurement flow channel 32 are connected to each other, and the upstream end portion of the measurement flow channel 32 can also be referred to as a measurement inlet. The measurement flow channel 32 has a portion extending in the depth direction Z between the flow channel boundary portion 34 and the measurement outlet 33c, and the flow rate detection unit 22 is disposed in that portion.

In the air flow meter 10, it is assumed that dust such as sand and dust enters from the inflow port 33a as foreign matter together with intake air. In that case, it is considered that most of the foreign matter travels in the depth direction Z along a flow of the intake air to exit from the outflow port 33b, but some of the foreign matter enters the measurement flow channel 32 together with some of the intake air. In particular, it is considered that a large foreign matter such as a foreign matter having a relatively large mass or a foreign matter having a relatively large size tends to move linearly regardless of the flow direction of the intake air. For that reason, there is a concern that the large foreign matter collides with an inner peripheral surface 31a of the passage flow channel 31 and rebounds, and when a traveling direction of the large foreign matter changes, the large foreign matter more easily enters the measurement flow channel 32.

On the other hand, in the present embodiment, the large foreign matter that has rebounded on the inner peripheral surface 31a of the passage flow channel 31 is inhibited from entering the measurement flow channel 32. It is considered that a small foreign matter, such as a foreign matter having a relatively small mass or a foreign matter having a relatively small size, tends to change the traveling direction of the small foreign matter in accordance with the flow of intake air, and tends to bend before colliding with the inner peripheral surface 31a of the passage flow channel 31.

Figure 3:
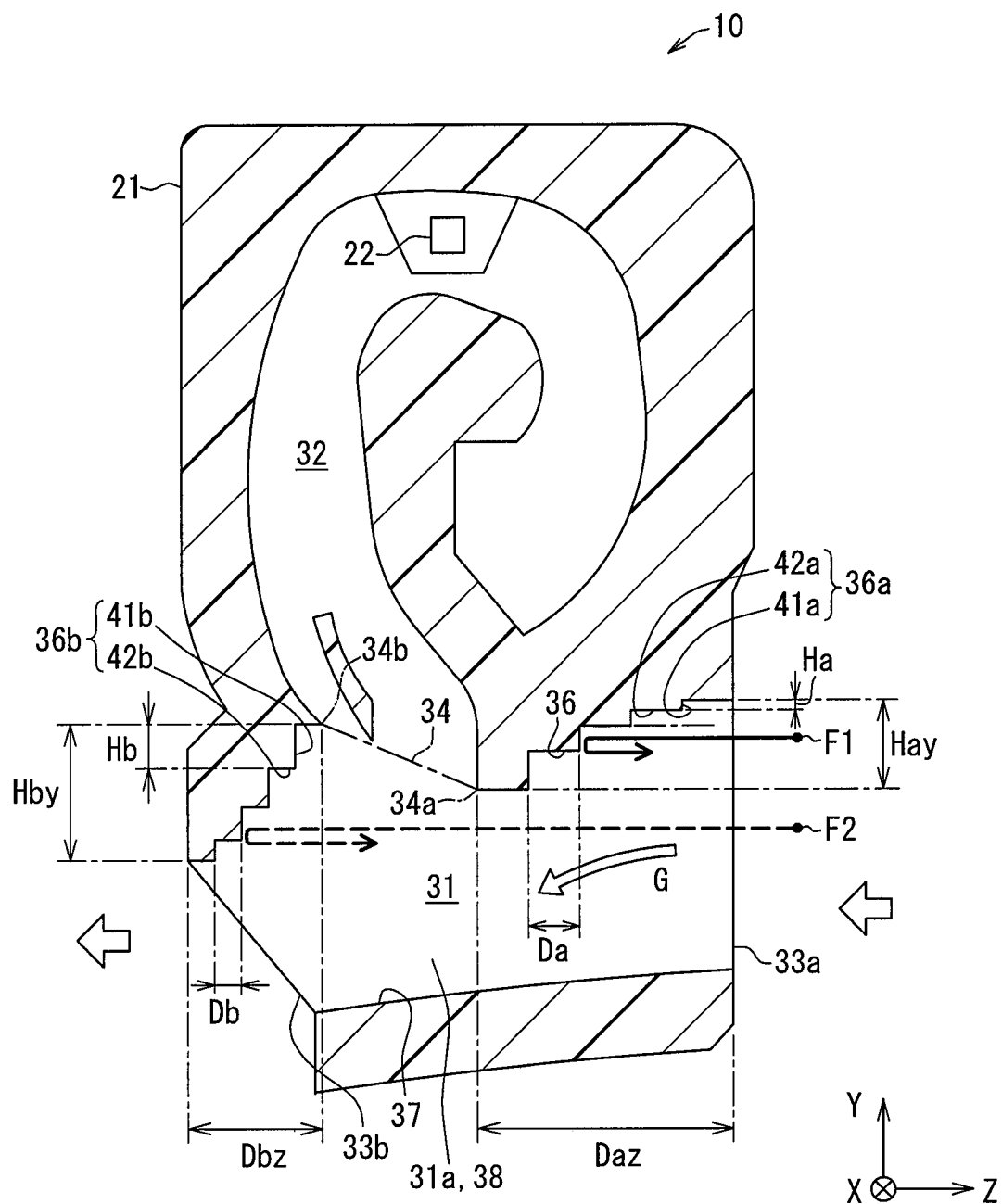
FIG. 3 is a diagram a periphery of a passage flow channel in FIG. 2.

As shown in FIGS. 1 and 3, the inner peripheral surface 31a of the passage flow channel 31 has a ceiling surface 36, a bottom surface 37, and a pair of wall surfaces 38. The pair of wall surfaces 38 are a pair of facing surfaces facing each other across the flow channel boundary portion 34, the inflow port 33a, and the outflow port 33b in the width direction X, and the ceiling surface 36 and the bottom surface 37 are a pair of facing surfaces facing each other across the wall surfaces 38. In the passage flow channel 31, a portion of the ceiling surface 36 is opened, and an upstream end portion of the measurement flow channel 32 is connected to the opened portion, thereby providing the flow channel boundary portion 34. The ceiling surface 36 has an inflow ceiling surface portion 36a between the inflow port 33a and the flow channel boundary portion 34, and an outflow ceiling surface portion 36b between the flow channel boundary portion 34 and the outflow port 33b.

In this example, the flow channel boundary portion 34 has an upstream boundary portion 34a located at the most upstream side and a downstream boundary portion 34b located at the most downstream side, and in the height direction Y, the upstream boundary portion 34a is located at a position spaced apart from the flange portion 27 from the downstream boundary portion 34b. In that case, the upstream end portion of the measurement flow channel 32 is opened not toward the inflow port 33a but toward the outflow port 33b. For that reason, even if the foreign matter traveling linearly in the depth direction Z enters from the inflow port 33a, the foreign matter does not easily enter the measurement flow channel 32 as it is. In the above configuration, for example, even if a person looks into the passage flow channel 31 from the inflow port 33a in the depth direction Z, an upstream end portion of the measurement flow channel 32 cannot be visualized.

In the ceiling surface 36, since the inflow ceiling surface portion 36a and the outflow ceiling surface portion 36b have step surfaces 41a and 41b and connection surfaces 42a and 42b, respectively, a step facing the inflow port 33a is defined. In the inflow ceiling surface portion 36a, the multiple inflow step surfaces 41a are disposed at depth intervals Da along the aligned direction of the inflow port 33a and the flow channel boundary portion 34. In the outflow ceiling surface portion 36b, the multiple outflow step surfaces 41b are aligned at depth intervals Db along the alignment direction of the flow channel boundary portion 34 and the outflow port 33b, and the depth interval Db is smaller than a depth interval Da. The step surfaces 41a and 41b extend toward the bottom surface 37 on the ceiling surface 36, and thus face the inflow port 33a, and extend over the pair of wall surfaces 38. Each inflow step surface 41a and each outflow step surface 41b extend in the same direction, specifically, both extend in a direction orthogonal to the depth direction Z.

The inflow connection surfaces 42a connect the downstream-side end portion of the upstream side inflow step surface 41a and the upstream end portion of the downstream side inflow step surface 41a in the adjacent inflow step surfaces 41a at the inflow ceiling surface portion 36a, and the multiple inflow connection surfaces 42a are provided according to the number of the inflow step surface 41a. The outflow connection surfaces 42b connect the downstream-side end portion of the upstream side outflow step surface 41b and the upstream end portion of the downstream side outflow step surface 41b in the adjacent outflow step surfaces 41b at the outflow ceiling surface portion 36b, and the multiple outflow connection surfaces 42b are provided according to the number of the outflow step surface 41b. The connection surfaces 42a and 42b extend in the same direction, specifically, in a direction orthogonal to the height direction Y. In other words, each inflow connection surface 42a is orthogonal to the inflow step surface 41a, and each outflow connection surface 42b is orthogonal to the outflow step surface 41b. In that case, in the depth direction Z, the depth dimensions of the connection surfaces 42a and 42b are the same as the depth intervals Da and Db of the adjacent step surfaces 41a and 41b.

The inflow ceiling surface portion 36a and the outflow ceiling surface portion 36b are formed in a staircase shape as a whole by the step surfaces 41a and 41b and the connection surfaces 42a and 42a. In the inflow ceiling surface portion 36a, the step gradually increases toward the downstream side. Specifically, while the depth interval Da is uniform in each step, a height dimension Ha of the inflow step surface 41a along the height direction Y gradually increases as a distance from the inflow port 33a increases. In the step close to the inflow port 33a, the height dimension Ha is smaller than the depth interval Da, but a difference between the height dimension Ha and the depth interval Da gradually decreases as the step comes closer to the flow channel boundary portion 34, and in the step close to the flow channel boundary portion 34, the height dimension Ha and the depth interval Da have substantially the same value. A height dimension Ha may be smaller than the depth interval Da.

On the other hand, in the outflow ceiling surface portion 36b, the step becomes gradually smaller toward the downstream side. Specifically, while the depth interval Db is uniform in each step, a height dimension Hb of the outflow step surface 41b in the height direction Y gradually decreases as the step comes closer to the outflow port 33b. In the step close to the flow channel boundary portion 34, the height dimension Hb is larger than the depth interval Db, but the difference between the height dimension Hb and the depth interval Db gradually decreases as the step comes closer to the flow outflow port 33b, and in the step closer to the flow outflow port 33b, the height dimension Hb is larger than the depth interval Db.

In the ceiling surface 36, the overall inclination angle of the outflow ceiling surface portion 36b with respect to the depth direction Z is larger than the overall inclination angle of the inflow ceiling surface portion 36a with respect to the depth direction Z. In this example, in a positional relationship between the upstream end portion and the downstream end portion of the inflow ceiling surface portion 36a, a separation distance in the height direction Y is referred to as a height distance Hay, and a separation distance in the depth direction Z is referred to as a depth distance Daz. In a positional relationship between the upstream end portion and the downstream end portion of the inflow ceiling surface portion 36a, a separation distance in the height direction Y is referred to as a height distance Hby, and a separation distance in the depth direction Z is referred to as a depth distance Daz. In that instance, a value of Hby/Dbz indicating the degree of inclination of the outflow ceiling surface portion 36b is larger than a value of Hay/Daz indicating the degree of inclination of the inflow ceiling surface portion 36a. As a result, the intake air easily flows in from the inflow port 33a, and a flow rate of the intake air in the measurement flow channel 32 easily increases.

The inflow ceiling surface portion 36a is curved so that an intermediate portion in the width direction X swells toward the flange portion 27 in accordance with the shape of the inflow port 33a. In that case, both the upstream end portion and the downstream-side end portion of the inflow step surface 41a are curved. The inflow connection surfaces 42a are curved so as to connect the adjacent inflow step surfaces 41a to each other. On the other hand, the outflow port 33b has a substantially rectangular shape, and the outflow ceiling surface portion 36b is not curved.

According to the present embodiment described so far, since the inflow ceiling surface portion 36a has the inflow step surfaces 41a, a foreign matter that has entered from the inflow port 33a hardly enters the measurement flow channel 32. For example, as indicated by a solid line in FIG. 3, when a large foreign matter F1 entering from the inflow port 33a travels linearly in the depth direction Z and collides with the inflow step surface 41a of the inflow ceiling surface portion 36a, there is a high possibility that the large foreign matter F1 returns back to the inflow port 33a so as to follow its own trajectory. As described above, the large foreign matter F1 does not easily advance to the downstream side by colliding with the inflow step surface 41a of the inflow ceiling surface portion 36a in the passage flow channel 31, and does not easily enter the measurement flow channel 32.

Figure 4:
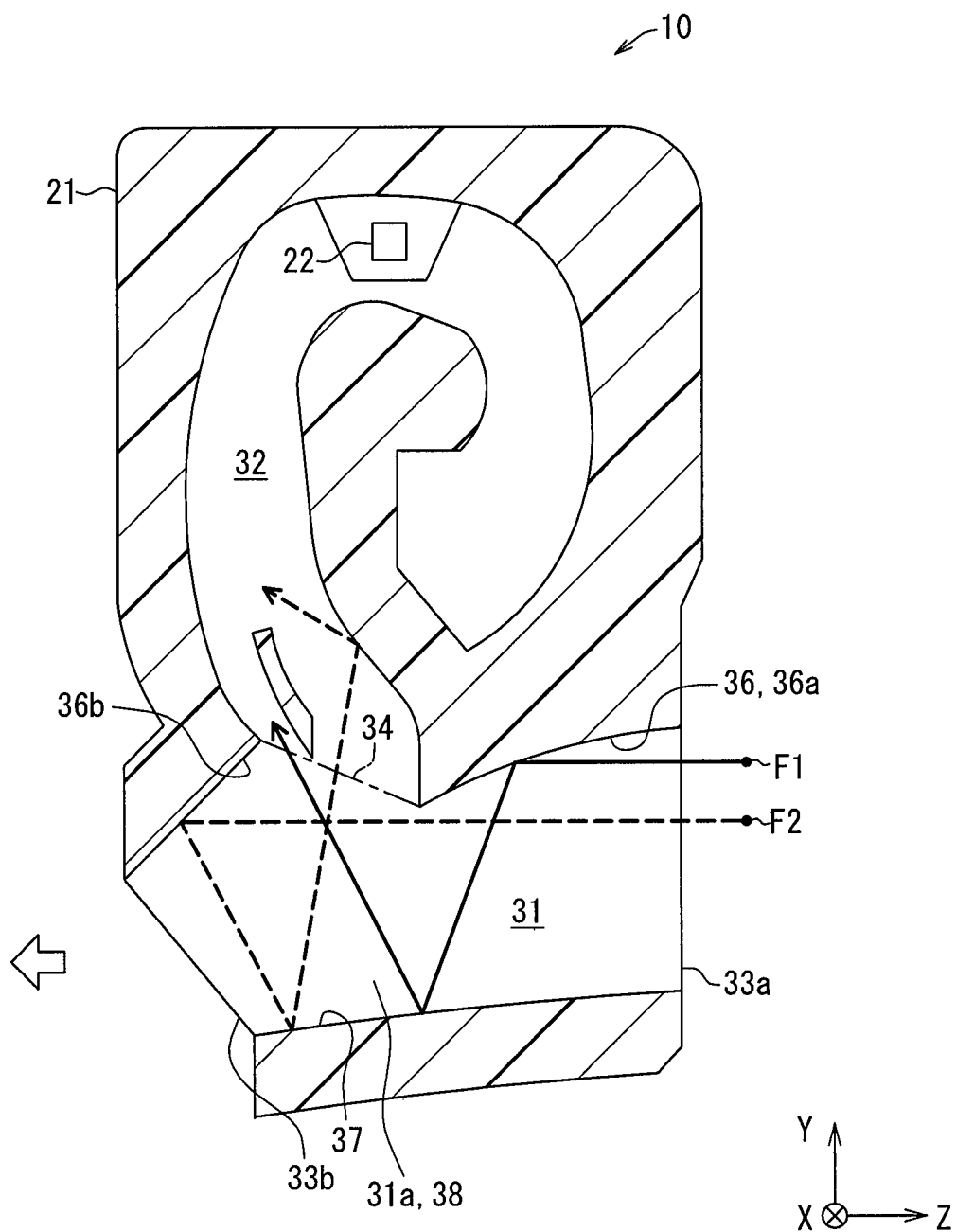
FIG. 4 is a diagram illustrating a configuration in which a ceiling surface of the passage flow channel does not have a step surface, unlike the first embodiment.

On the other hand, unlike the present embodiment, for example, in a configuration in which the inflow ceiling surface portion 36a does not have the inflow step surface 41a as shown in FIG. 4, the inflow ceiling surface portion 36a is not orthogonal to the depth direction Z. For that reason, it is conceivable that the large foreign matter F1 collides with the inflow ceiling surface portion 36a which is inclined as a whole, and advances to the downstream side while changing the traveling direction. In that case, there is a concern that the large foreign matter F1 can easily enter the measurement flow channel 32 by advancing downstream while the large foreign matter F1 rebounds at the bottom surface 37 following the inflow ceiling surface portion 36a, as indicated by a solid line in FIG. 4, depending on an angle at which the large foreign matter F1 rebounds at the inflow ceiling portion 36a. As described above, when the traveling direction of the large foreign matter F1 changes in the height direction Y with the rebound at the inflow ceiling surface portion 36a, the possibility that the large foreign matter F1 flows into the measurement flow channel 32 is likely to increase. In that regard, according to the present embodiment, since a configuration is realized in which the traveling direction of the large foreign matter F1 rebounded at the inflow step surface 41a of the inflow ceiling surface portion 36a does not easily change in the height direction Y, the large foreign matter F1 can be inhibited from easily entering the measurement flow channel 32.

In the air flow meter 10 in which the flow rate detection unit 22 is provided in the measurement flow channel 32, if the flow rate of the intake air flowing through the measurement flow channel 32 is too small, there is a concern that the detection accuracy of the flow rate detection unit 22 is lowered. On the other hand, according to the present embodiment, since the multiple inflow step surfaces 41a are aligned in the depth direction Z, the cross-sectional area of the passage flow channel 31 can be gradually reduced toward the flow channel boundary portion 34 while increasing the open area of the inflow port 33a as much as possible. For that reason, the inflow of the intake air into the measurement flow channel 32 can be inhibited from being insufficient while inhibiting the inflow of the large foreign matter into the measurement flow channel 32 by the inflow step surface 41a.

According to the present embodiment, since the multiple inflow step surfaces 41a are included in the inflow ceiling surface portion 36a, the inflow ceiling surface portion 36a can be gradually spaced apart from the flange portion 27 as the inflow ceiling surface portion 36a comes closer to the flow channel boundary portion 34 from the inflow port 33a. In that case, for example, as shown in FIG. 3, since the intake air G flowing in from the inflow port 33a tends to gradually move away from the flow channel boundary portion 34 in the Y-direction, the small foreign matter that is easily susceptible to the flow of the intake air G can be inhibited from flowing into the measurement flow channel 32 in addition to the large foreign matter.

According to the present embodiment, since the height dimension Ha of the passage flow channel 31 increases more as the inflow step surface 41a is closer to the flow channel boundary portion 34, the change rate in the traveling direction of the intake air flowing in from the inflow port 33a can be gradually increased. In that case, as compared with the case where the change rate in the traveling direction of the intake air is abruptly increased, the flow of the intake air is hardly disturbed by the generation of a vortex or the like. For that reason, the flow rate of the intake air in the measurement flow channel 32 can be inhibited from being insufficient due to the intake air hardly flowing into the measurement flow channel 32 due to the turbulence of the flow, or the foreign matter entrained by the turbulence of the flow can be inhibited from entering the measurement flow channel 32.

According to the present embodiment, the inflow connection surface 42a extends in parallel with the depth direction Z. For that reason, the inflow connection surface 42a can be inhibited from becoming an obstacle to the foreign matter when the foreign matter entering from the inflow port 33a and traveling linearly in the depth direction Z reaches the inflow step surface 41a.

According to the present embodiment, since the inflow step surface 41a extends in parallel with the height direction Y, the inflow step surface 41a is orthogonal to the depth direction Z in which the intake air easily enters from the inflow port 33a. This makes it possible to inhibit that the foreign matter, which collides with the inflow step surface 41a and rebounds, advances to the downstream side in the direction inclined with respect to the height direction Y, collides with the bottom surface 37, and rebounds to enter the measurement flow channel 32.

According to the present embodiment, since the outflow ceiling surface portion 36b has the outflow step surface 41b, the foreign matter that has entered from the inflow port 33a and passed through the flow channel boundary portion 34 hardly enters the measurement flow channel 32. For example, as indicated by a dashed line in FIG. 3, when a large foreign matter F2 entering from the inflow port 33a travels linearly in the depth direction Z and collides with the outflow step surface 41b of the outflow ceiling surface portion 36b, the possibility that the large foreign matter F2 returns to the inflow port 33a so as to follow its own trajectory is high. As described above, the large foreign matter F2 collides with the outflow step surface 41b of the outflow ceiling surface portion 36b in the passage flow channel 31, and thus passes through the measurement flow channel 32 which has passed once in the opposite direction, but easily travels toward the upstream side at an angle which makes it difficult to enter the measurement flow channel 32.

On the contrary, unlike the present embodiment, for example, in a configuration in which the outflow ceiling surface portion 36b does not have the outflow step surface 41b as shown in FIG. 4, the outflow ceiling surface portion 36b is not orthogonal to the depth direction Z. For that reason, it is conceivable that the large foreign matter F2 collides with the outflow ceiling surface portion 36b which is inclined as a whole, and enters the measurement flow channel 32 by changing the traveling direction. Specifically, there is a concern that depending on the angle at which the large foreign matter F2 rebounds at the outflow ceiling surface portion 36b, as indicated by a dashed line in FIG. 4, the large foreign matter F2 is advanced upstream while rebounding at the bottom surface 37 following the outflow ceiling portion 36b, thereby making it easier to enter the measurement flow channel 32. As described above, when the traveling direction of the large foreign matter F2 changes in the height direction Y with the rebound at the outflow ceiling surface portion 36b, the possibility that the large foreign matter F2 flows into the measurement flow channel 32 is likely to increase. In that regard, in the present embodiment, since a configuration is realized in which the traveling direction of the large foreign matter F2 rebounded by the outflow step surface 41b of the outflow ceiling surface portion 36b is less likely to change in the height direction Y, the large foreign matter F2 can be inhibited from being likely to flow into the measurement flow channel 32.

As described above, there is a concern that the detection accuracy of the flow rate detection unit 22 is lowered if the flow velocity of the intake air flowing through the measurement flow channel 32 is too small in the air flow meter 10. On the contrary, according to the present embodiment, the cross-sectional area of the passage flow channel 31 is reduced by the outflow step surface 41b on the downstream side of the flow channel boundary portion 34, thereby narrowing the passage flow channel 31. In that case, the pressure of the intake air in the passage flow channel 31 becomes moderately high, so that the intake air is likely to flow into the measurement flow channel 32, and the flow rate of the intake air in the measurement flow channel 32 becomes moderately large. For that reason, the deterioration of the detection accuracy of the flow rate detection unit 22 can be inhibited by the outflow step surface 41b.

According to the present embodiment, since the multiple outflow step surfaces 41b are included in the outflow ceiling surface portion 36b, the degree of throttling of the passage flow channel 31 can gradually increase toward the outflow port 33b on the downstream side of the flow channel boundary portion 34. In that case, as compared with the configuration in which the degree of throttling of the passage flow channel 31 increases rapidly toward the outflow port 33b, the flow of intake air is less likely to be disturbed due to generation of a vortex or the like. For that reason, the foreign matter caught in the flow disturbance can be inhibited from entering the measurement flow channel 32.

According to the present embodiment, the height dimension Hb is smaller as the outflow step surface 41b is closer to the outflow port 33b. For that reason, a region around the flow channel boundary portion 34 in the passage flow channel 31 can be set to be as large as possible in the height direction Y. This makes it possible to realize a configuration in which the passage flow channel 31 is gradually narrowed by the outflow step surface 41b toward the outflow port 33b while creating a situation in which the intake air easily flows into the measurement flow channel 32 from the passage 31.

According to the present embodiment, the outflow connection surface 42b extends in parallel with the depth direction Z. For that reason, the outflow connection surface 42b can be inhibited from becoming an obstacle to the foreign matter when the foreign matter that has passed through the flow channel boundary portion 34 and has traveled linearly in the depth direction Z toward the outflow port 33b reaches the outflow step surface 41b.

According to the present embodiment, since the outflow step surface 41b extends in parallel with the height direction Y, the outflow step surface 41b is orthogonal to the depth direction Z which is likely to be the traveling direction of the intake air from the inflow port 33a. This makes it possible to inhibit that the foreign matter, which collides with the outflow step surface 41b and rebounds, flows back to the upstream side in the direction inclined with respect to the height direction Y, collides with the bottom surface 37, and rebounds to enter the measurement flow channel 32.

The first embodiment can be applied to various embodiments and combinations without departing from the spirit of the present disclosure.

As a modification A1, in the inflow step surface 41a, only one of the upstream end portion and the downstream end portion may be curved in accordance with the shape of the inflow port 33a, or both may not be curved. The inflow ceiling surface portion 36a may or may not be curved regardless of the shape of the inflow port 33a. For example, when the inflow port 33a has a rectangular shape, the inflow step surface 41a and the inflow connection surface 42a may be curved.

In a modification A2, the outflow port 33b may not be formed in a rectangular shape. In that case, the outflow step surface 41b and the outflow connection surface 42b may be curved outward or inward in accordance with the shape of the outflow port 33b.

Second Embodiment

In an air flow meter 10 of the first embodiment, the passage flow channel 31 and the measurement flow channel 32 do not overlap with each other in the width direction X, but in an air flow meter of a second embodiment, a passage flow channel and a measurement flow channel overlap with each other in the width direction X. In the second embodiment, differences from the first embodiment will be mainly described.

An air flow meter 50 illustrated in FIGS. 5 to 8 is a physical quantity detection device that detects a physical quantity of an intake air in an intake passage 12 in a state of being attached to an intake pipe 12b, as with the air flow meter 10 of the first embodiment. The air flow meter 50 includes a housing 51 and a flow rate detection unit 52, and the housing 51 includes a flow channel forming portion 54, an O-ring 56, a flange portion 57, a flange surface 57a, and a connector portion 58. Those members and parts correspond to members and parts having the same names as those of the first embodiment.

The O-ring 56 of the present embodiment does not enter an inner peripheral side of a flange portion 12c, but is sandwiched between a tip portion of the flange portion 12c and the flange portion 57. In that case, the flange surface 57a faces the tip end face of the flange portion 12c through the O-ring 56.

In the housing 51, a flow channel forming portion 54 is provided by a housing main body 51a, a front cover 51b, and a back cover 51c. The housing main body 51a extends from the flange portion 57 in the height direction Y, and the front cover 51b and the back cover 51c are attached to the housing main body 51a in a state in which the front cover 51b and the back cover 51c oppose each other in parallel with each other across the housing main body 51a in the width direction X. Both the housing main body 51a and the flange portion 57 are integrally formed by molding a synthetic resin material or the like. The front cover 51b and the back cover 51c are also made of a synthetic resin material.

The flow channel forming portion 54 has a passage flow channel 61 and a measurement flow channel 62, and the passage flow channel 61 has an inflow port 63a, an outflow port 63b, a measurement outlet 63c, a flow channel boundary portion 64, an upstream boundary portion 64a, and a downstream boundary portion 64b. An inner peripheral surface 61a of the passage flow channel 61 has a passage ceiling surface 66, an inflow ceiling surface portion 66a, an outflow ceiling surface portion 66b, a passage bottom surface 67, a passage wall surface 68, an inflow step surface 71a, and an inflow connection surface 72a. Those members and parts correspond to members and parts having the same names as those of the first embodiment. In the present embodiment, the passage bottom surface 67 extends in parallel with the depth direction Z.

In the present embodiment, unlike the first embodiment, the inner peripheral surface 61a of the passage flow channel 61 does not have an outflow step surface and an outflow connection surface. The inflow port 63a is formed in a rectangular shape, and the inflow ceiling surface portion 66a is not curved. For that reason, both a tip portion and a base end portion of the inflow step surface 71a linearly extend in the width direction X. The inflow connection surface 72a also extends linearly in the width direction X.

In the present embodiment, unlike the first embodiment, the flow channel boundary portion 34 extends parallel to the depth direction Z. Even in that case, since the upstream end portion of the measurement flow channel 62 is not opened toward the side of the inflow port 63a, even if the foreign matter traveling linearly in the depth direction Z enters from the inflow port 63a, the foreign matter does not easily enter the measurement flow channel 62 as it is.

Figure 9:
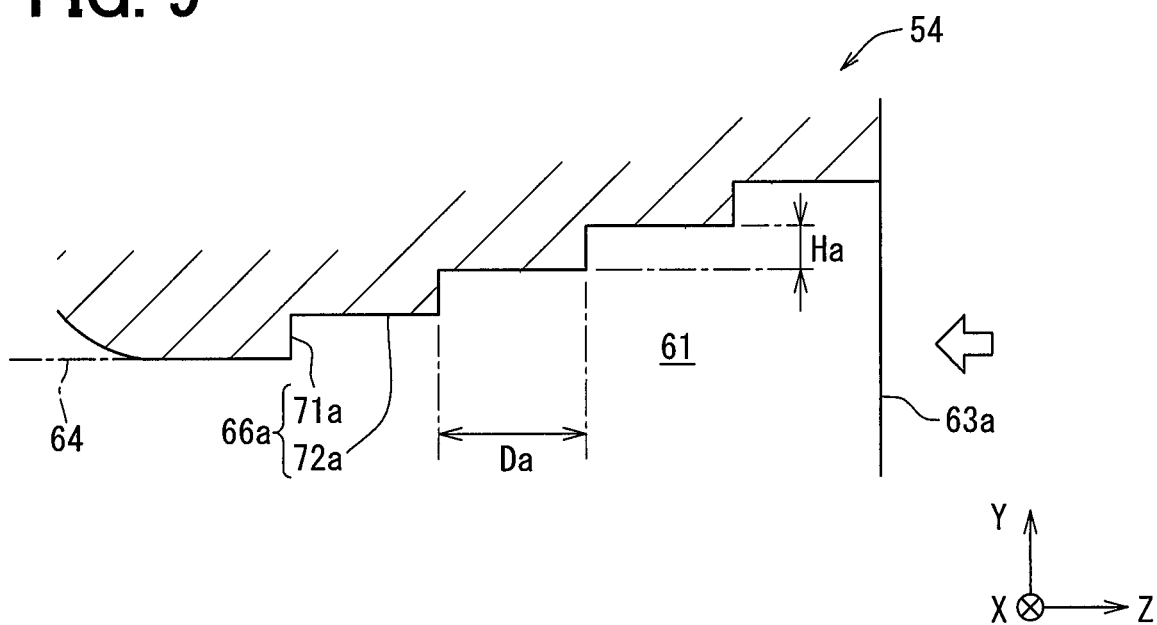
FIG. 9 is an enlarged view of the periphery of a step surface.

In the inflow ceiling surface portion 66a, unlike the first embodiment, the step is neither large nor small toward the downstream side, as shown in FIG. 9. Specifically, a depth interval Da and a height dimension Ha of each step have the same value. In that case, the entire angle of inclination in the inflow ceiling surface portion 66a is the same in a portion closer to the inflow port 63a and a portion closer to the flow channel boundary portion 64.

Figure 5:
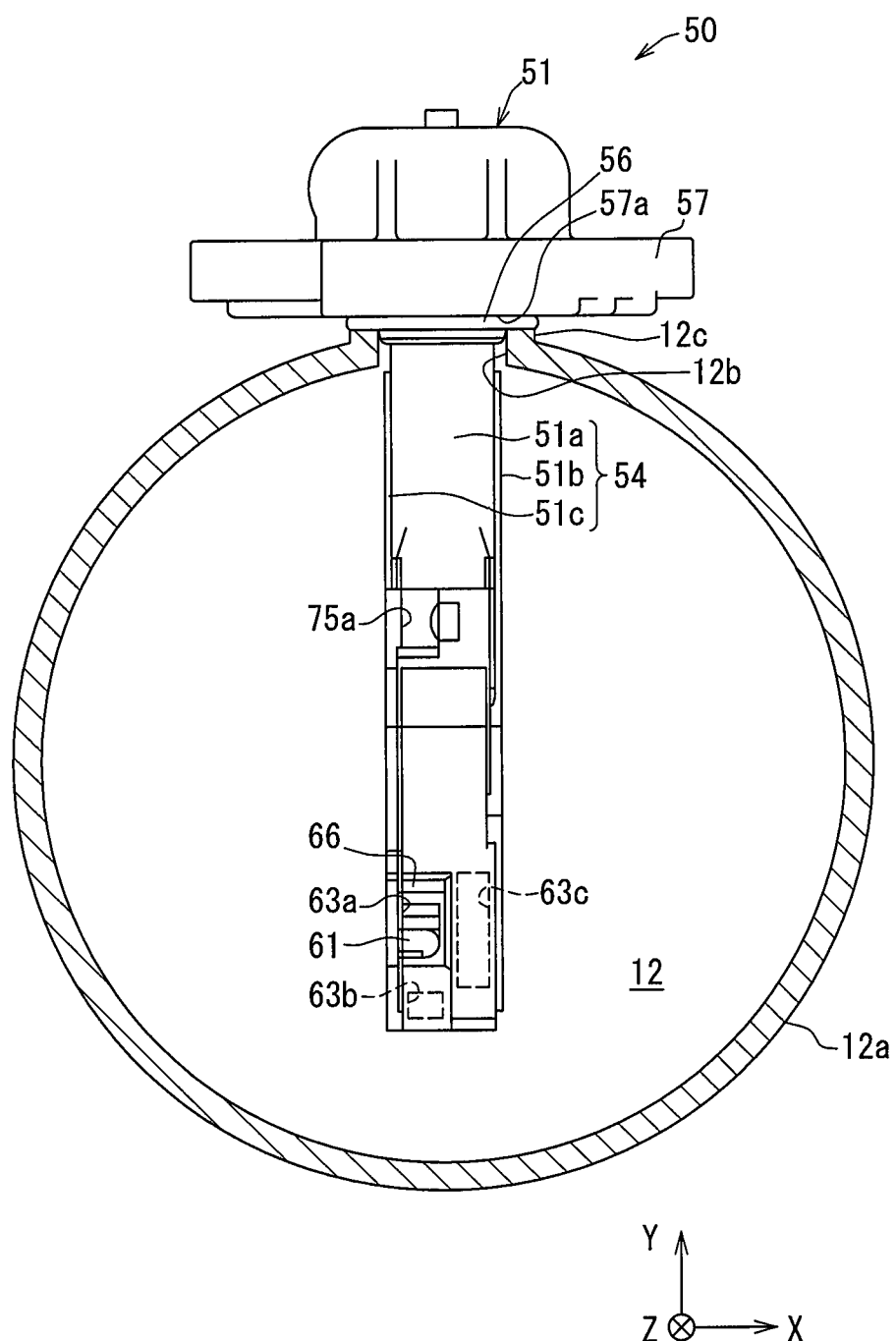
FIG. 5 is a front view of an air flow meter attached to an intake pipe as viewed from an upstream side according to a second embodiment.
Figure 6:
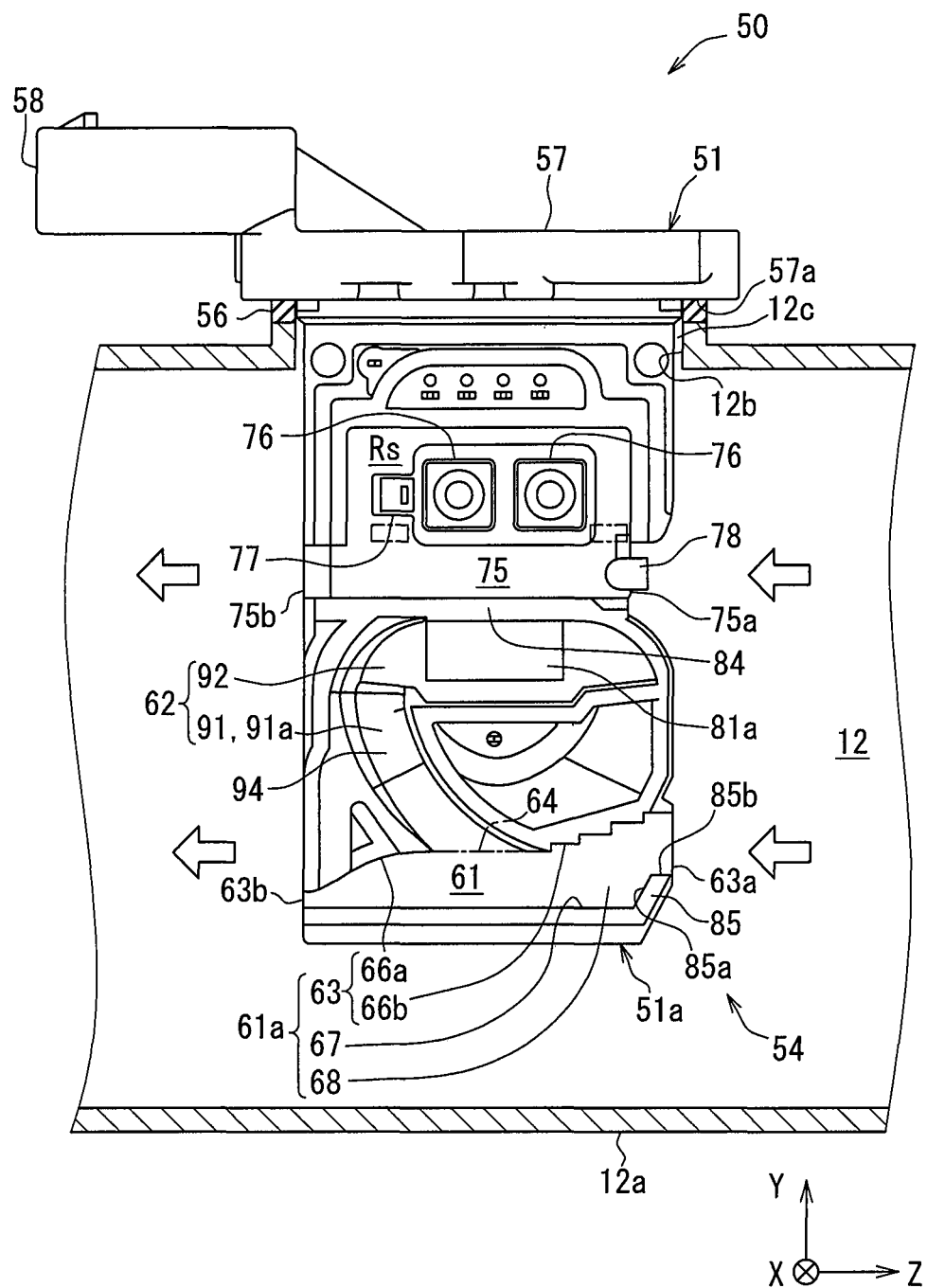
FIG. 6 is a view showing a configuration of a housing main body in a state in which a back cover in FIG. 5 is removed.
Figure 7:
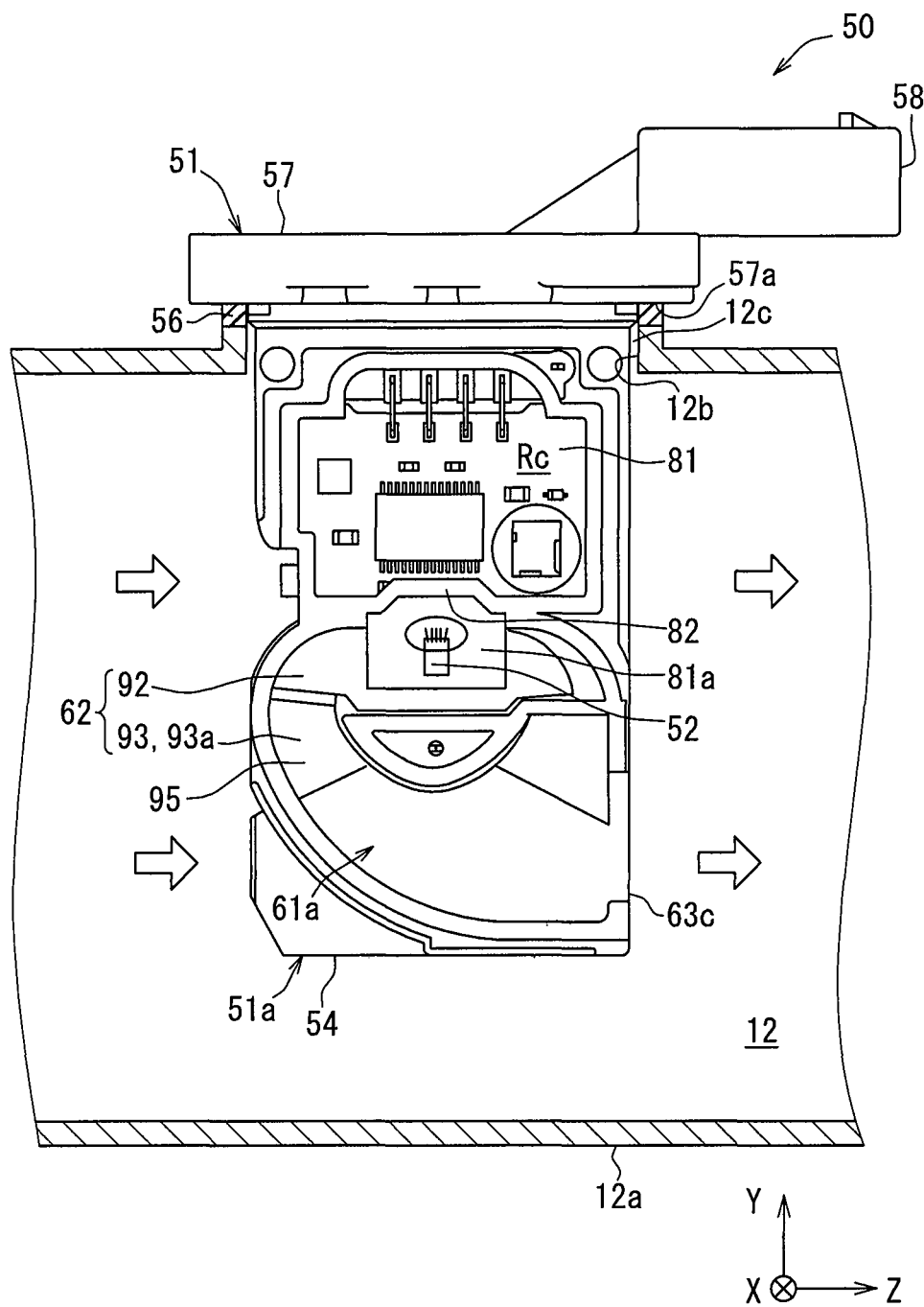
FIG. 7 is a view showing a configuration of a housing main body in a state in which a front cover in FIG. 5 is removed.

Returning to the description of FIGS. 5 to 7, the flow channel forming portion 54 has a sub-flow channel 75 in addition to the passage flow channel 61 and the measurement flow channel 62. The sub-flow channel 75 is provided between the flange portion 57 and the measurement flow channel 62 in the height direction Y, and extends in the depth direction Z. When an upstream end portion of the sub-flow channel 75 is referred to as a sub-inlet 75a and a downstream end portion of the sub-flow channel 75 is referred to as a sub-outlet 75b, the sub-inlet 75a is disposed between the flange portion 57 and the inflow port 33a in the height direction Y, and the sub-outlet 75b is disposed between the flange portion 57 and the outflow port 33b. The air flow meter 50 includes a pressure detection unit 76, a humidity detection unit 77, and a temperature detection unit 78 in addition to the flow rate detection unit 52, and the pressure detection unit 76 and the humidity detection unit 77 detect a pressure and a humidity of the intake air in the sub-flow channel 75.

In the housing main body 51a, a circuit board 81 is integrally provided by insert molding when the housing main body 51a is molded. The circuit board 81 is provided with at least one detection element for detecting a physical quantity of the intake air flowing through the intake passage 12, and a circuit unit for processing a signal detected by the detection element. The detection element is provided at a position of the front surface or the back surface of the circuit board 81 which is exposed to the intake air, that is, at a portion which is exposed to the intake air in the intake passage 12, the measurement flow channel 62, and the sub-flow channel 75 and comes into contact with the intake air. The electrical connection portion between the circuit board 81 and the detection element is sealed with a synthetic resin material. The circuit unit is disposed in a circuit chamber Rc sealed by the front cover 51b.

The housing main body 51a is provided with a groove opened toward one side or the other side in the width direction X, and a hole penetrating through the housing main body 51a in the width direction X. The groove and the hole are covered with the front cover 51b and the back cover 51c, to thereby provide the passage flow channel 61, the measurement flow channel 62, and the sub-flow channel 75. A sensor chamber Rs is provided at an intermediate position of the sub-flow channel 75, and the sensor chamber Rs is provided with a pressure detection unit 76 and a humidity detection unit 77 as detection elements provided on the back surface of the circuit board 81. The pressure detection unit 76 and the humidity detection unit 77 can detect a pressure and a humidity of the intake air flowing through the sub-flow channel 75, respectively.

The circuit board 81 is provided at an intermediate position of the housing main body 51a in the width direction X in a state orthogonal to the width direction X, thereby partitioning the circuit chamber Rc and the sensor chamber Rs. The circuit chamber Rc is provided between the front cover 51b and the circuit board 81, and the sensor chamber Rs is provided between the back cover 51c and the circuit board 81. The circuit chamber Rc is sealed by attaching the front cover 51b to the housing 51, and is completely isolated from an outside.

The flow channel forming portion 54 has a partition wall 84 that separates the measurement flow channel 62 and the sub-flow channel 75 from each other in the height direction Y. The circuit board 81 penetrates the partition wall 84 in the height direction Y and protrudes into the measurement flow channel 62, and the flow rate detection unit 52 is provided in a measurement board portion 81a which is a protruding portion.

In a state in which the air flow meter 50 is attached to the intake pipe 12a, an intermediate position between the inflow port 63a and the sub-inlet port 75a in the height direction Y is disposed at a position overlapping with or close to a center line of the intake pipe 12a. In the above configuration, a gas at a portion close to an inner wall surface of the intake passage 12 but at a portion close to the center away from the inner wall is likely to flow into the passage flow channel 61 or the sub-flow channel 75. In that case, the air flow meter 50 can measure the physical quantity of the gas in a portion away from the inner wall surface of the intake passage 12, and can reduce a measurement error of the physical quantity related to a heat and a flow rate decrease in the vicinity of the inner wall surface.

The flow channel forming portion 54 has an inflow restriction portion 85 that restricts the inflow of the intake air from the inflow port 63a. The inflow restriction portion 85 is a projection portion protruding from the passage bottom surface 67 of the passage flow channel 61 toward the passage ceiling surface 66. The inflow restriction portion 85 has a downstream side surface 85a facing the downstream side and an upper surface 85b facing the passage ceiling surface 66 (hereinafter, also referred to as a ceiling side) and the downstream side surface 85a and the upper surface 85b are included in the passage bottom surface 67. The inflow restriction portion 85 is provided in the inflow port 63a, and the upstream end portion of the upper surface 85b is included in the inflow port 63a. The downstream side surface 85a extends obliquely upward toward the upstream side, and the upper surface 85b extends parallel to the depth direction Z.

The inflow restriction portion 85 extends over the pair of passage wall surfaces 68, and the opening area of the inflow port 63a is reduced by reducing the height dimension of the inflow port 63a in the height direction. The inflow restriction portion 85 is inclined with respect to the height Y by extending in a direction away from the outflow port 63b toward the passage ceiling surface 66 rather than extending parallel to the height direction Y.

In the present embodiment, as described above, the portion closer to the outflow port 63b in the passage flow channel 61 and the portion closer to the measurement outlet 63c in the measurement flow channel 62 overlap with each other in the width direction X. In the flow channel forming portion 54, a groove is provided in the housing main body 51a, so that the passage flow channel 61 is provided between the housing main body 51a and the back cover 51c. The measurement flow channel 62 has an upstream measurement path 91, an intermediate measurement path 92, and a downstream measurement path 93. The upstream measurement path 91 extends from the flow channel boundary portion 64 to the downstream side of the measurement flow channel 62 and is provided between the housing main body 51a and the back cover 51c as well as the passage flow channel 61. The downstream measurement path 93 extends from the measurement outlet 63c to the upstream side of the measurement flow channel 62, and is provided between the housing main body 51a and the front cover 51b. The downstream measurement path 93 is disposed on the opposite side of the upstream measurement path 91 and the passage flow channel 61 across the housing main body 51a in the width direction X.

The intermediate measurement path 92 is a portion connecting the upstream measurement path 91 and the downstream measurement path 93 in the measurement flow channel 62, and is disposed in a portion where a hole is provided in the housing main body 51a, so that the intermediate measurement path 92 is provided between the front cover 51b and the back cover 51c through the hole. The intermediate measurement path 92 extends in the depth direction Z, and the intake air flows in the intermediate measurement path 92 in the opposite direction to the intake passage 12. The intermediate measurement path 92 is divided from the sub-flow channel 75 by the partition wall 84, and the measurement board portion 81a of the circuit board 81 is disposed in the intermediate measurement path 92. For that reason, the flow rate detection unit 52 provided in the intermediate measurement path 92 detects the flow rate of the intake air flowing through the intermediate measurement path 92.

In the width direction X, a width dimension of the intermediate measurement path 92 is larger than the width dimensions of the upstream measurement path 91 and the downstream measurement path 93. The upstream measurement path 91 has a width increasing portion 91a whose width dimension gradually increases toward the intermediate measurement path 92, and the downstream measurement path 93 has a width decreasing portion 93a whose width dimension gradually decreases away from the intermediate measurement path 92. The housing main body 51a has a width increasing surface 94 forming the width increasing portion 91a and a width decreasing surface 95 forming the width decreasing portion 93a. The width increasing surface 94 is included in a surface of the housing main body 51a facing the back cover 51c, is not orthogonal to the width direction X, and is inclined with respect to the width direction X by facing the intermediate measurement path 92. The width decreasing surface 95 is included in a surface of the housing main body 51a facing the front cover 51b, and is inclined with respect to the width direction X by facing the intermediate measurement path 92, similarly to the width increasing surface 94.

The flow rate detection unit 52 is disposed on a surface of the measurement board portion 81a facing the front cover 51b. In the intermediate measurement path 92, the flow rate detection unit 52 is disposed on the downstream side of the width increasing surface 94. In that case, since the flow rate detection unit 52 is hidden behind the width increasing surface 94, even if the foreign matter enters the measurement flow channel 62 from the passage flow channel 61, the width increasing surface 94 becomes an obstacle and the foreign matter is less likely to reach the flow rate detection unit 52.

Figure 8:
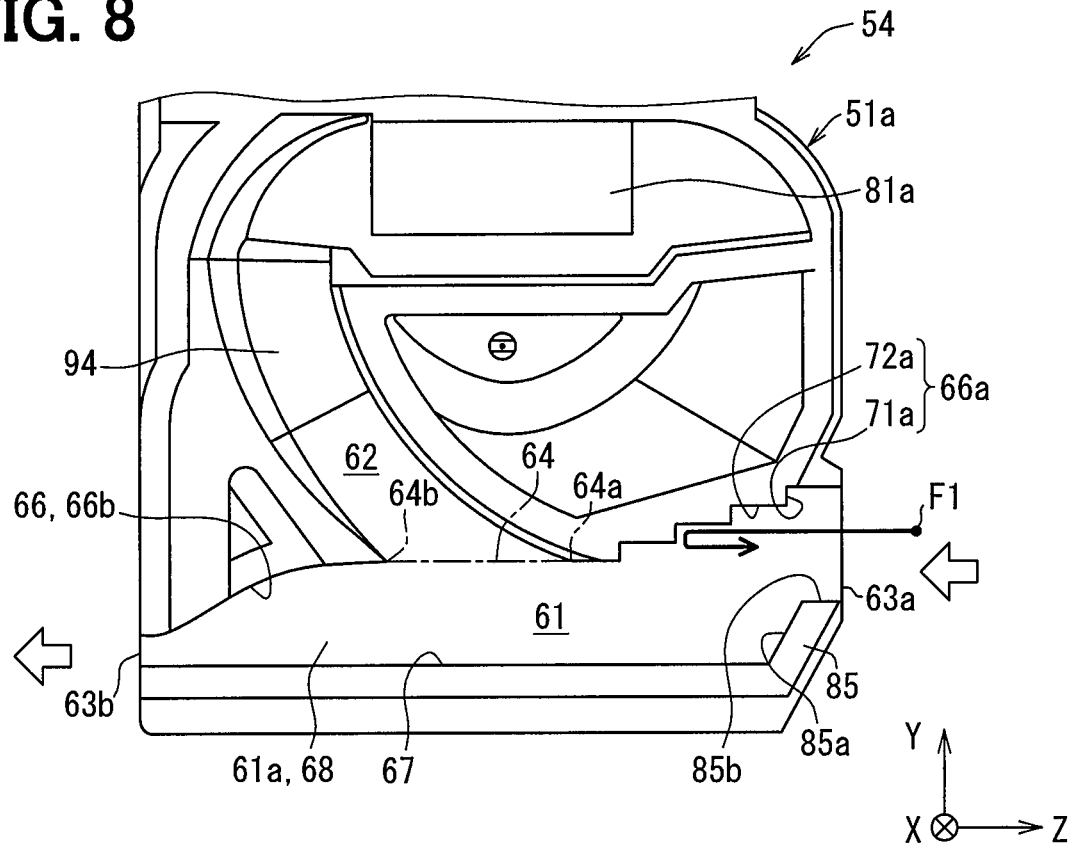
FIG. 8 is a diagram the periphery of a passage flow channel in FIG. 6.
Figure 10:
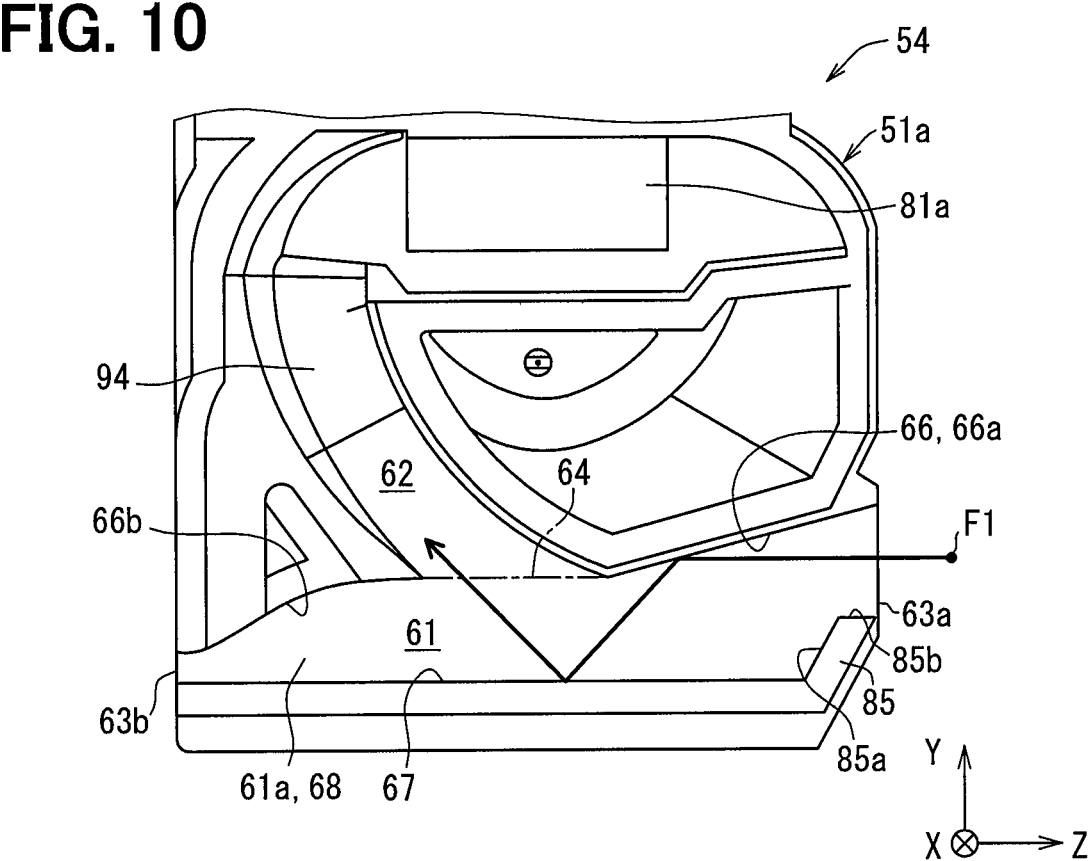
FIG. 10 is a diagram illustrating a configuration in which a ceiling surface of the passage flow channel has no inflow step surface, unlike the second embodiment.

According to the present embodiment described so far, similarly to the first embodiment, since the inflow ceiling surface portion 66a has the inflow step surface 71a, the foreign matter that has entered from the inflow port 63a is less likely to enter the measurement flow channel 62. The inflow step surface 71a is orthogonal to the depth direction Z. For that reason, similarly to FIG. 3, when the large foreign matter F1 entering from the inflow port 63a moves linearly in the depth direction Z and collides with the inflow step surface 71a as shown in FIG. 8, it is considered that the possibility that the large foreign matter F1 returns to the inflow port 63a so as to follow its own trajectory is high. On the other hand, unlike the present embodiment, in the configuration in which the inflow ceiling surface portion 66a does not have the inflow step surface 71a as shown in FIG. 10, the inflow ceiling surface portion 66a is not orthogonal to the depth direction Z, similarly to FIG. 4. For that reason, there is a concern that the large foreign matter F1 collides with the inflow ceiling surface portion 66a which is inclined as a whole, and enters the measurement flow channel 62 while changing the traveling direction. In that regard, in the present embodiment, the inflow ceiling surface portion 66a restricts the rebound direction of the large foreign matter F1, thereby being capable of inhibiting the large foreign matter F1 from entering the measurement flow channel 62.

According to the present embodiment, since the inflow restriction portion 85 is provided on the passage bottom surface 67 on the opposite side of the inflow step surface 71a across the inflow port 63a, a probability that the foreign matter entering from the inflow port 63a and traveling linearly collides with the inflow step surface 71a. This is because a region of the inflow port 63a which does not face the inflow step surface 71a, that is, a region which is not aligned with the inflow step surface 71a in the depth direction Z can be closed by the inflow step surface 71a. For that reason, the foreign matter can be inhibited from entering the measurement flow channel 62 without colliding with the inflow step surface 71a.

The second embodiment can be applied to various embodiments and combinations without departing from the spirit of the present disclosure.

Figure 11:
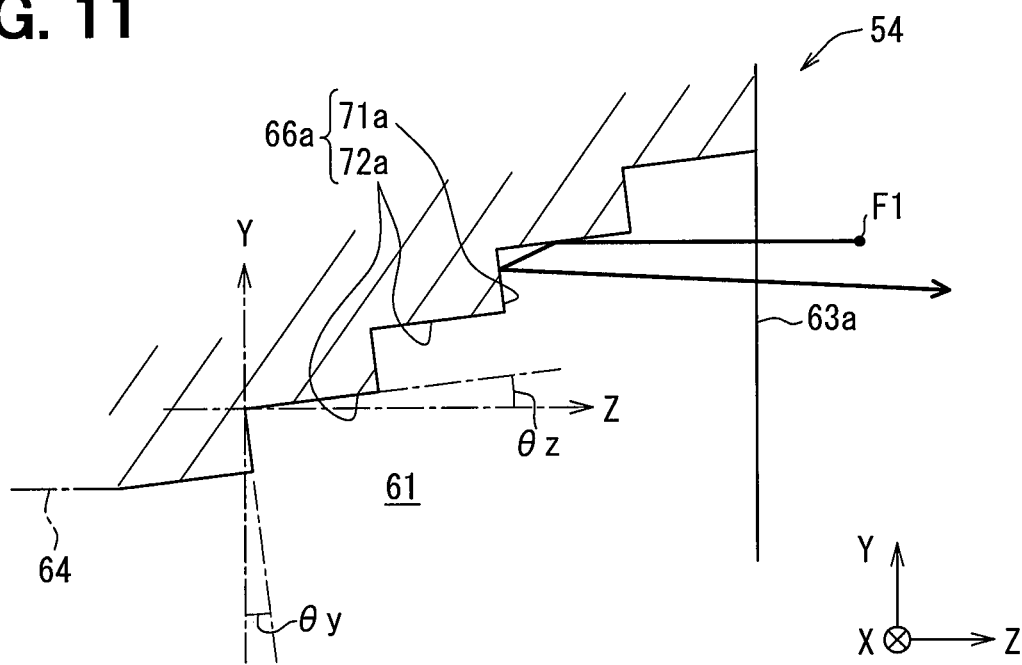
FIG. 11 is an enlarged view of the periphery of a step surface in a modification B1.

As a modification B1, the inflow step surface 71a may not be parallel to the depth direction Z. For example, as shown in FIG. 11, the inflow step surface 71a extends obliquely upward toward the upstream side. In that configuration, the inflow connection surface 72a is orthogonal to the inflow step surface 71a, and the inflow connection surface 72a extends obliquely downward toward the upstream side. When an angle between the inflow step surface 71a and the depth direction Z is referred to as a step angle θz, and an angle between the inflow connection surface 72a and the height direction Y is referred to as a connection angle θy, the step angle θz and the connection angle θy are the same angles. The angles θz and θy are positive and have relatively small absolute values of several degrees to several tens of degrees. For that reason, for example, even if the large foreign matter F1 traveling linearly in the depth direction Z collides with the inflow step surface 71a or the inflow connection surface 72a, the large foreign matter F1 tends to return toward the inflow port 63a in substantially the same direction as the depth direction Z.

Figure 12:
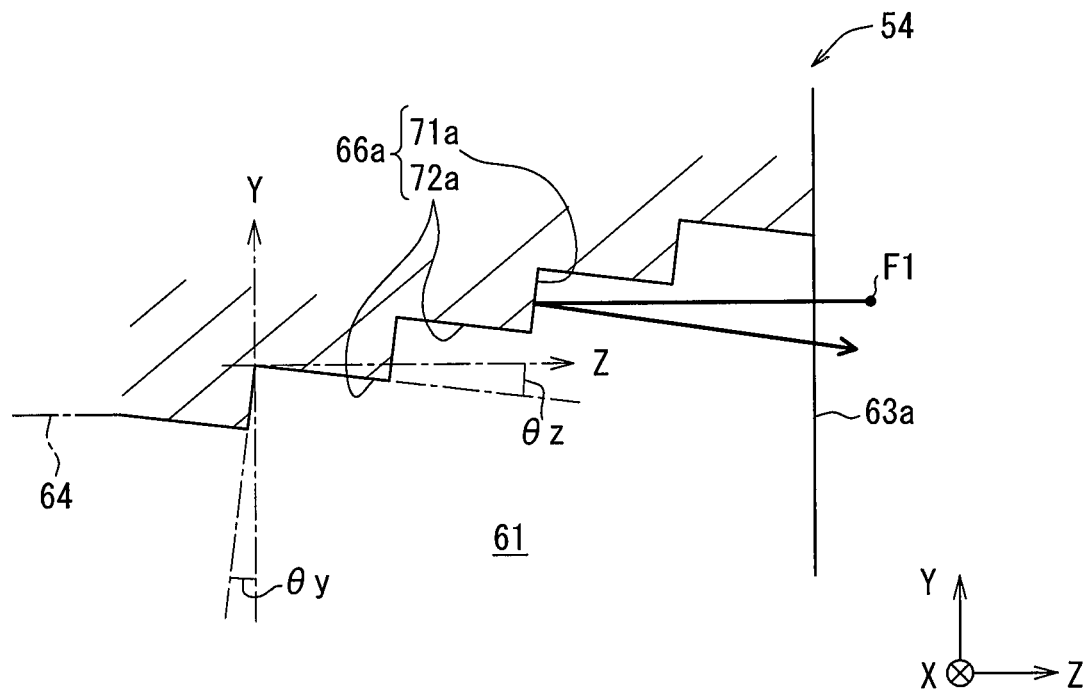
FIG. 12 is an enlarged view of the periphery of the step surface in the modification B1.

As shown in FIG. 12, the inflow step surface 71a extends obliquely downward toward the upstream side. In that configuration, the inflow connection surface 72a is orthogonal to the inflow step surface 71a, and the inflow connection surface 72a extends obliquely downward toward the downstream side. In that case, the step angle θz and the connection angle θy are negative values and have relatively small absolute values of several degrees to several tens of degrees. Even in that case, the large foreign matter F1 rebounded at the inflow step surface 71a and the inflow connection surface 72a tends to return toward the inflow port 63a in substantially the same direction as the depth direction Z.

As a modification B2, the inflow step surface 71a and the inflow connection surface 72a may not be orthogonal to each other. For example, the angle between the inflow step surface 71a and the inflow connection surface 72a may be smaller than 90 degrees or larger than 90 degrees. It is preferable that a difference between the angle and 90 degrees is small to the extent that when the large foreign matter F1 traveling linearly in the depth direction Z collides with the inflow step surface 71a or the inflow connection surface 72a, the large foreign matter F1 tends to return toward the inflow port 63a in substantially the same direction as the depth direction Z. Preferred values include relatively small absolute values, such as a few degrees to several degrees severity.

Figure 13:
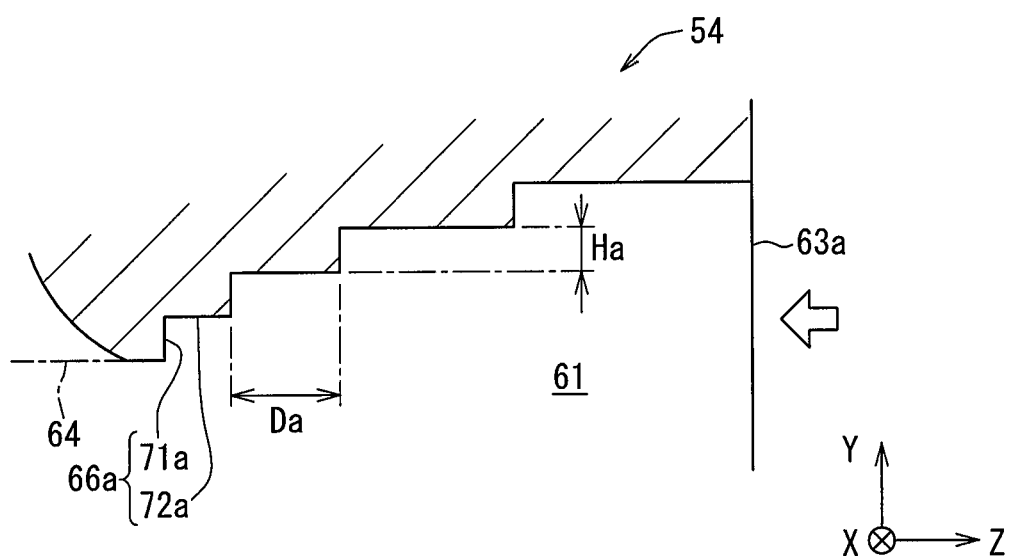
FIG. 13 is an enlarged view of the periphery of a step surface in a modification B3.

As a modification B3, the height dimension Ha of the inflow step surface 71a may not be the same in each step of the inflow ceiling surface portion 66a. For example, as shown in FIG. 13, the height dimension Ha of the inflow step surface 71a gradually decreases as a distance from the inflow port 63a increases. In that configuration, the depth interval Da is the same for each step. The height dimension Ha of the inflow step surface 71a may gradually increase as the distance from the inflow port 63a increases.

Figure 14:
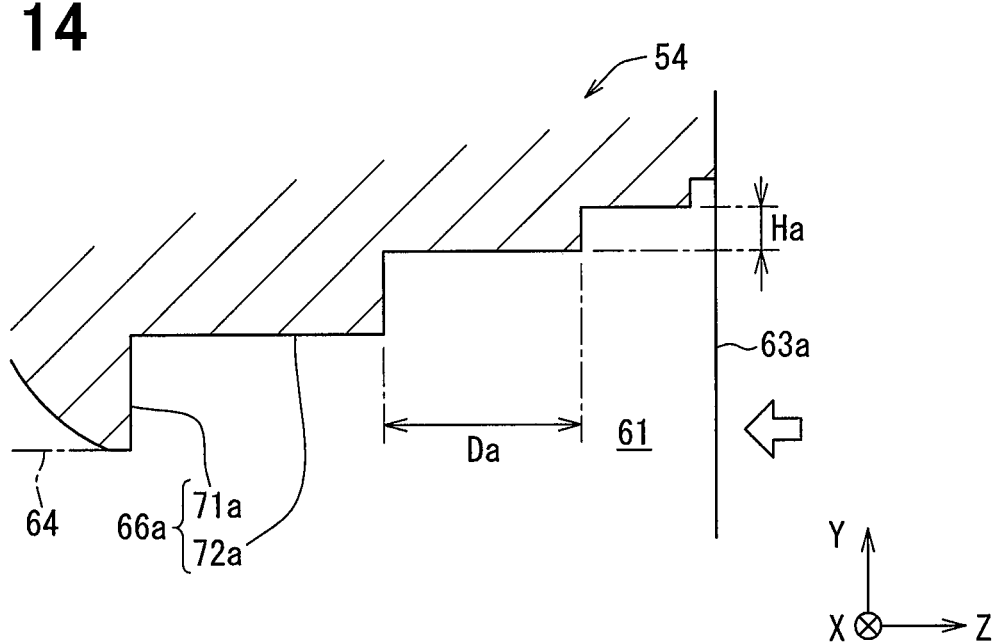
FIG. 14 is an enlarged view of the periphery of a step surface in a modification B4.

As a modification B4, in each step of the inflow ceiling surface portion 66a, both the height dimension Ha and the depth interval Da of the inflow step surface 71a may be different from each other. For example, as shown in FIG. 14, in each step of the inflow ceiling surface portion 66a, both the height dimension Ha and the depth interval Da gradually increase as the distance from the inflow port 63a increases. It should be noted that both the height dimension Ha and the depth interval Da may gradually decrease as the distance from the inflow port 63a increases.

Figure 15:
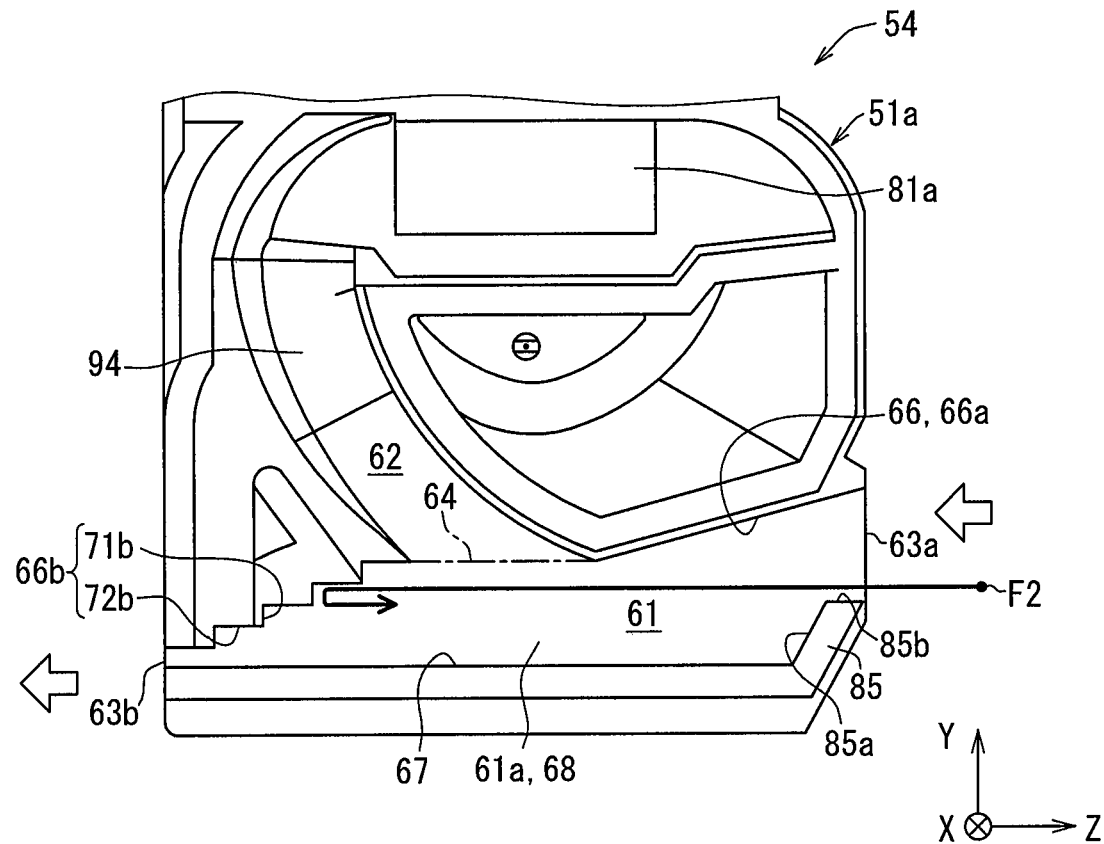
FIG. 15 is a diagram of the periphery of a passage flow channel in a modification B5.

As a modification B5, similarly to the first embodiment, the air flow meter 50 of the second embodiment may have an outflow step surface and an outflow connection surface. For example, as shown in FIG. 15, in the inner peripheral surface 61a of the passage flow channel 61, an outflow ceiling surface portion 66b of the passage ceiling surface 66 has an outflow step surface 71b and an outflow connection surface 72b. While the outflow step surface 71b and the outflow connection surface 72b correspond to the same named parts of the first embodiment, in this configuration, the inflow ceiling surface portion 66a does not have the inflow step surface 71a and the inflow connection surface 72a. Similarly, in the above configuration, the outflow step surface 71b is orthogonal to the depth direction. For that reason, similarly to FIG. 3, when the large foreign matter F2 entering from the inflow port 63a travels linearly in the depth direction Z and collides with the outflow step surface 71b as shown in FIG. 15, it is considered highly likely that the large foreign matter F2 returns to the inflow port 63a so as to follow its own trajectory.

Figure 16:
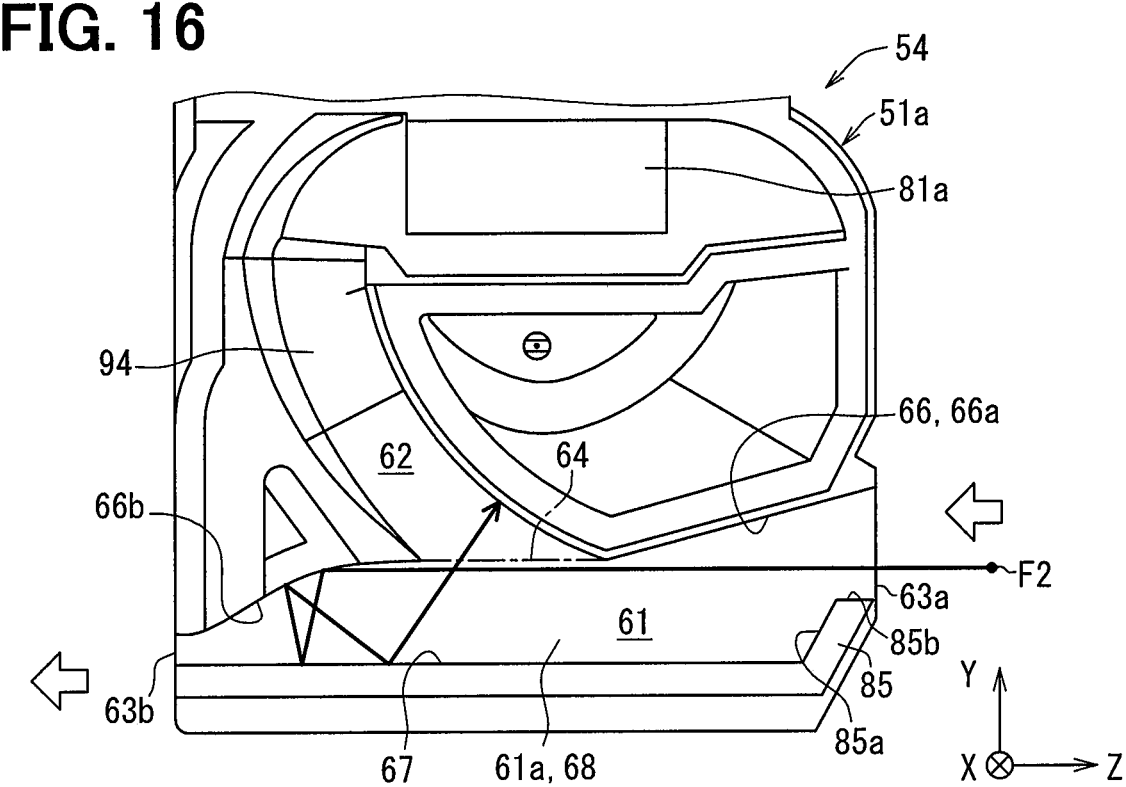
FIG. 16 is a diagram illustrating a configuration in which the ceiling surface of the passage flow channel has no outflow step surface, unlike the modification B5.

On the other hand, unlike the present embodiment, in the configuration in which the outflow ceiling surface portion 66b does not have the outflow step surface 71b as illustrated in FIG. 16, the outflow ceiling surface portion 66b does not have a portion perpendicular to the depth direction as illustrated in FIG. 4. For that reason, there is a concern that the large foreign matter F2 collides with the outflow ceiling surface portion 66b which is inclined as a whole, and enters the measurement flow channel 62 by changing the traveling direction. In that regard, according to the present embodiment, the outflow ceiling surface portion 66b restricts the rebound direction of the large foreign matter F2, thereby being capable of inhibiting the large foreign matter F2 from entering the measurement flow channel 62.

The modification B1 may be applied to the modification B4, and the outflow step surface 71b may not be parallel to the depth direction Zb. For example, the outflow step surface 71b extends obliquely upward or obliquely downward toward the upstream side. In addition, the modification B2 may be applied to the modification B4, and the outflow step surface 71b and the outflow connection surface 72b may not be orthogonal to each other.

Figure 17:
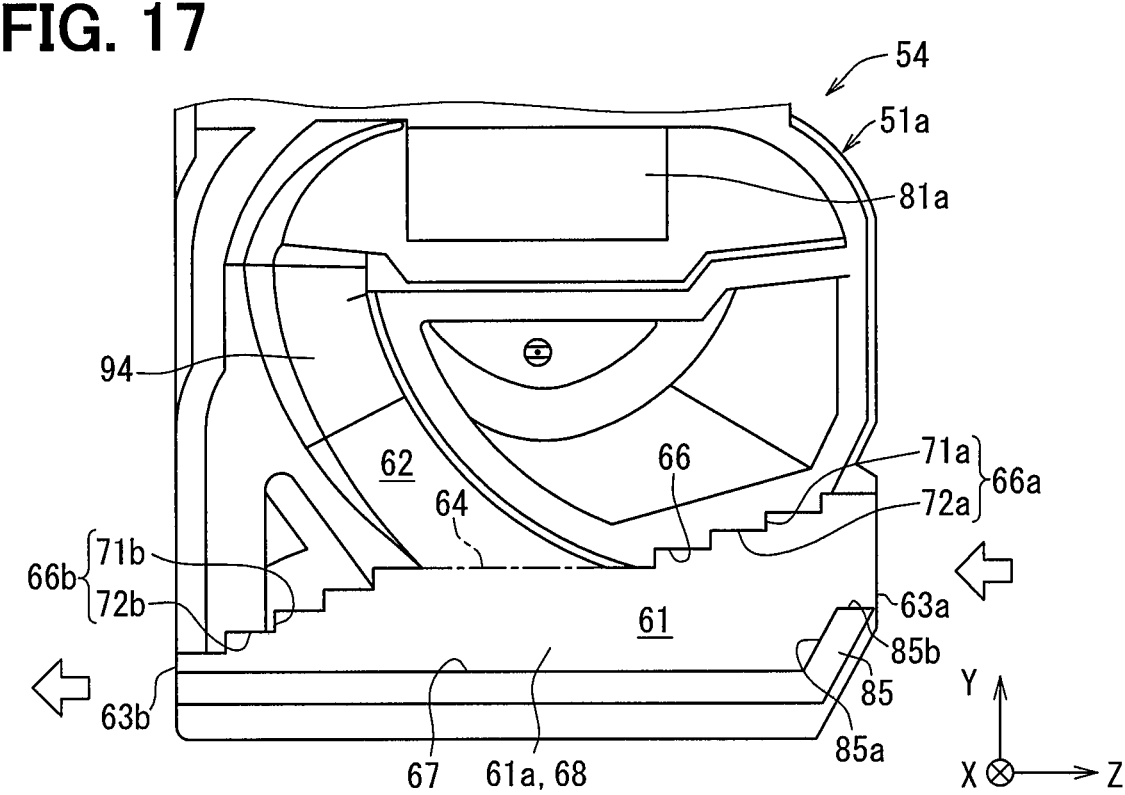
FIG. 17 is a diagram of the periphery of the passage flow channel in a modification B6.

As a modification B6, in the modification B5, as shown in FIG. 17, the passage ceiling surface 66 may have the inflow step surface 71a and the inflow connection surface 72a in addition to the outflow step surface 71b and the outflow connection surface 72b. In the above configuration, similarly to the first embodiment, both of the large foreign matter F1 colliding with the inflow ceiling surface portion 66a and the large foreign matter F2 colliding with the outflow ceiling surface portion 66b can exert a deterrent force against entering the measurement flow channel 62.

Figure 18:
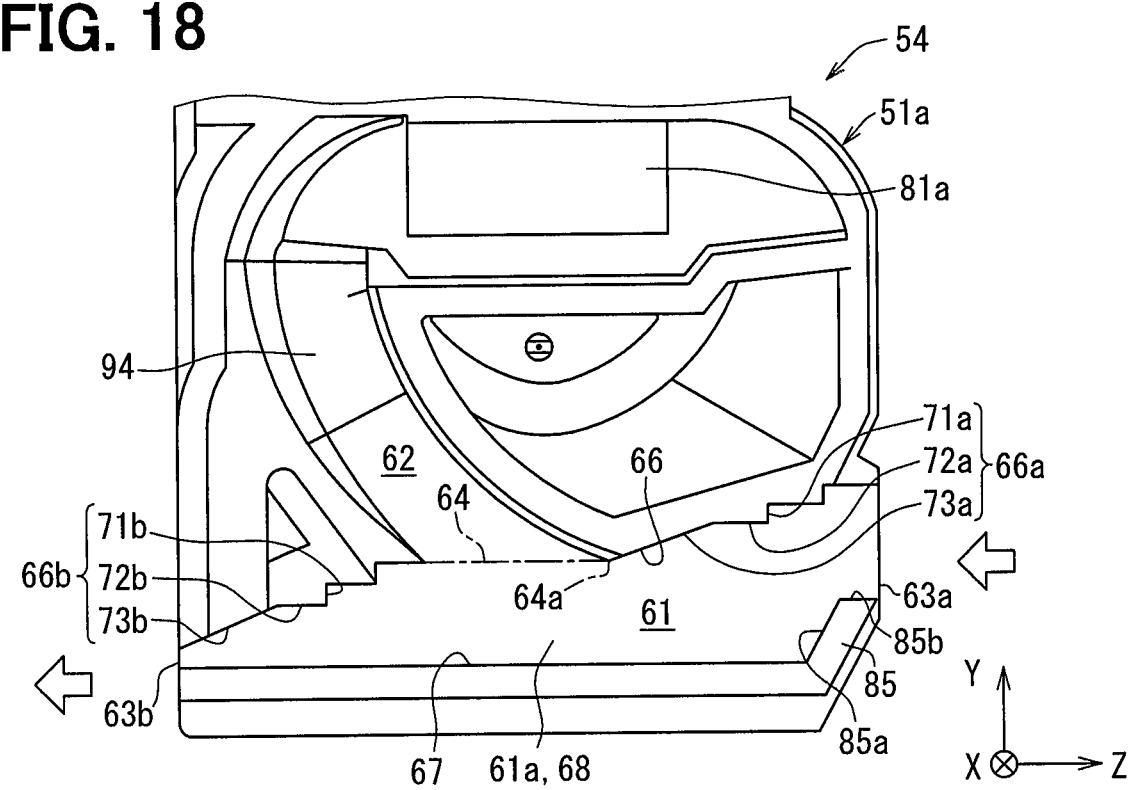
FIG. 18 is a diagram of the periphery of a passage flow channel in a modification B7.

As a modification B7, a step may not be formed on the entire inflow ceiling surface portion 66a. For example, as shown in FIG. 18, the inflow ceiling surface portion 66a has an inflow non-step surface 73a in addition to the inflow step surface 71a and the inflow connection surface 72a. The inflow non-step surface 73a extends obliquely downward from the downstream end portion of the inflow step surface 71a disposed at the most downstream side toward the downstream side, and the downstream end portion of the inflow non-step surface 73a is disposed at the upstream boundary portion 64a. Even in the above configuration, a deterrent force against the large foreign matter F1 entering the measurement flow channel 62 can be exerted on the inflow step surface 71a. The inflow non-step surface 73a may be disposed upstream of any of the inflow step surfaces 71a or may be disposed between the multiple inflow step surfaces 71a. The inflow non-step surface 73a may extend obliquely upward toward the downstream side, or may extend parallel to the depth direction Z.

The modification B7 is applied to the modification B4, and the step may not be formed on the entire outflow ceiling surface portion 66b. For example, as shown in FIG. 18, the outflow ceiling surface portion 66b has an outflow non-step surface 73b in addition to the outflow step surface 71b and the outflow connection surface 72b. The outflow non-step surface 73b extends obliquely downward from the downstream end portion of the outflow step surface 71b disposed at the most downstream side toward the downstream side, and a downstream end portion of the outflow non-step surface 73b is disposed at the outflow port 63b. Even in the above configuration, the outflow step surface 71b can exert a deterrent force against the large foreign matter F2 entering the measurement flow channel 62. The outflow non-step surface 73b may be disposed on the upstream side of any of the outflow step surfaces 71b, or may be disposed between the multiple outflow step surfaces 71b. The outflow non-step surface 73b may extend obliquely upward toward the downstream side, or may extend parallel to the depth direction Z.

Figure 19:
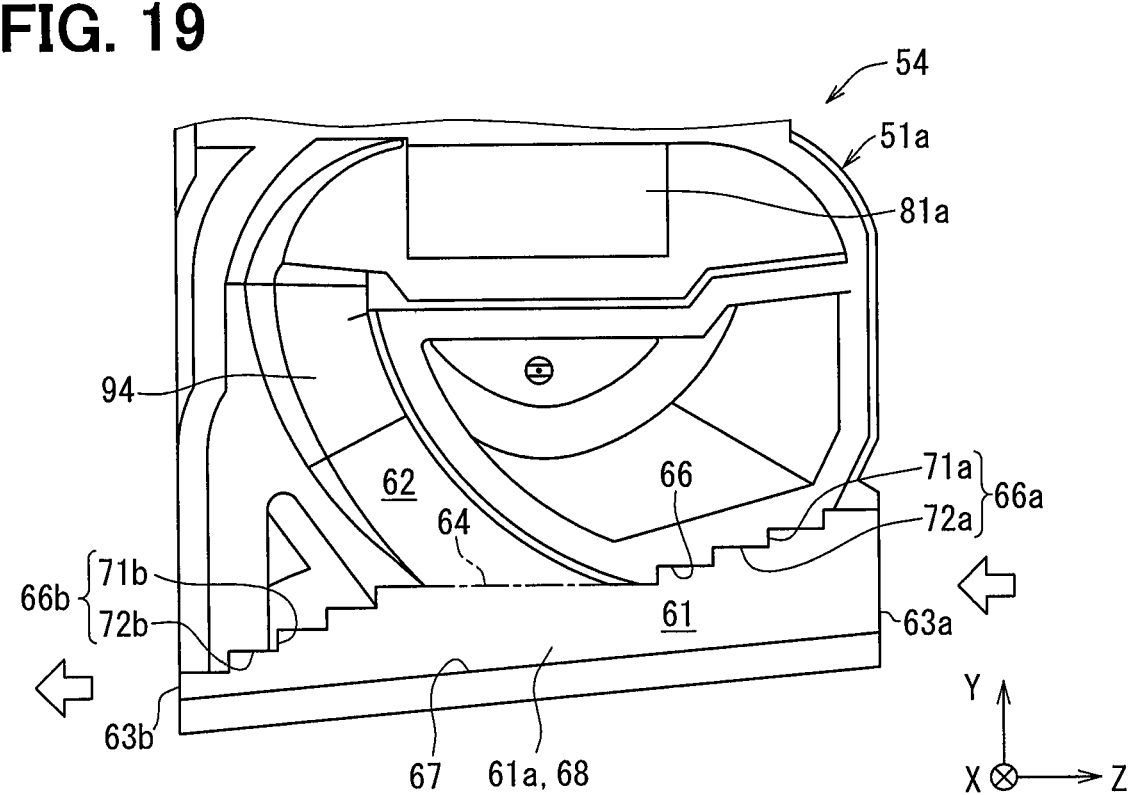
FIG. 19 is a diagram of the periphery of a passage flow channel in a modification B8.
Figure 20:
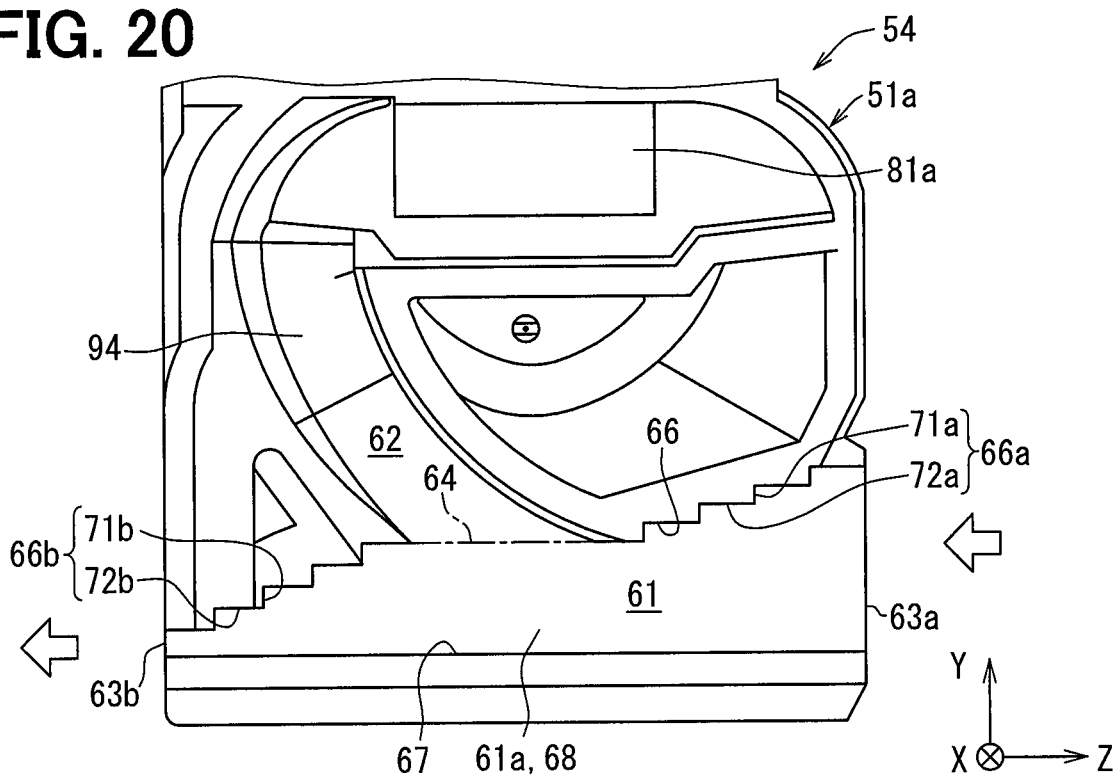
FIG. 20 is a diagram of the periphery of a passage flow channel in a modification B9.

As a modification B8, the passage bottom surface 67 may be inclined with respect to the depth direction Z. For example, as shown in FIG. 19, the passage bottom surface 67 extends obliquely upward toward the upstream side. In the above configuration, the passage bottom surface 67 inclined with respect to the depth direction Z is extended linearly over the inflow port 63a and the outflow port 63b. In that case, the flow channel forming portion 54 does not have the inflow restriction portion 85. As a modification B9, as shown in FIG. 20, the flow channel forming portion 54 may not have the inflow restriction portion 85. In that case, at least a part of the outflow ceiling surface portion 66b is not hidden from the upstream side by the inflow restriction portion 85 in the depth direction Z. For that reason, all the outflow step surfaces 71b are exposed to the upstream side through the inflow port 63a.

Figure 21:
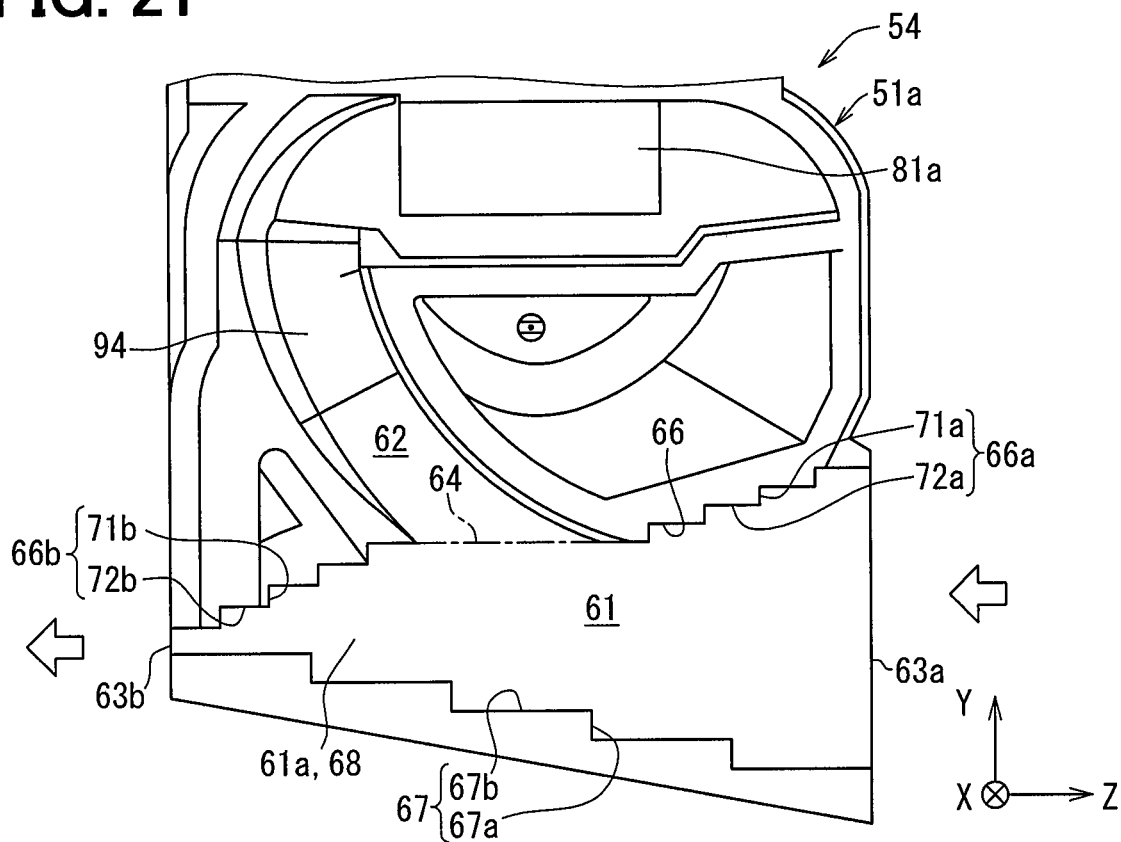
FIG. 21 is a diagram of the periphery of a passage flow channel in a modification B10.

As a modification B10, the passage bottom surface 67 may have steps. For example, as shown in FIG. 21, the passage bottom surface 67 has bottom step surfaces 67a and bottom connection surfaces 67b. The multiple bottom step surfaces 67a are perpendicular to the depth direction Z in the same manner as the inflow step surfaces 71a and the outflow step surfaces 71b, and aligned in the depth direction Z at predetermined intervals. An installation interval of the bottom step surfaces 67a is larger than the depth interval Da of the inflow step surfaces 71a and the depth interval Db of the outflow step surfaces 71b. Like the inflow connection surfaces 72a and the outflow connection surfaces 72b, the bottom connection surfaces 67b extend parallel to the depth direction Z and connect the adjacent bottom step surfaces 67a.

In the configuration in which the passage bottom surface 67 has the bottom step surfaces 67a and the bottom connection surfaces 67b, the passage ceiling surface 66 may not have the inflow step surfaces 71a and the outflow step surfaces 71b. In that case, both of the large foreign matter colliding with the passage bottom surface 67 can exert a deterrent force against entering the measurement flow channel 62 by changing the traveling direction of the large foreign matter.

Figure 22:
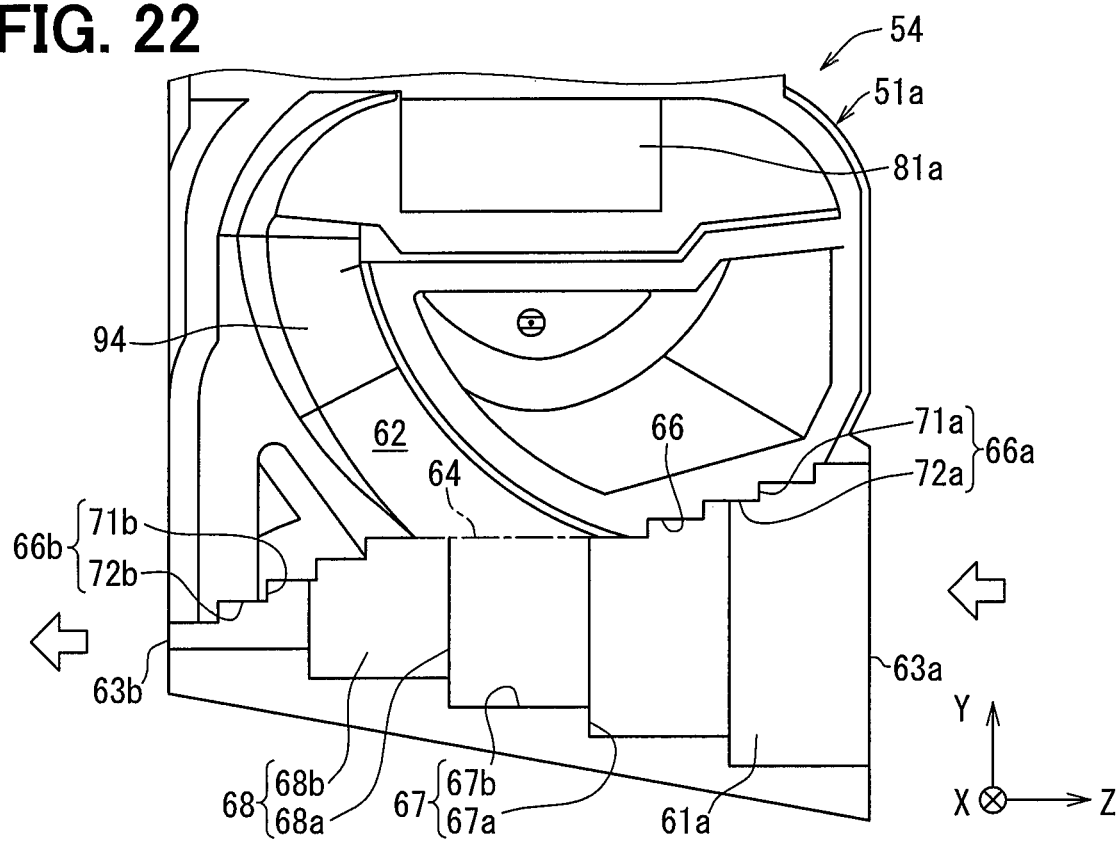
FIG. 22 is a diagram of the periphery of a passage flow channel in a modification B11.

As a modification B11, the passage wall surface 68 may have steps. For example, as shown in FIG. 22, the passage wall surface 68 has wall step surfaces 68a and wall connection surfaces 68b. The wall step surfaces 68a are orthogonal to the depth direction Z in the same manner as the bottom step surfaces 67a of the modification B10 described above and are aligned in the depth direction Z at predetermined intervals. An installation interval of the wall step surfaces 68a is larger than the depth interval Da of the inflow step surfaces 71a and the depth interval Db of the outflow step surfaces 71b, and is, for example, the same as the installation interval of the bottom step surfaces 67a. Specifically, the wall step surfaces 68a and the bottom step surfaces 67a are connected to each other. The wall connection surfaces 68b extend in parallel to the depth direction Z, similarly to the bottom connection surfaces 67b of the modification B10, and connect the adjacent wall step surfaces 68a. The wall step surfaces 68a and the wall connection surfaces 68b are formed on at least one of the pair of passage wall surfaces 68.

As a modification B12, the depth interval Da of the inflow step surfaces 71a may not be larger than the depth interval Db of the outflow step surfaces 71b. For example, the depth interval Da may be the same as or smaller than the depth interval Db.

As a modification B13, the inflow step surfaces 71a may be provided in the inflow ceiling surface portion 66a and the outflow ceiling surface portion 66b one by one. The inflow step surfaces 71a may be provided on only one of the inflow ceiling surface portion 66a and the outflow ceiling surface portion 66b.

Third Embodiment

An air flow meter 50 according to a third embodiment has a parallel region extending linearly in parallel with the depth direction Z. In the present embodiment, differences from the second embodiment will be mainly described.

Figure 23:
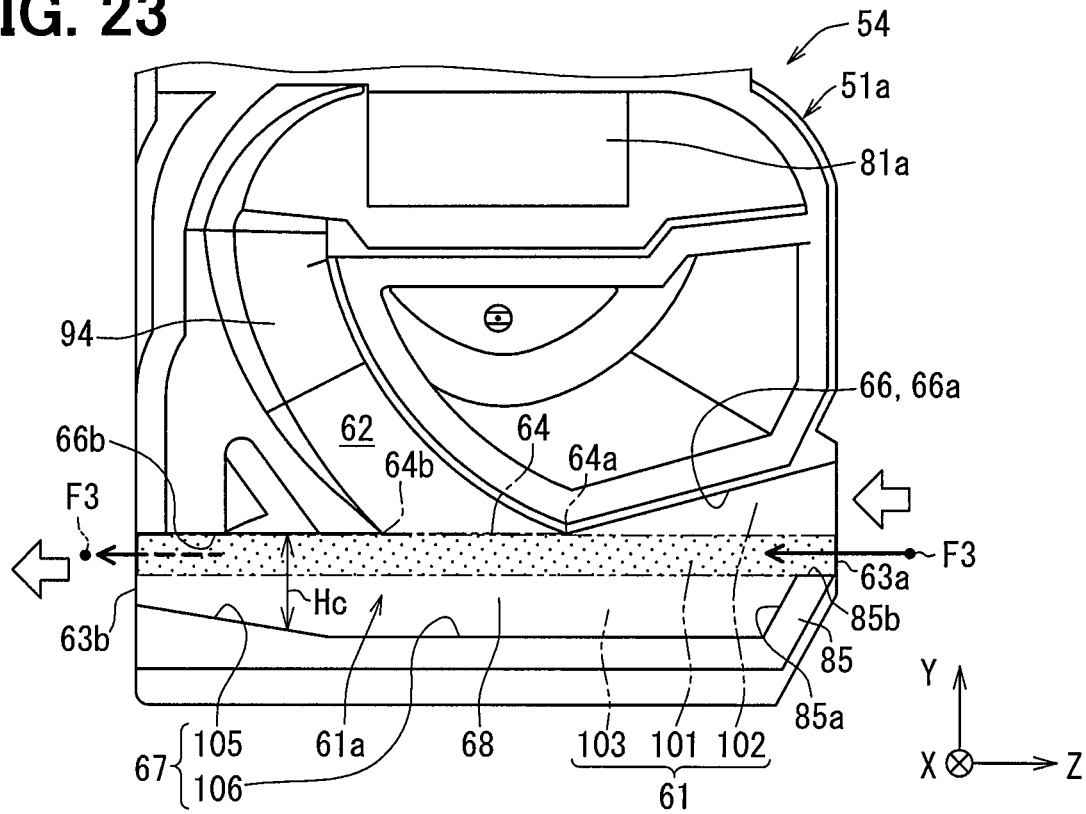
FIG. 23 is a diagram of the periphery of a passage flow channel according to a third embodiment.
Figure 24:
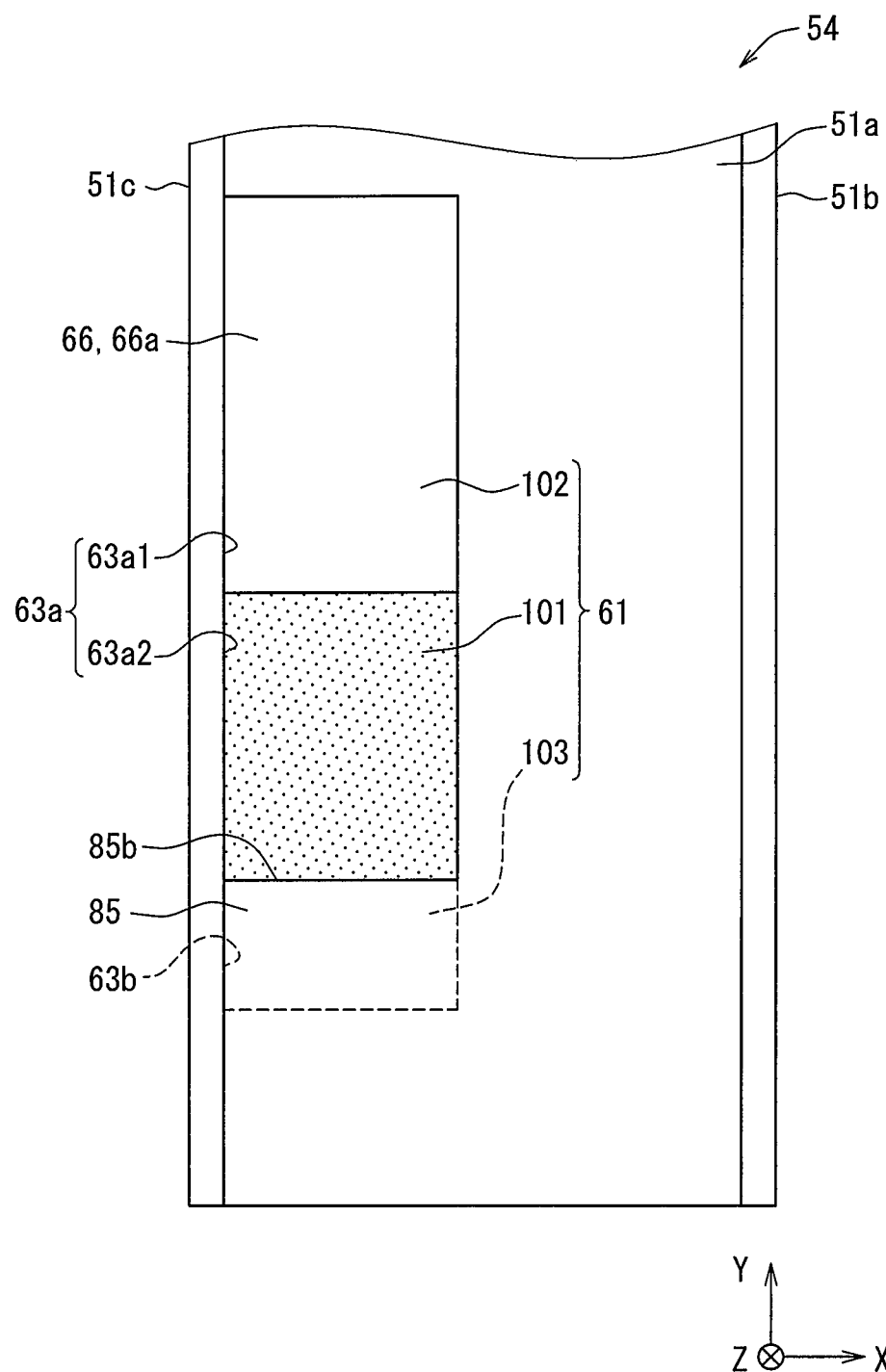
FIG. 24 is a diagram of the vicinity of an inflow port of an air flow meter as viewed from an upstream side.
Figure 25:
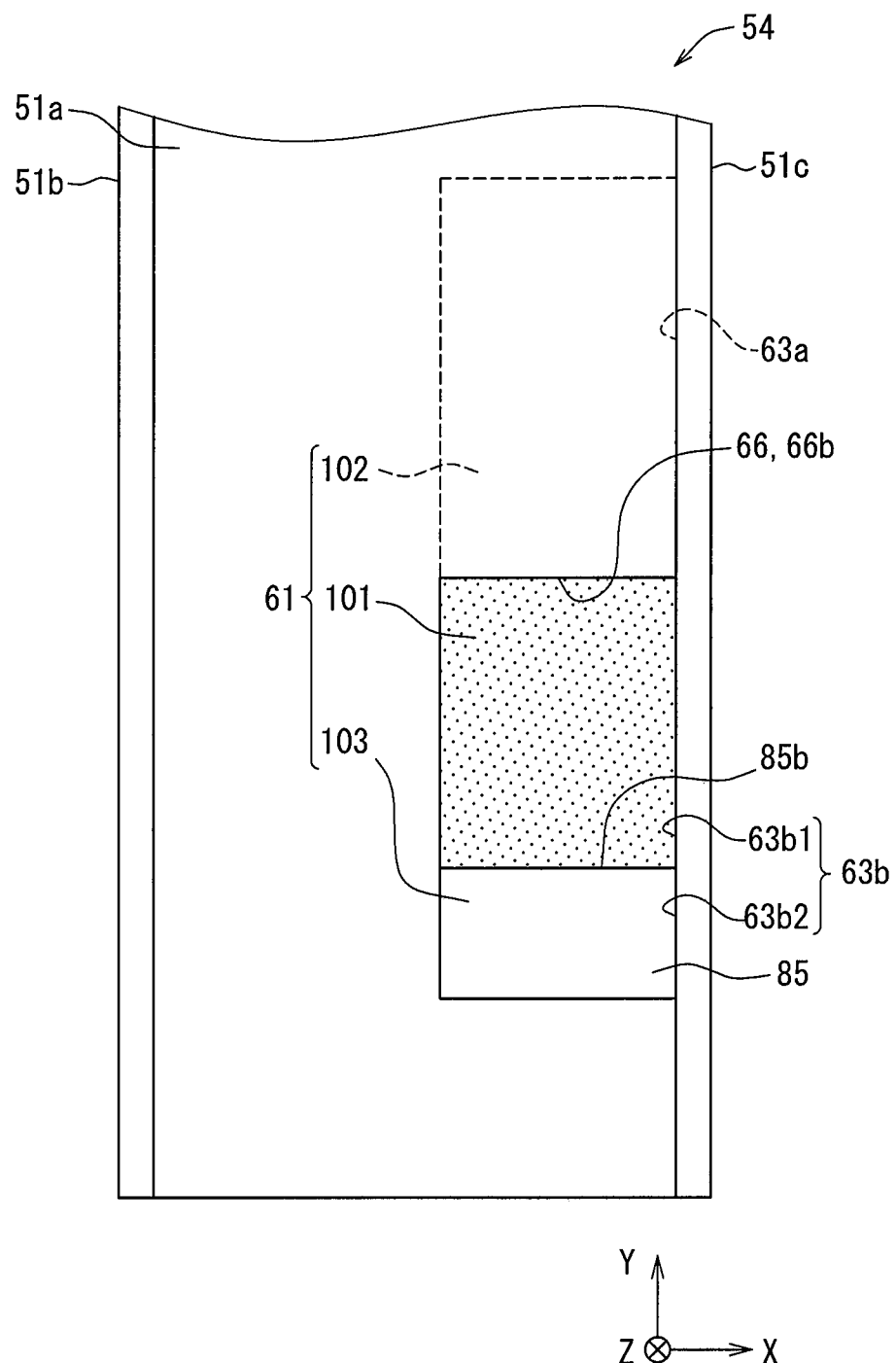
FIG. 25 is a diagram of the vicinity of an outflow port of the air flow meter as viewed from a downstream side.

As shown in FIG. 23, a passage flow channel 61 has a parallel region 101, a ceiling-side region 102, and a hidden region 103. The parallel region 101 is a region extending linearly in the depth direction Z so as to connect an inflow port 63a and an outflow port 63b, and an upstream end portion of the parallel region 101 is included in the inflow port 63a and a downstream end portion is included in the outflow port 63b. The ceiling-side region 102 is a region closer to a ceiling than the parallel region 101 in the height direction Y, and extends from the inflow port 63a toward a downstream side. In that case, an upstream end portion of the ceiling-side region 102 is included in the inflow port 63a. The hidden region 103 is a region located closer to a passage bottom surface 67 side (hereinafter, also referred to as a bottom side) than the parallel region 101 in the height direction Y, and extends from the outflow port 63b to the upstream side. In that case, a downstream end portion of the hidden region 103 is included in the outflow port 63b. All of the regions 101 to 103 are virtual regions, and the passage flow channel 61 is not actually divided into the regions 101 to 103. In FIGS. 23 to 25, the parallel region 101 is illustrated by dot hatching.

As shown in FIGS. 23 and 24, the inflow port 63a has a first entrance region 63a1 included in the parallel region 101 and a second entrance region 63a2 included in the ceiling-side region 102. In the inflow port 63a, the first entrance region 63a1 is disposed on a flange tip side of the second entrance region 63a2, and those regions 63a1 and 63a2 are aligned in the height direction Y so as to divide the inflow port 63a into two. The parallel region 101 is a region in which the first entrance region 63a1 is projected toward the downstream side, and the projection region reaches the outflow port 63b. On the other hand, since the ceiling-side region 102 gradually comes closer to the passage bottom surface 67 as the inflow ceiling surface portion 66a comes closer to a flow channel boundary portion 64, the ceiling-side region 102 is blocked by the inflow ceiling surface portion 66a from extending downstream in the depth direction Z. In this case, the ceiling-side region 102 is disposed on the upstream side of the inflow ceiling surface portion 66a.

As shown in FIGS. 23 and 25, the outflow port 63b has a first exit region 63b1 included in the parallel region 101 and a second exit region 63b2 included in the hidden region 103. In the outflow port 63b, the first exit region 63b1 is disposed closer to a base end side of the flange than the second exit region 63b2, and the regions 63b1 and 63b2 are aligned in the height direction Y so as to divide the outflow port 63b into two. The parallel region 101 may be referred to as a region in which the first exit region 63b1 is projected toward the upstream side. On the other hand, although the hidden region 103 extends upstream along the passage bottom surface 67, the hidden region 103 is blocked by the inflow restriction portion 85 from extending upstream in the depth direction Z due to the protrusion of the inflow restriction portion 85 from the passage bottom surface 67. In that case, the hidden region 103 is disposed on the downstream side of the inflow restriction portion 85, and is in a state of being hidden from the upstream side by the inflow restriction portion 85.

As shown in FIG. 23, an inner peripheral surface 61a of the passage flow channel 61 has a height narrowing surface 105. The height narrowing surface 105 is included in the passage bottom surface 67 and extends parallel to the width direction X over a pair of passage wall surfaces 68. The height narrowing surface 105 is disposed closer to the outflow port 63b than the flow channel boundary portion 64 in the depth direction Z, and extends from the outflow port 63b toward the upstream side. The height narrowing surface 105 gradually decreases a height dimension Hc of the passage flow channel 61 as the height narrowing surface 105 comes closer to the outflow port 63b.

The height narrowing surface 105 gradually comes closer to the passage ceiling surface 66 as the height narrowing surface 105 comes closer to the outflow port 63b, and continuously restricts the passage flow channel 61. In the width direction X, the width dimension of the passage flow channel 61 is uniform. As the height dimension Hc of the passage flow channel 61 gradually decreases toward the outflow port 63b, and the cross-sectional area of the passage flow channel 61 also gradually decreases. In that case, both the height dimension Hc and the cross-sectional area are smallest at the outflow port 63b on the downstream side of the flow channel boundary portion 64 in the passage flow channel 61.

The height dimension of the parallel region 101 remains constant in any part in the depth direction Z. On the other hand, the height dimension of the ceiling-side region 102 gradually decreases as the distance from the inflow port 63a increases. In this example, the passage bottom surface 67 has, in addition to the height narrowing surface 105, a parallel bottom surface portion 106 extending in parallel with the depth direction Z, and the parallel bottom surface portion 106 extends from the upstream end portion of the height narrowing surface 105 toward the upstream side. In that case, the height dimension of the hidden region 103 is constant for any portion of the area where the parallel bottom surface portion 106 is located, but gradually decreases toward the outflow port 63b as the area where the height narrowing surface 105 is located. In the inflow port 63a, the height dimension of the parallel region 101 is smaller than the height dimension of the ceiling-side region 102. In other words, the height dimension of the first entrance region 63a1 is smaller than the height dimension of the second entrance region 63a2. In that case, the second entrance region 63a2 and the ceiling-side region 102 inhibits the insufficiency of the inflow amount of the intake air into the passage flow channel 61 while securing the parallel region 101. In the outflow port 63b, the height dimension of the parallel region 101 is smaller than the height dimension of the hidden region 103. In other words, the height dimension of the first exit region 63b1 is larger than the height dimension of the second exit region 63b2. In that case, since the parallel region 101 is secured as large as possible at the outflow port 63b, the foreign matter traveling linearly through the parallel region 101 is easily discharged from the outflow port 63b as it is.

The height narrowing surface 105 is disposed on the downstream side of the inflow restriction portion 85 in the depth direction Z, and is hidden from the upstream side by the inflow restriction portion 85. For that reason, in the depth direction Z, the height narrowing surface 105 is not exposed to the upstream side from the inflow port 63a due to the presence of the inflow restriction portion 85. For example, when a person looks into the passage flow channel 61 through the inflow port 63a in the depth direction Z, the height narrowing surface 105 cannot be visually recognized because the sight line is blocked by the inflow restriction portion 85. However, in a direction angled with respect to the depth direction Z, the height narrowing surface 105 may be exposed from the inflow port 63a, and a person looking into the depth side of the inflow restriction portion 85 can visually recognize the height narrowing surface 105 from that direction.

For example, when a large foreign matter F3 traveling linearly in the depth direction Z enters the passage flow channel 61 from the first entrance region 63a1 of the inflow port 63a, the large foreign matter F3 simply travels linearly in the parallel region 101 and exits from the first exit region 63b1 of the outflow port 63b. For that reason, even if the passage flow channel 61 is narrowed by the height narrowing surface 105, the large foreign matter F3 traveling linearly in the depth direction Z that travels linearly in the parallel region 101 does not easily collide with the height narrowing surface 105 or enter the measurement flow channel 62.

Figure 26:
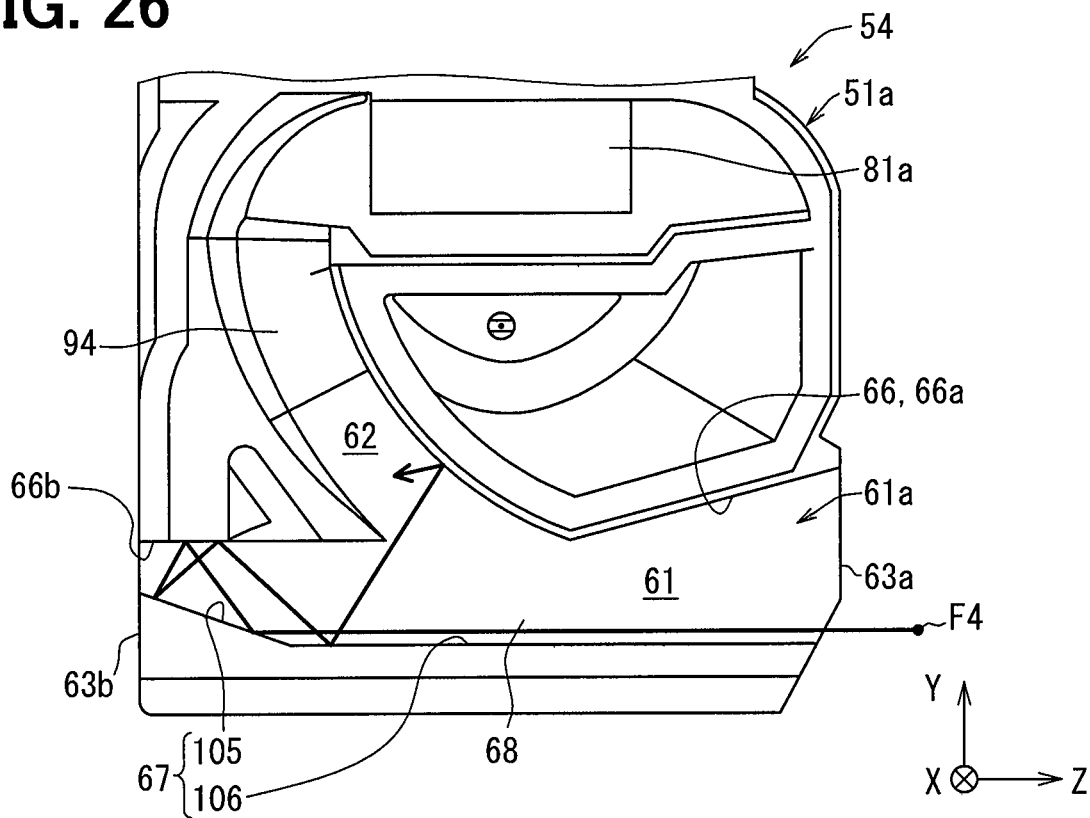
FIG. 26 is a diagram illustrating a configuration in which the air flow meter has no inflow restriction portion, unlike the third embodiment.

On the other hand, unlike the present embodiment, in the configuration in which the height narrowing surface 105 is exposed to the upstream side from the inflow port 63a in the depth direction Z, there is a concern that foreign matter will collide with the height narrowing surface 105 and rebounds, thereby easily entering the measurement flow channel 32. For example, as shown in FIG. 26, in the configuration in which the height narrowing surface 105 is exposed to the upstream side from the inflow port 63a in the depth direction Z with no provision of the inflow restriction portion 85, it is assumed that a large foreign matter F4 traveling linearly in the depth direction Z collides with the height narrowing surface 105. In that case, depending on the angle at which the large foreign matter F4 rebounds at the height narrowing surface 105, the large foreign matter F4 may easily enter the measurement flow channel 62 while the large foreign matter F4 rebounds at the outflow ceiling surface portion 66b following the height narrowing surface 105 and advances toward the upstream side. As described above, when the traveling direction of the large foreign matter F4 rebounded at the height narrowing surface 105 changes with respect to the height direction Y, the possibility that the large foreign matter F4 enters the measurement flow channel 62 is likely to be increased. In that regard, in the present embodiment, since the large foreign matter F4 that has traveled linearly in the depth direction Z is configured to hardly collide with the height narrowing surface 105, the large foreign matter F4 is inhibited from entering the measurement flow channel 62.

In the present embodiment, the outflow ceiling surface portion 66b and the flow channel boundary portion 64 extend parallel to the depth direction Z, and the upstream end portion of the measurement flow channel 62 is opened to the flange tip side in the height direction Y. In that case, the upstream end portion of the measurement flow channel 62 is not opened toward either the inflow port 63a or the outflow port 63b. The parallel region 101 extends in parallel with the flow channel boundary portion 64, and the outflow ceiling surface portion 66b and the flow channel boundary portion 64 define a ceiling-side range of the parallel region 101. Because the flow channel boundary portion 64 extends in parallel with the depth direction Z, the flow channel boundary portion 64 is not exposed to the upstream side from the inflow port 63a. For that reason, for example, the large foreign matter F3 traveling linearly in the depth direction Z in the parallel region 101 does not easily enter the measurement flow channel 62 without changing the traveling direction. The parallel region 101 extends in parallel with the upper surface 85b of the inflow restriction portion 85, and the upper surface 85b defines a bottom side range of the parallel region 101.

According to the present embodiment described so far, since the height narrowing surface 105 is not exposed to the upstream side from the inflow port 63a in the depth direction Z while reserving the parallel region 101 in the passage flow channel 61, a configuration in which the foreign matter is less likely to collide with the height narrowing surface 105 can be realized. This makes it possible to inhibit that the foreign matter entering the passage flow channel 61 through the inflow port 63a and traveling linearly collides with the height narrowing surface 105 and rebounds to return to the upstream side and enter the measurement flow channel 62, despite passing through the flow channel boundary portion 64.

In the passage flow channel 61, the parallel region 101 is reserved as a projection region of the first entrance region 63a1 of the inflow port 63a. For that reason, the foreign matter that travels linearly in the depth direction Z in the parallel region 101 tends to exit from the outflow port 63b without colliding with any portion of the inner peripheral surface 61a of the passage flow channel 61. As described above, for example, as compared with the configuration in which the region extending linearly in the depth direction Z is not secured in the passage flow channel 61, the possibility that the foreign matter collides with the inner peripheral surface 61a of the passage flow channel 61 is reduced, thereby being capable of reducing the entry of the foreign matter into the measurement flow channel 62.

In addition, since the height narrowing surface 105 reduces the passage flow channel 61 on the downstream side of the flow channel boundary portion 64, the amount of intake air flowing from the passage flow channel 61 into the measurement flow channel 62 is likely to increase. In this example, because the flow rate detection unit 52 is a thermal type flow rate sensor, it is preferable that a flow rate of the intake air in the measurement flow channel 62 is high to some extent in order to properly maintain the detection accuracy of the flow rate detection unit 52. In other words, it is preferable that the flow rate of the intake air from the passage flow channel 61 to the measurement flow channel 62 is somewhat high. The inflow amount into the measurement flow channel 62 increases or decreases in accordance with a relationship between the cross-sectional area and the flow channel length of the passage flow channel 61 and the measurement flow channel 62, and it is conceivable that the inflow amount increases as a minimum cross-sectional area in the passage flow channel 61 decreases. On the other hand, according to the present embodiment, since the minimum cross-sectional area of the passage flow channel 61 is reduced by the amount corresponding to the provision of the height narrowing surface 105, the inflow amount into the measurement flow channel 62 is increased as compared with the configuration in which the height narrowing surface 105 is not provided. This makes it possible to optimize the detection accuracy of the flow rate detection unit 52 in the measurement flow channel 62.

According to the present embodiment, since the flow channel boundary portion 64 is not exposed to the upstream side from the inflow port 63a in the depth direction Z, the foreign matter entering from the inflow port 63a can be inhibited from directly entering the measurement flow channel 62 without colliding with the inner peripheral surface 61a of the passage flow channel 61. This makes it possible to exert a deterrent force against lowering of the detection accuracy of the flow rate detection unit 52 due to the foreign matter adhering to the flow rate detection unit 52 or the like.

According to the present embodiment, since the height narrowing surface 105 is an inclined surface, the height dimension Hc and the cross-sectional area of the passage flow channel 61 are gradually reduced. For that reason, as compared with a configuration in which the height dimension Hc and the cross-sectional area of the passage flow channel 61 are rapidly reduced, for example, turbulence of an air flow is less likely to occur in the periphery of the height narrowing surface 105. In that case, since the turbulence is less likely to occur also in the intake air flowing into the measurement flow channel 62, the detection accuracy of the flow rate detection unit 52 can be inhibited from being lowered due to the turbulence in the air flow generated in the measurement flow channel 62.

According to the present embodiment, the passage bottom surface 67 has the parallel bottom surface portion 106 extending parallel to the parallel region 101. In that case, for example, the flow of the intake air in the parallel region 101 is less likely to be disturbed as compared with a configuration in which the passage bottom surface 67 does not have a portion extending in parallel with the parallel region 101. For that reason, the parallel bottom surface portion 106 can urge the foreign matter that travels linearly in the depth direction Z in the parallel region 101 to exit from the outflow port 63b as it is.

According to the present embodiment, since the inflow restriction portion 85 is simply provided so as to cover and hide the height narrowing surface 105 from the upstream side, the foreign matter traveling linearly in the depth direction Z is less likely to collide with the height narrowing surface 105. For example, unlike the present embodiment, when the height narrowing surface 105 is hidden on the downstream side of the inflow ceiling surface portion 66a, there is a concern that a large number of considerations such as the position of the flow channel boundary portion 64 and the branching angle of the measurement flow channel 62 with respect to the passage flow channel 61 occur in the stage of design change. On the other hand, in the method of providing the inflow restriction portion 85, although there is a need to optimize the inflow amount from the inflow port 63a at the stage of design change, it is considered that a design load is relatively easily reduced.

According to the present embodiment, the whole of the outflow port 63b is not included in the parallel region 101, but the first exit region 63b1 of the outflow port 63b is included in the parallel region 101, while the second exit region 63b2 is not included in the parallel region 101. For that reason, for example, when the turbulence of the air flow occurs in the passage flow channel 61, the possibility that the turbulence is included not in the parallel region 101 but in the hidden region 103, for example, can be ensured. In other words, the possibility that the turbulence or the like of the air flow is discharged to the outside from the second exit region 63b2 instead of the first exit region 63b1. This makes it possible to inhibit a state in which the foreign matter does not easily travel linearly in the depth direction Z in the parallel region 101 due to the turbulence of the air flow or the like.

The third embodiment can be applied to various embodiments and combinations without departing from the spirit of the present disclosure.

Figure 27:
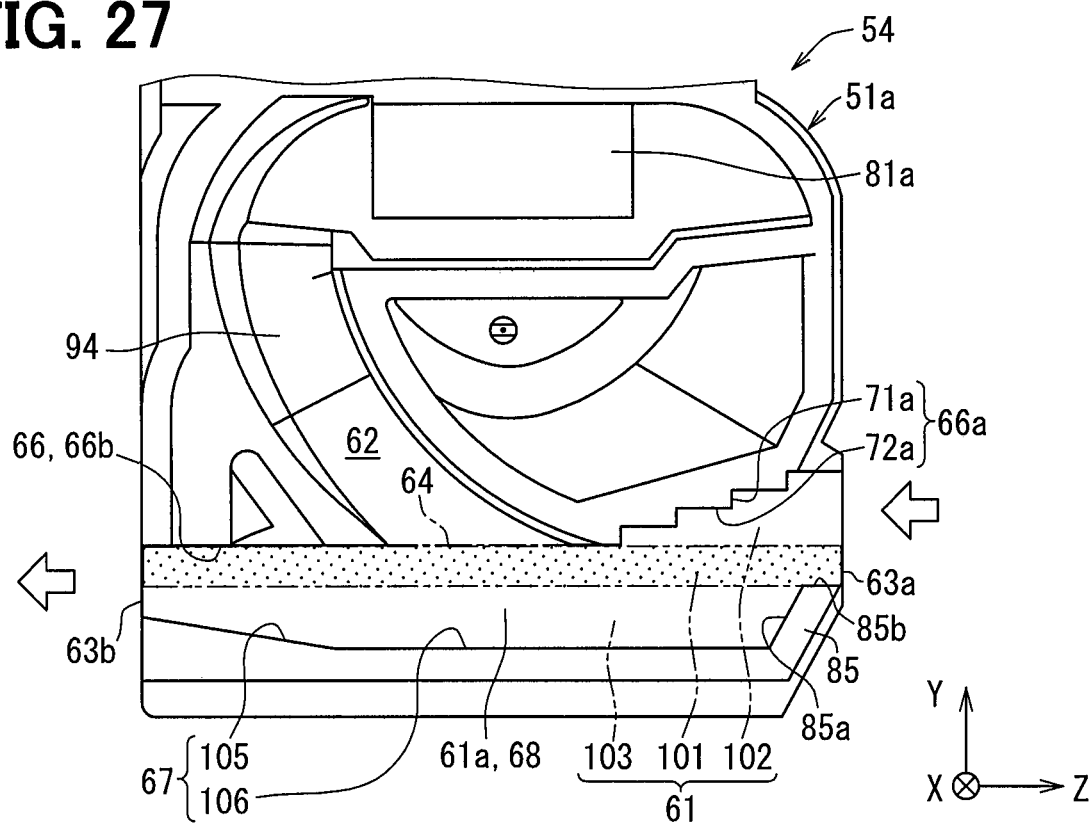
FIG. 27 is a diagram of the periphery of a passage flow channel in a modification C1.

As a modification C1, the inflow ceiling surface portion 66a may have steps. For example, the second embodiment is applied, and as shown in FIG. 27, the inflow ceiling surface portion 66a has an inflow step surface 71a and an inflow connection surface 72a. Also in the above configuration, the ceiling-side region 102 is formed between the inflow ceiling surface portion 66a and the parallel region 101. In the above configuration, when a foreign matter traveling linearly in the depth direction Z enters the ceiling-side region 102, the foreign matter collides with the inflow step surface 71a and rebounds to the inflow port 63a side, thereby inhibiting the entry of the foreign matter into the measurement flow channel 62.

Figure 28:
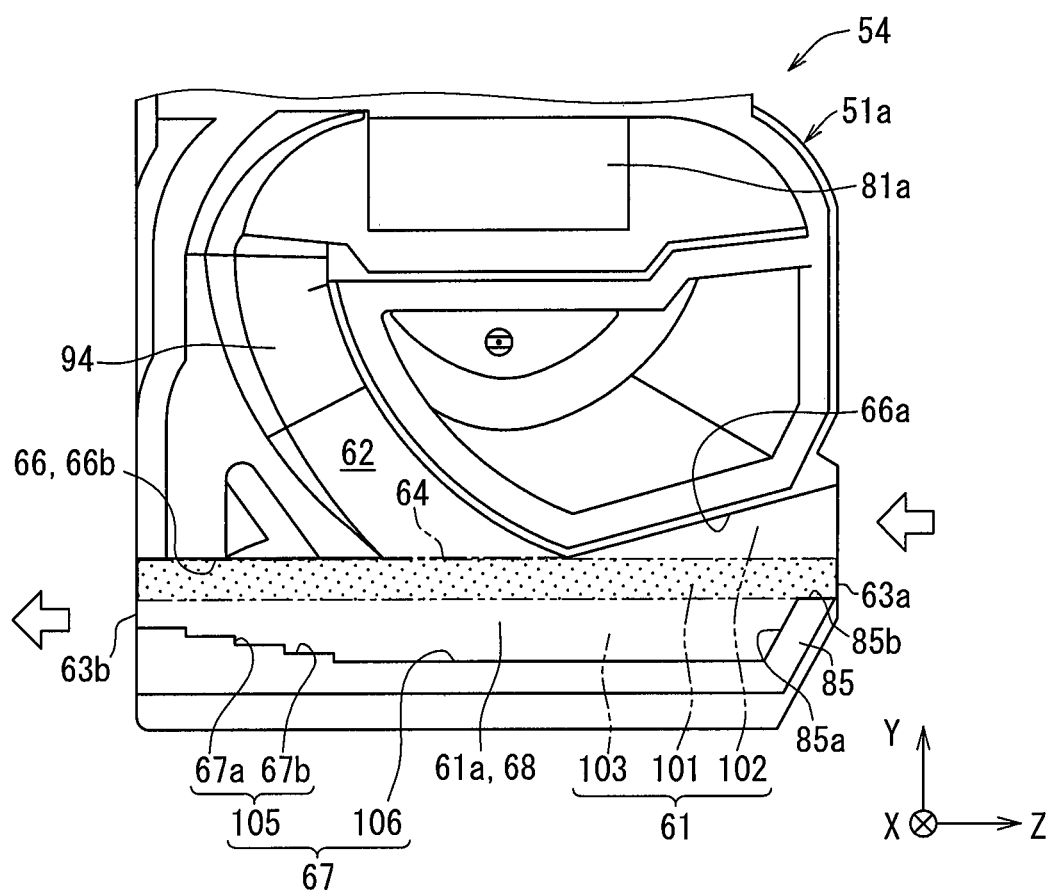
FIG. 28 is a diagram of the periphery of a passage flow channel in a modification C2.

As a modification example C2, the height narrowing surface 105 may have steps. For example, the modification B10 is applied, and as shown in FIG. 28, the height narrowing surface 105 has bottom step surfaces 67a and bottom connection surfaces 67b. The height narrowing surface 105 with the above configuration does not continuously narrows the passage flow channel 61 while coming closer to the outflow port 63b, but narrows the passage flow channel 61 in a stepwise manner. In the above configuration, the height dimension Hc and the cross-sectional area of the passage flow channel 61 are gradually reduced toward the outflow port 63b. In this example, a downstream end portion of the bottom connection surface 67b disposed on the most downstream side is included in the outflow port 63b, and the height dimension Hc and the cross-sectional area of the portion formed by the bottom connection surface 67b are the smallest in the passage flow channel 61.

Figure 29:
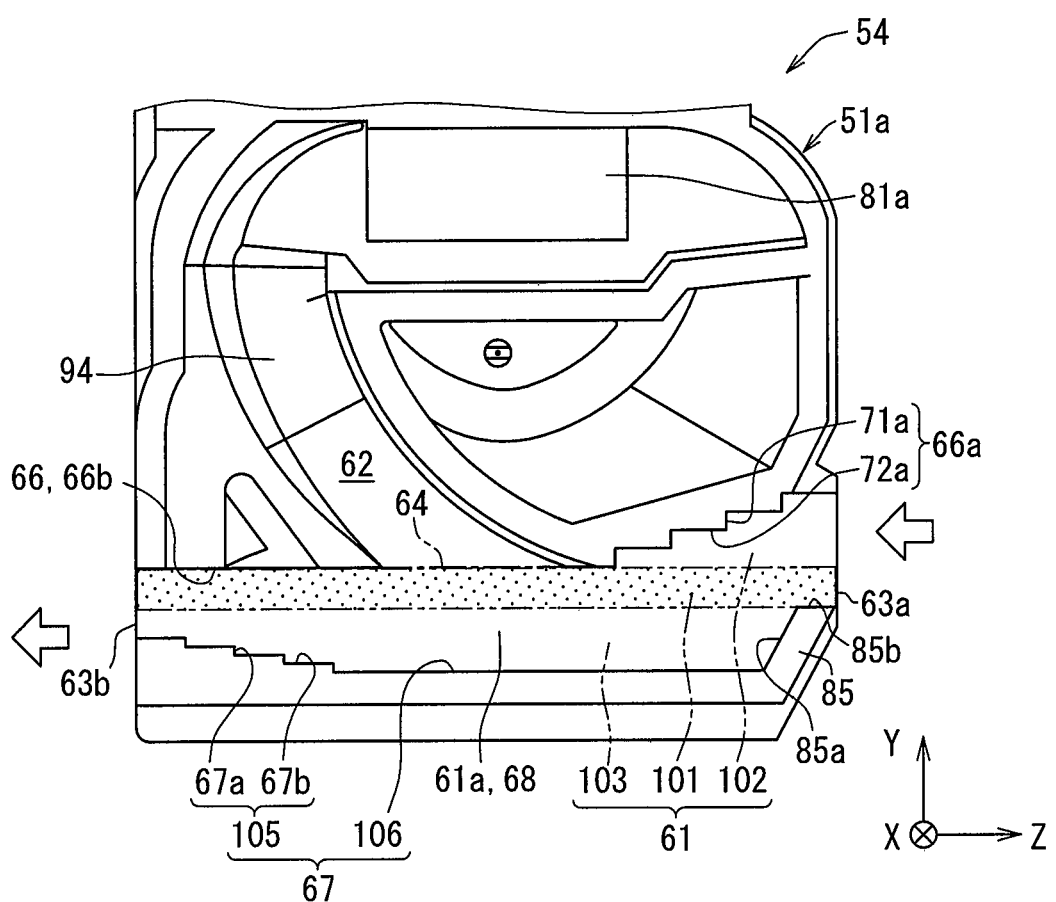
FIG. 29 is a diagram of the periphery of a passage flow channel in a modification C3.

As a modification C3, both the inflow ceiling surface portion 66a and the height narrowing surface 105 may have steps by combining the modification C1 and the modification C2 together. For example, as shown in FIG. 29, the inflow ceiling surface portion 66a has an inflow step surface 71a and an inflow connection surface 72a, and the height narrowing surface 105 has a bottom step surface 67a and a bottom connection surface 67b.

Figure 30:
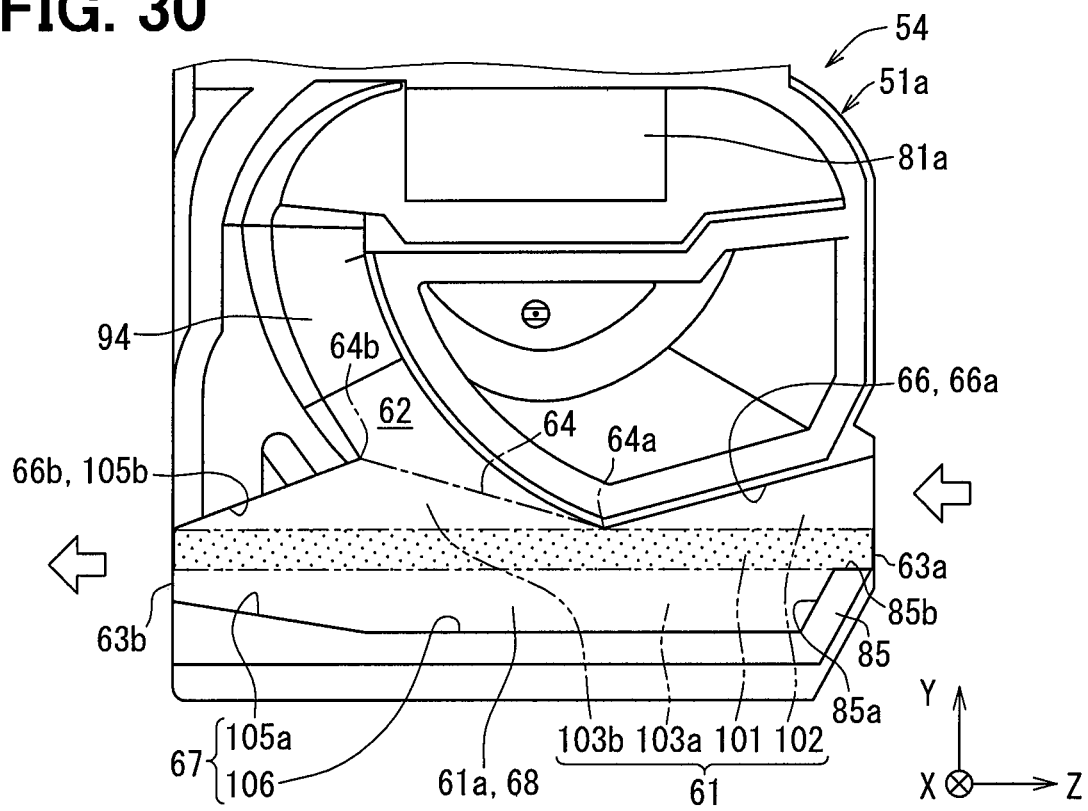
FIG. 30 is a diagram of the periphery of a passage flow channel in modifications C4 and C5.

As a modification C4, the inner peripheral surface 61a of the passage flow channel 61 may have multiple height narrowing surfaces. For example, as shown in FIG. 30, the inner peripheral surface 61a has a bottom restriction surface 105a and a ceiling restriction surface 105b as height narrowing surfaces. The bottom restriction surface 105a is the height narrowing surface 105 of the third embodiment, and is included in the passage bottom surface 67. The ceiling restriction surface 105b is included in the outflow ceiling surface portion 66b, and extends over the pair of passage wall surfaces 68 in the same manner as the bottom restriction surface 105a. A downstream end portion of the ceiling restriction surface 105b is included in the outflow port 63b, and the ceiling restriction surface 105b gradually comes closer to the passage bottom surface 67 as the ceiling restriction surface 105b comes closer to the outflow port 63b in the height direction Y. In addition, almost the whole of the outflow ceiling surface portion 66b is the ceiling restriction surface 105b. In the above configuration, since both the bottom restriction surface 105a and the ceiling restriction surface 105b narrow the passage flow channel 61, the degree of narrowing the passage flow channel 61 can be set to be as large as possible.

Figure 31:
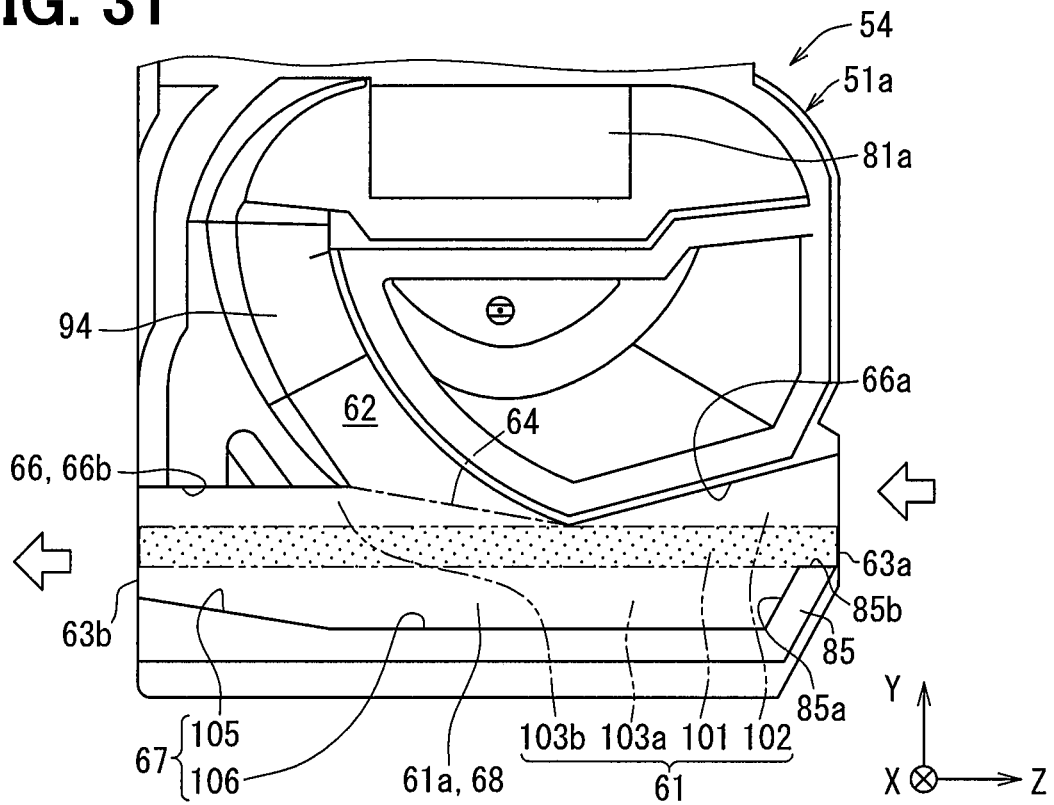
FIG. 31 is a diagram of the periphery of the passage flow channel in the modification C5.

As a modification C5, the passage flow channel 61 may have a plurality of hidden regions. For example, as shown in FIG. 30 and FIG. 31, the passage flow channel 61 is configured to have a bottom hidden region 103a and a ceiling hidden region 103b as hiding regions. The bottom hidden region 103a is the hidden region 103 of the third embodiment, and is formed between the parallel region 101 and the passage bottom surface 67. The ceiling hidden region 103b is a region formed between the parallel region 101 and the outflow ceiling surface portion 66b.

For example, as shown in FIG. 31, the ceiling hidden region 103b may extend from the outflow port 63b toward the downstream side. In the above configuration, the outflow port 63b has multiple second exit regions 63b2, the bottom hidden region 103a extends from the second exit regions 63b2 on the bottom side, and the ceiling hidden region 103b extends from the second exit regions 63b2 on the ceiling-side toward the upstream side. The ceiling hidden region 103b is disposed on the downstream side of the inflow ceiling surface portion 66a in the depth direction Z, and is in a state of being hidden from the upstream side by the inflow ceiling surface portion 66a.

The ceiling hidden region 103b may be formed independently of the outflow port 63b, as shown in FIG. 31, for example. In the above configuration, as compared with the third embodiment, the downstream boundary portion 64b of the flow channel boundary portion 64 is disposed at a position away from the passage bottom surface 67. In that case, the flow channel boundary portion 64 does not extend in parallel to the depth direction Z, but extends obliquely to the bottom side toward the downstream side, thereby being inclined with respect to the depth direction Z. In this example, the upstream end portion of the ceiling restriction surface 105b is included in the outflow port 63b. As a result, the passage flow channel 61 is shaped such that a portion around the downstream boundary portion 64b expands toward a side opposite to the passage bottom surface 67, and that portion is the ceiling hidden region 103b. The ceiling hidden region 103b is a region surrounded by the ceiling restriction surface 105b, the flow channel boundary portion 64, and the parallel region 101.

Figure 32:
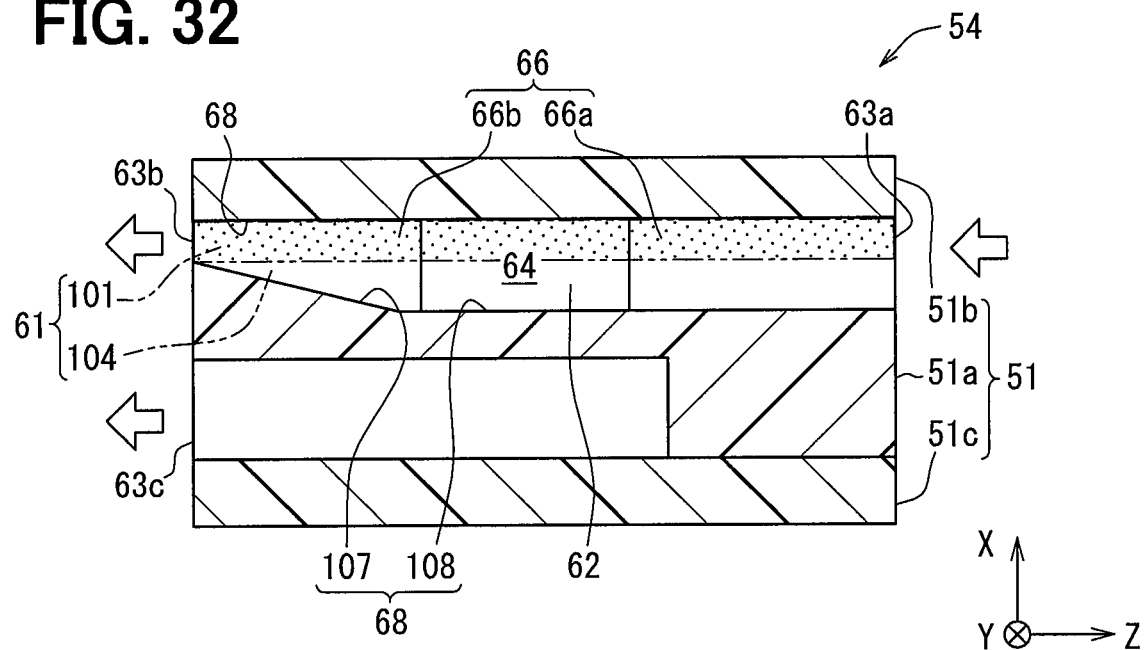
FIG. 32 is a cross-sectional view of a passage flow channel as viewed from a bottom side toward a ceiling side in a direction orthogonal to a height direction in a modification C6.

As a modification C6, the inner peripheral surface 61a of the passage flow channel 61 may have a width narrowing surface that narrows the passage flow channel 61 in the width direction as a distance from the outflow port 63b decreases. Specifically, at least one of the pair of passage wall surfaces 68 may include the width narrowing surface. For example, as shown in FIG. 32, one of the pair of passage wall surfaces 68 includes a width narrowing surface 107. The width narrowing surface 107 extends in parallel to the height direction Y in a state where the width narrowing surface 107 extends over the outflow ceiling surface portion 66b and the passage bottom surface 67. The width narrowing surface 107 is disposed closer to the outflow port 63b than the flow channel boundary portion 64 in the depth direction Z, and extends from the outflow port 63b toward the upstream side. The width narrowing surface 107 gradually decreases the width dimension Wa of the passage flow channel 61 as the width narrowing surface 107 comes closer to the outflow port 63b. The width narrowing surface 107 comes gradually closer to the other passage wall surface 68 as the width narrowing surface 107 comes closer to the outflow port 63b, and continuously reduces the width dimension Wa and the cross-sectional area of the passage flow channel 61.

The parallel region 101 is a region between the width narrowing surface 107 and the passage wall surface 68 without the width narrowing surface 107 in the width direction X. The passage flow channel 61 has, in addition to the parallel region 101, a side region 104 provided on the side of the parallel region 101 in the width direction X. The side region 104 is a region extending from the inflow port 63a toward the downstream side, and is disposed on the upstream side of the width narrowing surface 107. In the above configuration, it is considered that the foreign matter that has entered the side region 104 from the inflow port 63a travels linearly in the depth direction Z to rebound at the width narrowing surface 107, but it is considered that the traveling direction of the foreign matter is likely to change in the width direction X in the rebound, but is less likely to change in the height direction Y. For that reason, it is difficult for the foreign matter to easily enter the measurement flow channel 62 due to collision with the width narrowing surface 107.

The passage wall surface 68 having the width narrowing surface 107 has a parallel wall surface portion 108 extending parallel to the depth direction Z. The parallel wall surface portion 108 extends from the upstream end portion of the width narrowing surface 107 toward the upstream side, and the upstream end portion of the parallel wall surface portion 108 is included in the inflow port 63a. As a result, the parallel wall surface portion 108 prompts the foreign matter that travels linearly in the depth direction Z in the parallel region 101 to move linearly as it is and exit from the outflow port 63b.

The width narrowing surface 107 may have steps instead of an inclined surface. For example, similarly to the passage ceiling surface 66 of the second embodiment, the width narrowing surface 107 has a step surface and a connection surface.

As a modification C7, a portion with the lowest height dimension Hc or the lowest cross-sectional area in the passage flow channel 61 may not be the outflow port 63b. For example, the portion may be an intermediate portion between the flow channel boundary portion 64 and the outflow port 63b in the depth direction Z. Even in that case, if the height narrowing surface 105 is configured to narrow the passage flow channel 61, a flow of the intake air in the measurement flow channel 62 can be appropriately accelerated.

As a modification C8, at least one of the inflow port 63a and the outflow port 63b may be entirely included in the parallel region 101. For example, the outflow port 63b is configured to have only the first outlet area 63b1 of the first exit region 63b1 and the second exit region 63b2.

As a modification C9, the downstream boundary portion 64b of the flow channel boundary portion 64 may be disposed on the bottom side of the upstream boundary portion 64a in the height direction Y. For example, the downstream boundary portion 64b is exposed to the upstream side from the inflow port 63a in the depth direction Z. Even in that configuration, if the outflow ceiling surface portion 66b extends in parallel with the depth direction Z, the configuration does not correspond to a configuration in which the outflow ceiling surface portion 66b narrows the passage flow channel 61 at a position exposed to the upstream side from the inflow port 63a in the depth direction Z.

As a modification C10, the passage bottom surface 67 may not have the parallel bottom surface portion 106. For example, it is assumed that substantially the whole of the passage bottom surface 67 is the height narrowing surface 105. In that configuration, the height narrowing surface 105 extends from the base end portion of the inflow restriction portion 85 toward the downstream side. In that case, the height narrowing surface 105 is in a state of being extended over the inflow restriction portion 85 and the outflow port 63b.

Fourth Embodiment

In an air flow meter 50 according to a fourth embodiment, a flow channel boundary portion 64 is not exposed to an upstream side through an inflow port 63a. In the present embodiment, similarly to the third embodiment, differences from the second embodiment will be mainly described.

Figure 33:
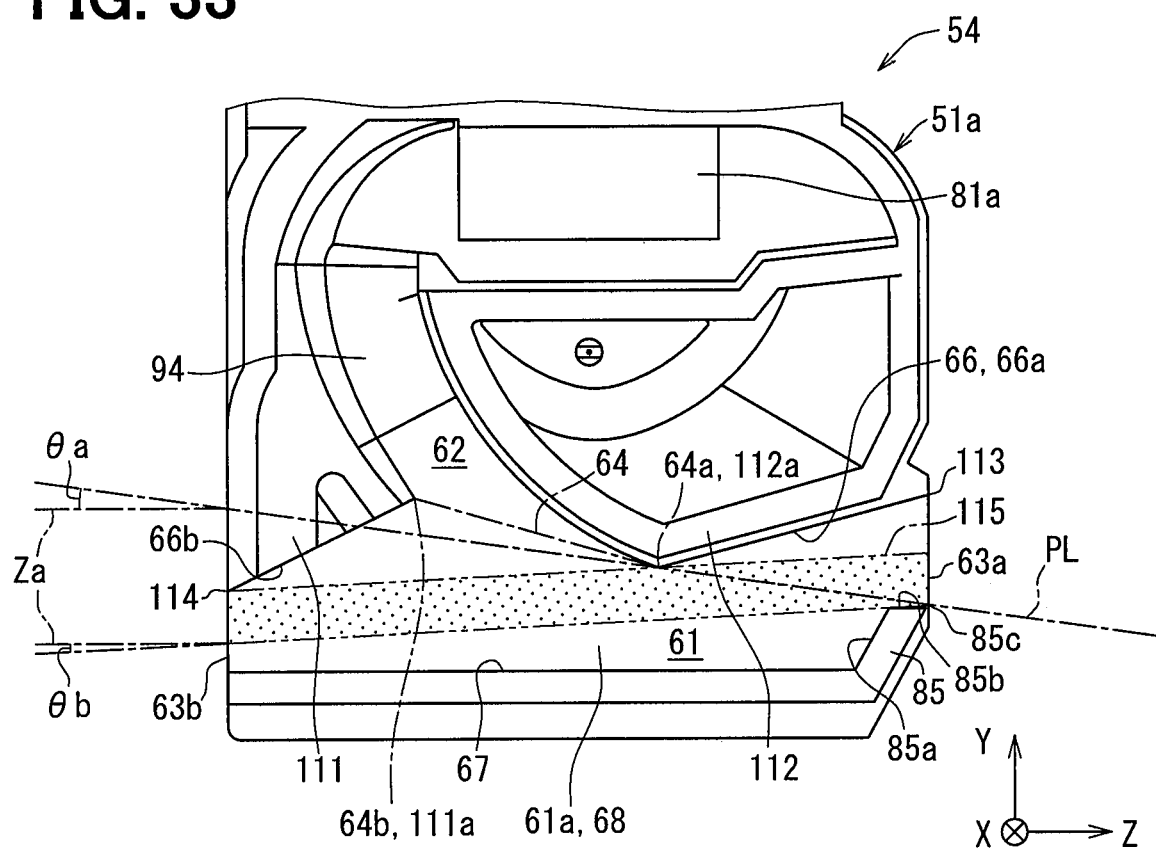
FIG. 33 is a diagram of the periphery of a passage flow channel according to a fourth embodiment.

As shown in FIG. 33, a flow channel forming portion 54 has a flow channel partition portion 111 that divides the passage path 61 to have a measurement flow channel 62 separate from a passage flow channel 61. The flow channel partition portion 111 is provided on the downstream side of the flow channel boundary portion 64 in the depth direction Z and on the opposite side of a passage bottom surface 67 across the passage flow channel 61 in the height direction Y. A partition top portion 111a, which is an upstream end portion of the flow channel partition portion 111, serves as a downstream boundary portion 64b of the flow channel boundary portion 64. In that case, the partition top portion 111a is located at the same position as that of the downstream boundary portion 64b. A height dimension of the flow channel partition portion 111 gradually decreases as the flow channel partition portion 111 comes closer to the flow channel boundary portion 64 in the depth direction Z, and the smallest portion of the height dimension is the partition top portion 111a. In that case, the partition top portion 111a is a top side extending in the width direction X. It can be conceivable that the flow channel partition portion 111 partitions the passage flow channel 61 and the measurement flow channel 62 vertically in the height direction Y.

The flow channel partition portion 111 is included in a housing main body 51a of a housing 51. In the flow channel partition portion 111, a surface facing the bottom side forms an outflow ceiling surface portion 66b, and the surface facing the opposite side to the passage bottom surface 67 forms an inner peripheral surface of the measurement flow channel 62.

The flow channel forming portion 54 has a ceiling projection portion 112 protruding toward the bottom side in addition to the flow channel partition portion 111. The ceiling projection portion 112 is provided on the upstream side of the outflow ceiling surface portion 66b. In the height direction Y, the ceiling top portion 112a, which is the bottom-side end portion of the ceiling projection portion 112, forms the upstream boundary portion 64a of the flow channel boundary portion 64. In that case, it can be conceivable that the ceiling top portion 112a is located at the same position as that of the upstream boundary portion 64a. A depth dimension of the ceiling projection portion 112 in the depth direction Z gradually decreases as the ceiling projection portion 112 comes closer to the passage bottom surface 67 in the height direction Y, and a portion having the smallest depth dimension becomes the ceiling top portion 112a. In that case, the ceiling top portion 112a is a top side extending in the width direction X.

The ceiling projection portion 112 is included in the housing main body 51a of the housing 51. In the ceiling projection portion 112, a surface facing the upstream side in the depth direction Z forms the inflow ceiling surface portion 66a, and the surface facing the downstream side forms the inner peripheral surface of the measurement flow channel 62.

In the present embodiment, the partition top portion 111a is not exposed to the upstream side through the inflow port 63a. For example, when a person looks into the passage flow channel 61 from the inflow port 63a, even if the direction of the looking-in is changed, the partition top portion 111a cannot be visually recognized. In other words, the partition top portion 111a is hidden from the upstream side by the inflow restriction portion 85 and the ceiling projection portion 112, and the sight line of the person from the inflow port 63a is blocked by the inflow restriction portion 85 and the ceiling projection portion 112. The fact that the partition top portion 111a is not exposed means that the flow channel boundary portion 64 is also not exposed to the upstream side from the inflow port 63a.

The inflow restriction portion 85 corresponds to a bottom projection portion protruding from the passage bottom surface 67 toward the ceiling side. The upper surface 85b of the inflow restriction portion 85 may be referred to as an upper end portion of the inflow restriction portion 85, and if the upstream end portion of the upper surface 85b is referred to as a restriction top portion 85c, the restriction top portion 85c is also included in the upper end portion of the inflow restriction portion 85.

In the passage flow channel 61, a virtual line connecting the restriction top portion 85c of the inflow restriction portion 85 and the ceiling top portion 112a of the ceiling projection portion 112 is referred to as a connecting line PL. The connecting line PL may also be referred to as a virtual line expressing the sight line that allows a person to see a portion close to the partition top portion 111a when looking into the passage flow channel 61 from the inflow port 63a, for example. In addition, for example, in a configuration in which the multiple ceiling projection portions and the multiple bottom projection portions are present on the upstream side of the flow channel boundary portion 64, a virtual line in which a connecting angle θa, which is an inclination angle with respect to the depth direction Z, has a maximum value, among the virtual lines connecting the tip portion of each ceiling projection portion and the tip portion of each bottom projection portion, is referred to as the connecting line PL.

When a virtual line extending in parallel with the depth direction Z is referred to as a depth reference line Za, the connecting angle θa is an angle of a portion facing toward the downstream side between the connecting line PL and the depth reference line Za. In that case, the connecting angle θa is a side in which the side where the downstream side portion of the connecting line PL is away from the passage bottom surface 67 increases with a positive value, and a side in which the side where the downstream side portion of the connecting line PL comes closer to the passage bottom surface 67 increases with a negative value. For that reason, as shown in FIG. 33, when the connecting line PL is inclined toward the downstream side so as to be away from the passage bottom surface 67, the connecting angle θa has the positive value. On the other hand, when the connecting line PL is inclined toward the downstream side so as to comes closer to the passage bottom surface 67, the connecting angle θa has the negative value.

The inner peripheral surface 61a of the passage flow channel 61 has an inflow upper end portion 113 and an outflow upper end portion 114. The inflow upper end portion 113 is an end portion of the inflow port 63a opposite to the passage bottom surface 67 in the height direction Y, and the outflow upper end portion 114 is an end portion of the outflow port 63b opposite to the passage bottom surface 67 in the height direction Y. The inflow upper end portion 113 is located farther from the passage bottom surface 67 than the ceiling top portion 112a in the height direction Y. The inflow upper end portion 113 is located farther from the passage bottom surface 67 than the partition top portion 111a in the height direction Y. In this manner, since the inflow upper end portion 113 is disposed at a position spaced apart from the passage bottom surface 67 as far as possible, the open area of the inflow port 63a is set to be as large as possible. For that reason, it is inhibited that the amount of intake air flowing in from the inflow port 63a is insufficient and the detection accuracy of the flow rate detection unit 52 is lowered.

The outflow upper end portion 114 is located at a position closer to the bottom than the ceiling top portion 112a in the height direction Y. In this manner, since the outflow upper end portion 114 is disposed as close as possible to the passage bottom surface 67, an open area of the outflow port 63b is set to be as small as possible. For that reason, since a pressure of the intake air flowing out from the outflow port 63b is increased, the intake air is likely to flow into the measurement flow channel 62, and the amount of the intake air flowing into the measurement flow channel 62 is insufficient to inhibit the detection accuracy of the flow rate detection unit 52 from being lowered. In addition, the outflow upper end portion 114 is located farther from the passage bottom surface 67 than the restriction top portion 85c in the height direction Y.

In the height direction Y, the partition top portion 111a is disposed on the side opposite to the passage bottom surface 67 across the connecting line PL, so that the partition top portion 111a is not exposed to the upstream side from the inflow port 63a. In that case, the connecting line PL passes between the partition top portion 111a and the passage bottom surface 67, and the ceiling projection portion 112 enters between the partition top portion 111a and the restriction top portion 85c. For that reason, as indicated by a solid line in FIG. 34, when a large foreign matter F5 that has entered the passage flow channel 61 from the inflow port 63a travels linearly along the connecting line PL, the large foreign matter F5 passes through the bottom side of the partition top portion 111a in the height direction Y, and is likely to collide with the outflow ceiling surface portion 66b. As a result of that collision, the traveling direction of the large foreign matter F5 changes with respect to the height direction Y, but is likely to exit from the outflow port 63b. In other words, the large foreign matter F5 traveling linearly in the passage flow channel 61 does not collide with the inner peripheral surface 61a of the passage flow channel 61, and is less likely to enter the measurement flow channel 62 as it is.

Figure 35:
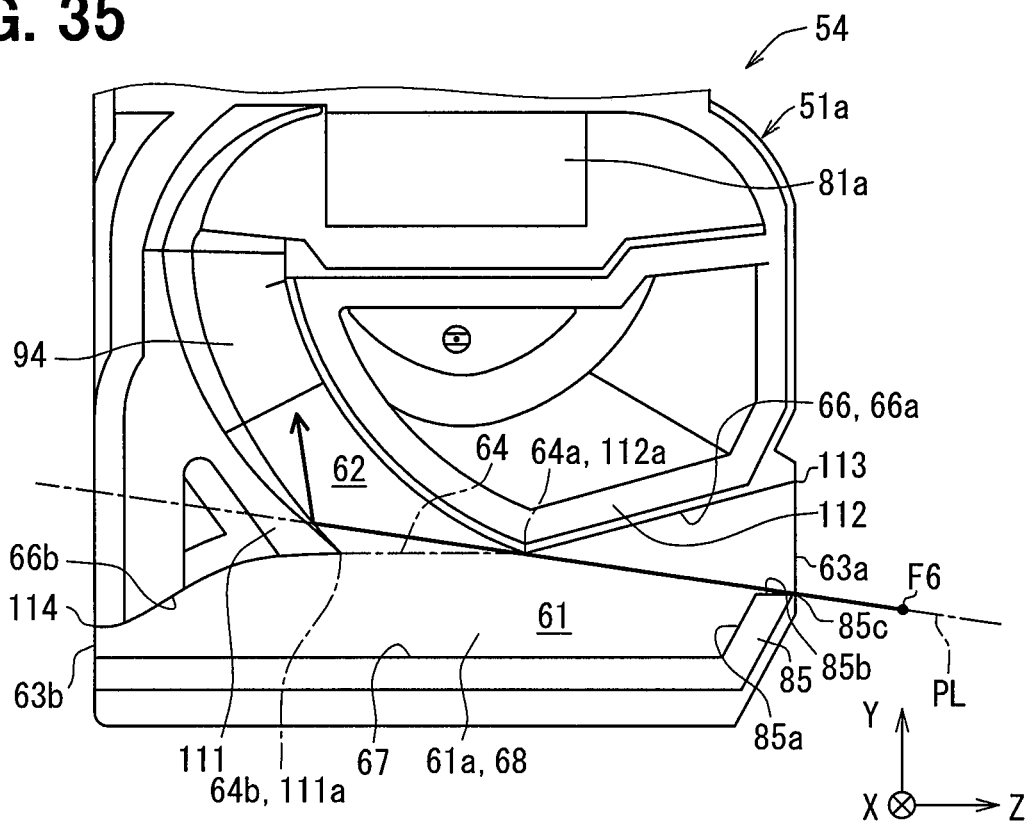
FIG. 35 is a diagram illustrating a configuration in which a partition top portion is exposed to the upstream side from an inflow port, unlike the fourth embodiment.

On the other hand, unlike the present embodiment, in the configuration in which the partition top portion 111a is exposed to the upstream side from the inflow port 63a as shown in FIG. 35, when a large foreign matter F6 travels linearly along the connecting line PL, there is a concern that the large foreign matter F6 enters the measurement flow channel 62 as it is. In that case, the large foreign matter F6 does not collide with the inner peripheral surface 61a and enters the measurement flow channel 62 even though the traveling direction is not changed. In the above configuration, in the height direction Y, the connecting line PL passes through the side opposite to the passage bottom surface 67 across the partition top portion 111a, and the upstream end portion of the measurement flow channel 62 and the flow channel boundary portion 64 are exposed to the upstream side from the inflow port 63a. In that case, for example, when a person looks into the passage flow channel 61 from the inflow port 63a, an inner peripheral surface of the measurement flow channel 62 or the flow channel boundary portion 64 can be visually recognized.

Returning to the description of FIG. 33, the passage flow channel 61 has a straight region 115. The straight region 115 is a region linearly extending so as to connect the inflow port 63a and the outflow port 63b, and the upstream end portion of the straight region 115 is included in the inflow port 63a and the downstream end is included in the outflow port 63b. Unlike the parallel region 101 of the third embodiment, the straight region 115 is not parallel to the depth direction Z but inclined with respect to the depth direction Z. In the present embodiment, the straight region 115 is inclined with respect to the depth direction Z so as to come closer to the passage bottom surface 67 toward the downstream side. The inclination direction is opposite to the connecting line PL, and a straight angle θb indicating the inclination angle with respect to the depth direction Z has a negative value. The straight angle θb is an angle of a portion open to the downstream side between the straight region 115 and the reference line Za. On the other hand, similarly to the parallel region 101 of the third embodiment, a height dimension of the straight region 115 is uniform in any part in the depth direction Z.

Figure 34:
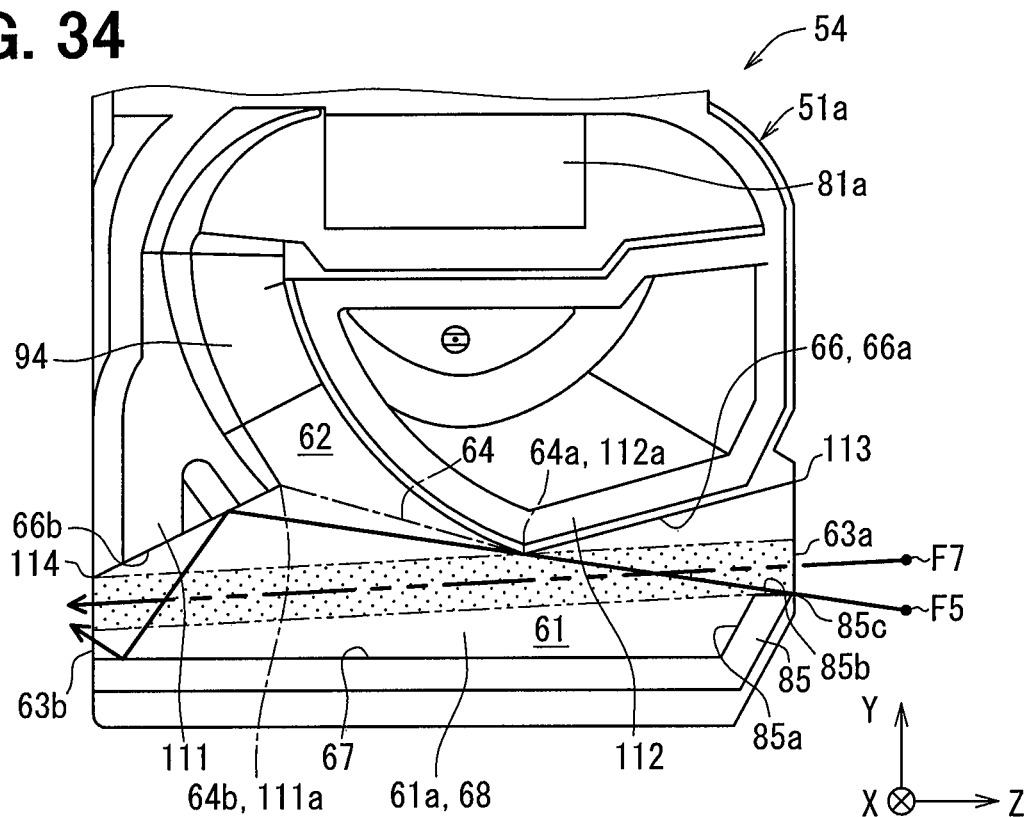
FIG. 34 is a diagram illustrating an traveling direction of a large foreign matter.

As shown in FIG. 34, when a large foreign matter F7 flowing in from the inflow port 63a travels straight along the straight region 115, the large foreign matter F7 exits from the outflow port 63b simply by traveling linearly along the straight region 115. In this example, as described above, the inclination direction with respect to the depth direction Z is opposite between the straight region 115 and the connecting line PL. In that case, if the air flow meter 50 is installed in the intake passage 12 so that the amount of large foreign matter F7 traveling linearly along the straight region 115 increases among the foreign matter contained in the intake air, the number of foreign matter such as the large foreign matter F5 traveling along the connecting line PL itself is likely to decrease. This makes it easy to exert a deterrent force against foreign matter entering the passage flow channel 61 from the inflow port 63a entering the measurement flow channel 62 without colliding with the inner peripheral surface 61a.

According to the present embodiment described so far, since the partition top portion 111a is not exposed to the upstream side through the inflow port 63a, the foreign matter such as the large foreign matter F5 that travels linearly through the passage flow channel 61 does not collide with the inner peripheral surface 61a and enters the measurement flow channel 62 as it is, which is unlikely to occur. This makes it possible to inhibit the foreign matter from adhering to the flow rate detection unit 52 of the measurement flow channel 62, and the detection accuracy of the flow rate detection unit 52 from being lowered by the foreign matter.

According to the present embodiment, since the partition top portion 111a and the downstream boundary portion 64b coincide with each other, a configuration in which the partition top portion 111a is not exposed to the upstream side through the inflow port 63a is realized, thereby being capable of realizing a configuration in which the flow channel boundary portion 64 is also not exposed to the upstream side through the inflow port 63a. For that reason, the foreign matter such as the large foreign matter F5 traveling linearly through the passage flow channel 61 can be surely inhibited from directly entering the measurement flow channel 62 without colliding with the inner peripheral surface 61a.

According to the present embodiment, since the connecting line PL passes through passage bottom surface 67 side of the partition top portion 111a, a configuration in which the partition top portion 111a is not exposed to the upstream side through the inflow port 63a can be realized.

According to the present embodiment, the partition top portion 111a and the upstream boundary portion 64a coincide with each other. In other words, the upstream boundary portion 64a is not disposed on the bottom side of the partition top portion 111a. For that reason, even though the partition top portion 111a is not exposed to the upstream side through the inflow port 63a, the upstream end portion of the measurement flow channel 62 and the flow channel boundary portion 64 can be prevented from being exposed to the upstream side from the inflow port 63a. As a result, the foreign matter such as the large foreign matter F5 that travels linearly along the connecting line PL can be inhibited from entering the measurement flow channel 62 as it is.

According to the present embodiment, since the ceiling top portion 112a is disposed at a height position between the partition top portion 111a and the restriction top portion 85c in the height direction Y, the straight region 115 can be secured by the passage flow channel 61. In this example, unlike the present embodiment, for example, in a configuration in which the ceiling top portion 112a is disposed at a position closer to the passage bottom surface 67 than both of the partition top portion 111a and the restriction top portion 85c in the height direction Y, it is difficult to secure the straight region 115 in the passage flow channel 61 in an appropriate state. In addition, even in a configuration in which the ceiling top portion 112a is disposed at a position farther from the passage bottom surface 67 than both of the partition top portion 111a and the restriction top portion 85c in the height direction Y, it is similarly difficult to secure the straight region 115 in an appropriate state in the passage flow channel 61.

On the other hand, according to the present embodiment, a positional relationship of the partition top portion 111a, the restriction top portion 85c, and the ceiling top portion 112a is set so that the straight region 115 can be secured in an appropriate state. For that reason, the foreign matter such as the large foreign matter F6 traveling linearly through the passage flow channel 61 can be inhibited from entering the measurement flow channel 62 as it is, and a configuration in which the foreign matter such as the large foreign matter F7 is urged to exit from the outflow port 63b as it is can be realized. Examples of the configuration that can secure the straight region 115 in the appropriate state include a configuration in which the inclination angle of the straight region 115 with respect to the depth direction Z does not become too large, a configuration in which the cross-sectional area of the straight region 115 does not become too small, and the like.

According to the present embodiment, since the inflow restriction portion 85 has a function of defining the angle of the connecting line PL as the bottom projection portion, there is no need to newly install a dedicated member or a dedicated portion for defining the angle of the connecting line PL in the passage flow channel 61. This makes it possible to inhibit the complexity of the configuration of the air flow meter 50 and the tendency of disturbance to occur in the flow of the inflow air in the passage flow channel 61 due to the increase in the number of dedicated members and dedicated parts.

According to the present embodiment, since the partition top portion 111*a* is disposed at a position hidden on the depth side of the inflow restriction portion 85 and the ceiling projection portion 112 in the depth direction Z, the partition top portion 111*a* can be surely inhibited from being exposed on the upstream side from the inflow port 63*a*. In that case, a configuration can be realized in which the partition top portion 111*a* is not exposed to the upstream side from the inflow port 63*a* by using the shapes of the passage ceiling surface 66 and the inflow port 63*a*. For that reason, for example, there is no need to newly install a dedicated member or a dedicated portion for covering the partition top portion 111*a*.

The fourth embodiment can be applied to various embodiments and combinations without departing from the scope of the present disclosure.

Figure 36:
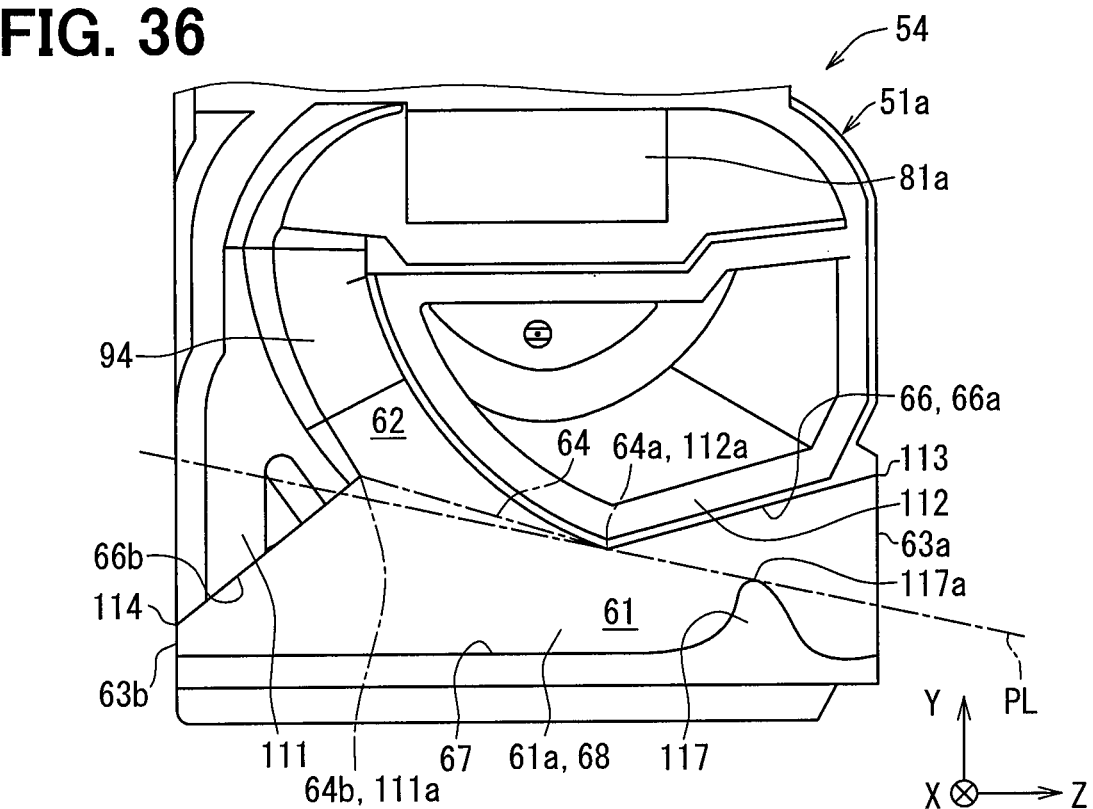
FIG. 36 is a diagram of the periphery of a passage flow channel in a modification D1.

As a modification D1, the bottom projection portion does not have to be the inflow restriction portion 85. For example, as shown in FIG. 36, the bottom projection portion 117 is provided at a position spaced downstream from the inflow port 63*a*. The bottom projection portion 117 is provided on the upstream side of the ceiling top portion 112*a*, and is disposed between the inflow port 63*a* and the ceiling top portion 112*a* in the depth direction Z. The bottom projection portion 117 has a bottom top portion 117*a* which is a tip portion of the bottom projection portion 117, and even in that configuration, the connecting line PL connecting the ceiling top portion 112*a* and the bottom top portion 117*a* passes through the bottom side from the partition top portion 111*a*. As a result, the partition top portion 111*a* is not exposed to the upstream side from the inflow port 63*a*.

As a modification D2, the bottom top such as the restriction top portion 85*c* may be provided on the downstream side of the ceiling top portion 112*a*. For example, in the modification D1, the bottom top portion 117*a* is provided on the downstream side of the ceiling top portion 112*a*. In the above configuration, the bottom top portion 117*a* is disposed between the ceiling top portion 112*a* and the inflow port 63*a* in the depth direction Z, and the bottom projection portion 117 enters between the ceiling top portion 112*a* and the partition top portion 111*a*. For example, the ceiling projection portion 112 is provided in the inflow port 63*a*. Also, in the above configuration, the connecting line PL connecting the ceiling top portion 112*a* and the bottom top portion 117*a* passes through the bottom side of the partition top portion 111*a*. On the other hand, the ceiling top portion 112*a* does not form the upstream boundary portion 64*a*.

Figure 37:
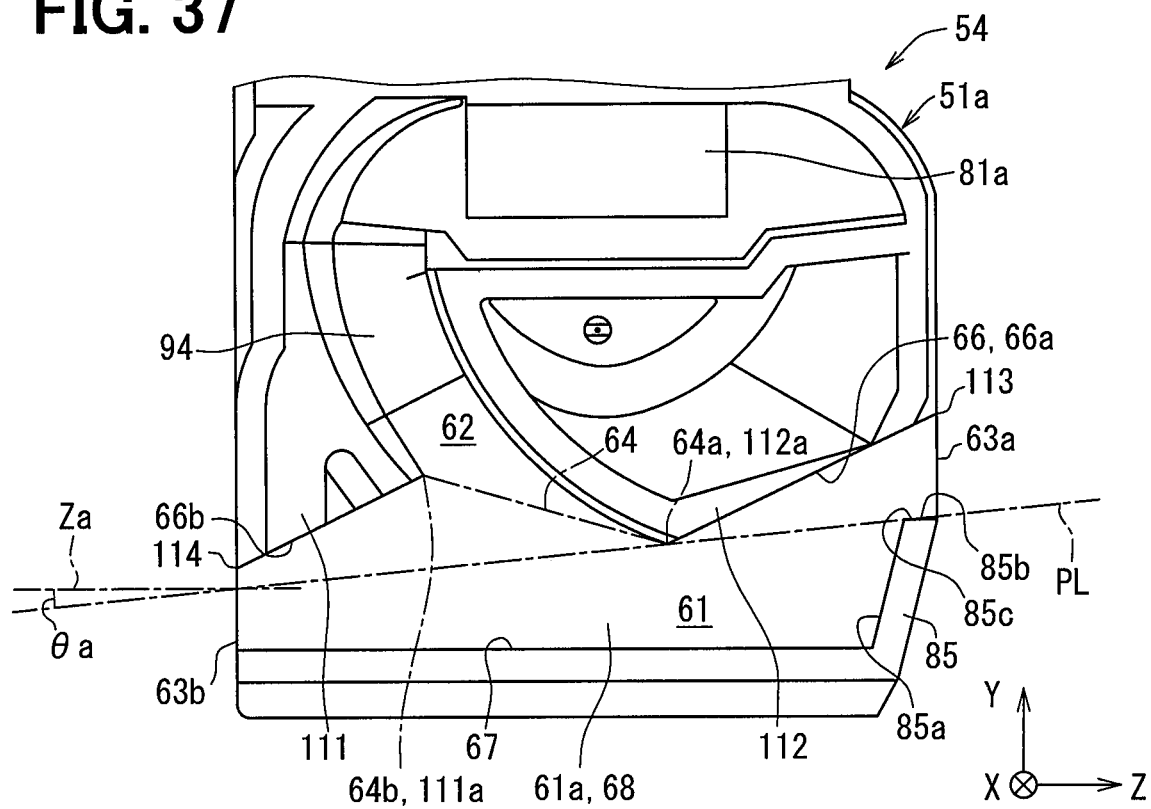
FIG. 37 is a diagram of the periphery of a passage flow channel in a modification D3.

As a modification D3, the connecting line PL may be declined toward the bottom side toward the downstream side. In other words, the connecting angle θa may be a negative value. For example, as shown in FIG. 37, the restriction top portion 85*c* is disposed to be spaced apart from the passage bottom surface 67 more than the ceiling top portion 112*a*. In the above configuration, the downstream end portion of the upper surface 85*b* of the inflow restriction portion 85 becomes the restriction top portion 85*c*. Further, the inclination direction of the connecting line PL with respect to the depth direction Z is the same as the inclination direction of the straight region 115 with respect to the depth direction Z. Also in the above configuration, the partition top portion 111*a* is not exposed to the upstream side from the inflow port 63*a*.

Figure 38:
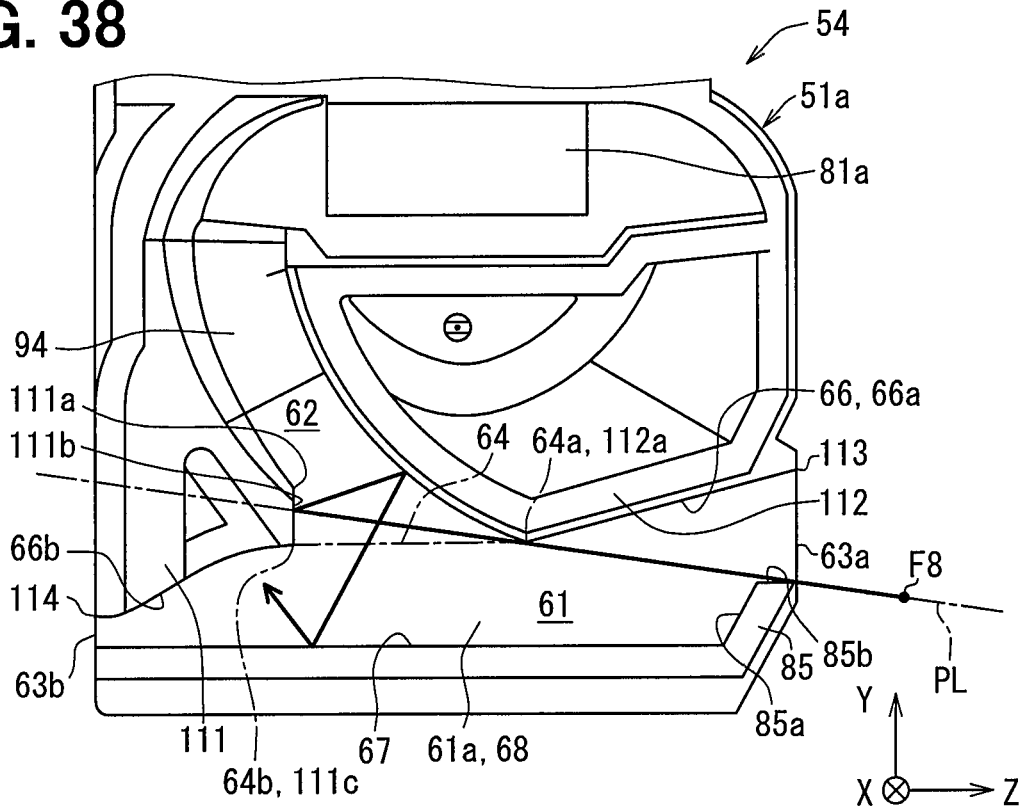
FIG. 38 is a diagram of the periphery of a passage flow channel in a modification D4.

As a modification D4, the tip portion, which is the upstream end portion of the flow channel partition portion 111, may have a flat tip end face. For example, as shown in FIG. 38, the tip end face 111*b* of the flow channel partition portion 111 is a flat surface, and the connecting line PL crosses the tip end face 111*b*. An end portion of the tip end face 111*b* opposite to the bottom side is a partition top face 111*a*, and a bottom side end portion 111*c* opposite to the partition top portion 111*a* forms a downstream boundary portion 64*b*. In this manner, although the partition top portion 111*a* and the downstream boundary portion 64*b* do not coincide with each other, even in this configuration, the partition top portion 111*a* is not exposed to the upstream side from the inflow port 63*a*. In that case, for example, a large foreign matter F8 that travels linearly along the connecting line PL is likely to be returned from the measurement flow channel 62 to the passage flow channel 61 by colliding with the inner peripheral surface of the measurement flow channel 62 and rebounding even when the large foreign object F8 once enters the measurement flow channel 62 beyond the flow channel boundary portion 64. In other words, the large foreign matter F8 is likely to exit from the outflow port 63*b*.

As a modification D5, the straight region 115 may extend in parallel to the depth direction Z, similarly to the parallel region 101 of the third embodiment. Also in the above configuration, since the connecting line PL and the straight region 115 are relatively inclined, that is, the connecting angle θa and the straight angle θb are different from each other, a configuration can be realized in which the partition top portion 111*a* is not exposed to the upstream side from the inflow port 63*a*.

As a modification D6, a part of the tip portion, which is the upstream end portion of the flow channel partition portion 111, may be exposed to the upstream side from the inflow port 63*a*. In this example, it is assumed that the tip end face of the flow channel partition portion 111 is flat or curved, so that a range of the tip portion cannot be clearly specified in the flow channel partition portion 111, and the flow channel boundary portion 64 cannot also be clearly specified.

Figure 39:
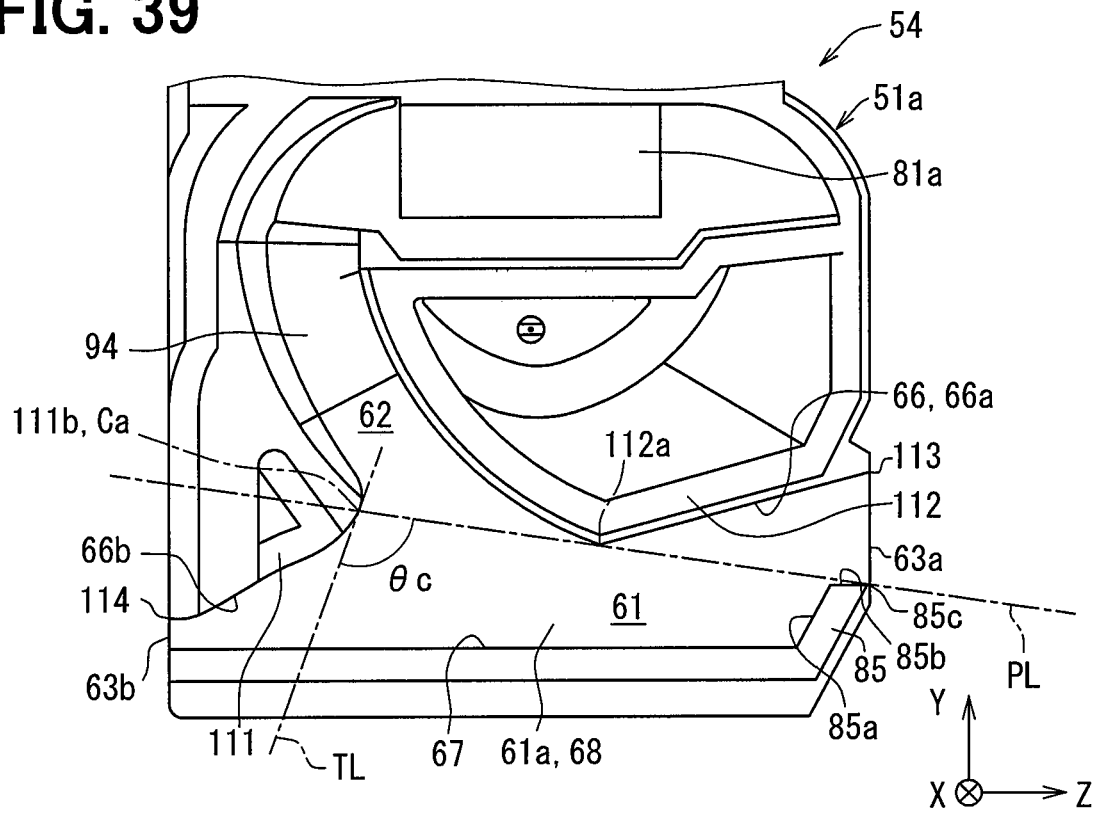
FIG. 39 is a diagram of the periphery of a passage flow channel in a modification D6.

For example, as shown in FIG. 39, the tip end face 111*b* of the flow channel partition portion 111 and the connecting line PL intersect with each other. In the above configuration, an intersection angle θc between the connecting line PL and the tip end face 111*b* is greater than 90 degrees. The tip end face 111*b* is a curved surface that is curved so as to protrude toward the upstream side. In this example, a point at which the connecting line PL and the tip end face 111*b* intersect with each other is referred to as an intersection Ca, and a tangent line of the tip end face 111*b* at the intersection Ca is referred to as a partition tangent line TL, and the intersection angle θc is an angle of a portion that is open toward the downstream side between the connecting line PL and the partition tangent line TL.

Figure 40:
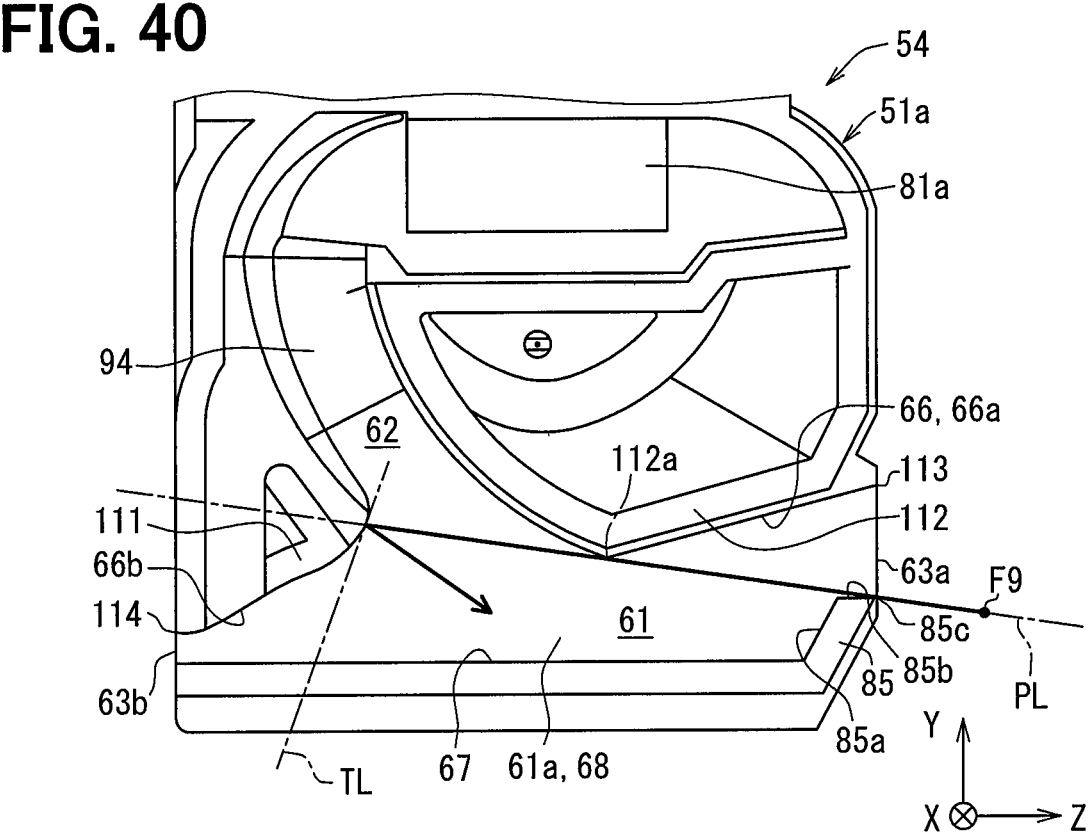
FIG. 40 is a diagram illustrating how a large foreign matter advances.

In the above configuration, for example, as shown in FIG. 40, the large foreign matter F9 traveling linearly along the connecting line PL is likely to rebound to the bottom side toward the upstream side in the height direction Y after colliding with the tip end face 111*b* of the flow channel partition portion 111. In other words, a large foreign matter F9 is likely to rebound toward the side opposite to the measurement flow channel 62. This makes it possible to inhibit that the foreign matter such as the large foreign matter F9 is likely to rebound on the tip end face 111*b* and enter the measurement flow channel 62. On the other hand, unlike the present modification D6, in the configuration in which the intersection angle θc is less than 90 degrees, it is considered that the large foreign matter F9 is likely to rebound toward the upstream side to the side opposite to the bottom side. In other words, it is considered that the large foreign matter F9 enters the measurement flow channel 62 by rebounding at the tip end face 111b of the flow channel partition portion 111.

Figure 41:
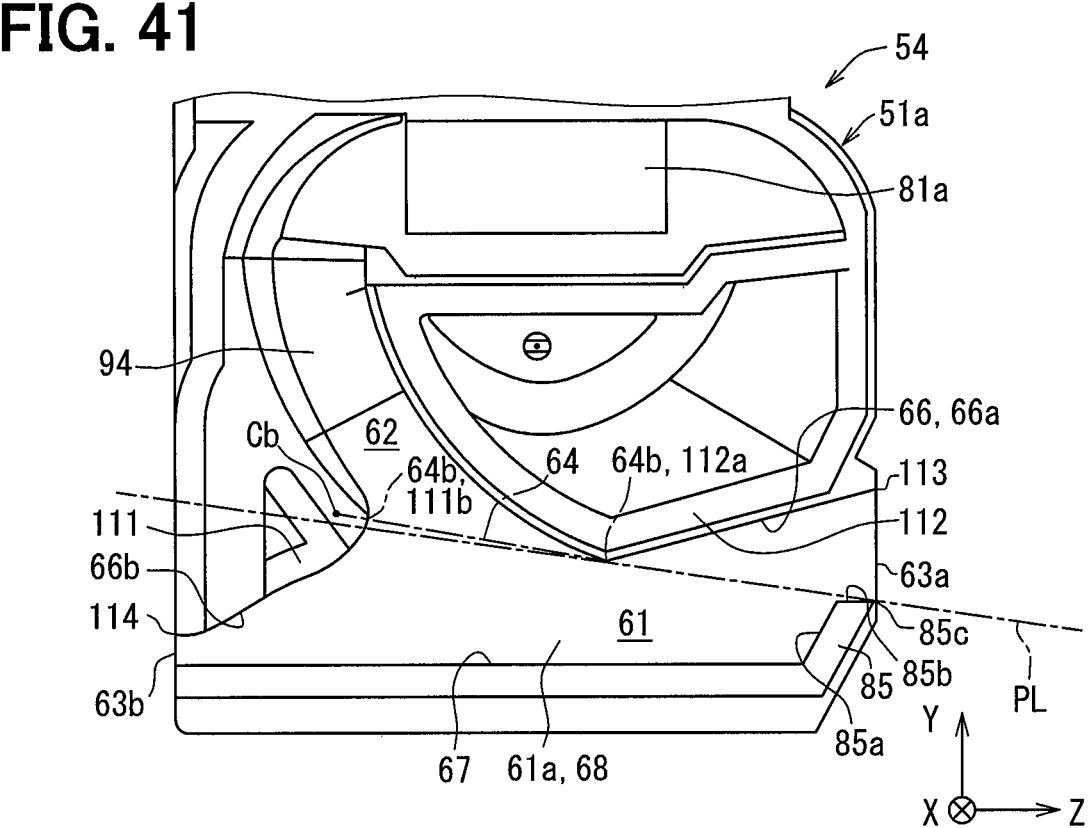
FIG. 41 is a diagram of the periphery of a passage flow channel in a modification D7.

As a modification example D7, as shown in FIG. 41, in the configuration in which the tip end face 111b of the flow channel partition portion 111 is a curved surface, the connecting line PL passes through the bottom side from the partition center line Cb of the curvature. In the above configuration, the tip end face 111b and the partition center line Cb extend in parallel to the width direction X, and the flow channel boundary portion 64 is disposed at a position overlapping with the virtual line connecting the partition center line Cb and the ceiling top portion 112a. In the above configuration, an angle between the tangent line of the tip end face 111b and the connecting line PL is greater than 90 degrees at a point where the connecting line PL and the tip end face 111b intersect with each other, as in the case of the modification D6. For that reason, the foreign matter that travels linearly along the connecting line PL is likely to travel to the opposite side of the measurement flow channel 62 by rebounding at the tip end face 111b of the flow channel partition portion 111. For that reason, the foreign matter can be inhibited from entering the measurement flow channel 62.

Fifth Embodiment

An air flow meter 50 according to a fifth embodiment has an guiding surface on which a foreign matter that is likely to travel linearly is brought toward one wall surface of a pair of wall surfaces in the width direction X. In the present embodiment, similarly to the third and fourth embodiments, differences from the second embodiment will be mainly described.

Figure 42:
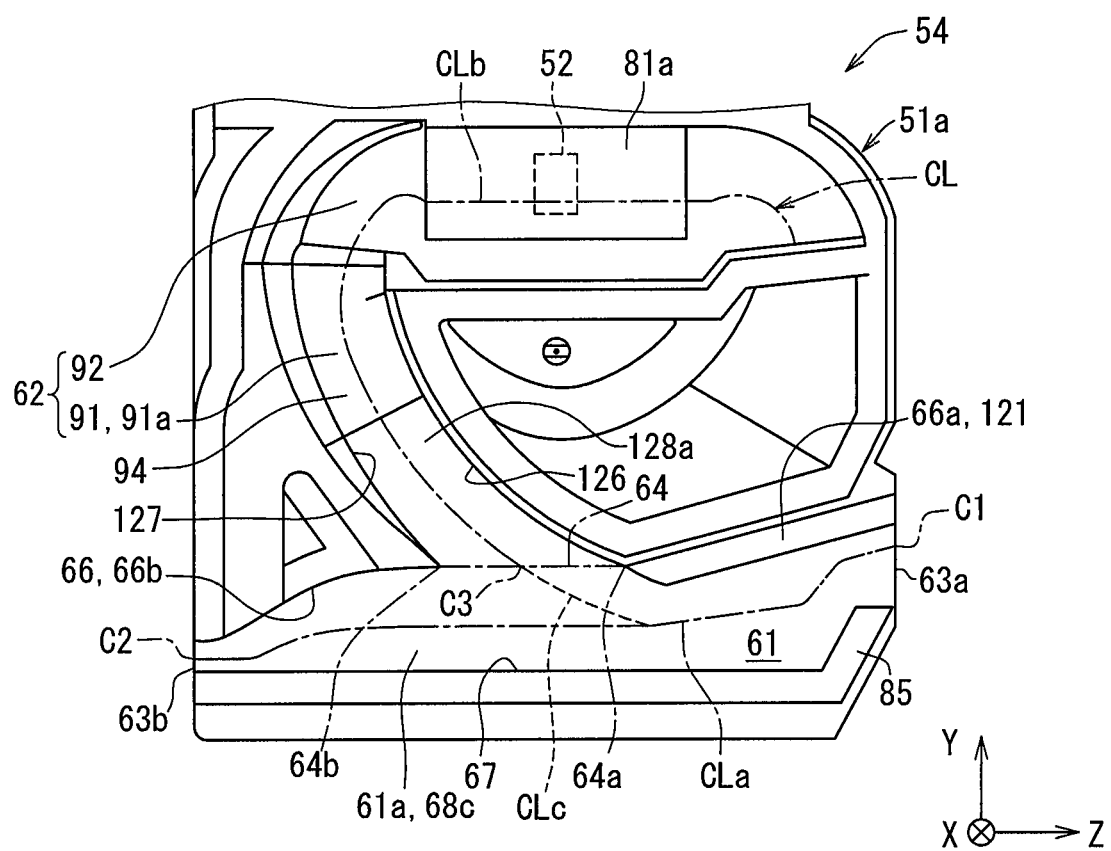
FIG. 42 is a diagram of the periphery of a passage flow channel according to a fifth embodiment.
Figure 43:
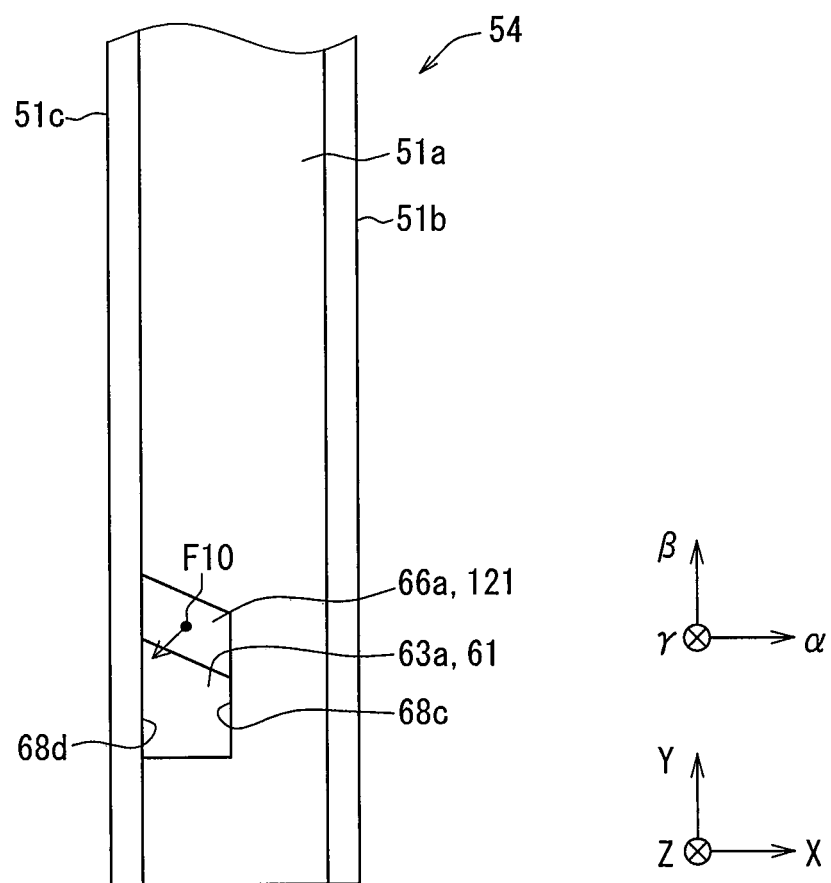
FIG. 43 is a diagram of the vicinity of the inflow port of the air flow meter as viewed from the upstream side.
Figure 44:
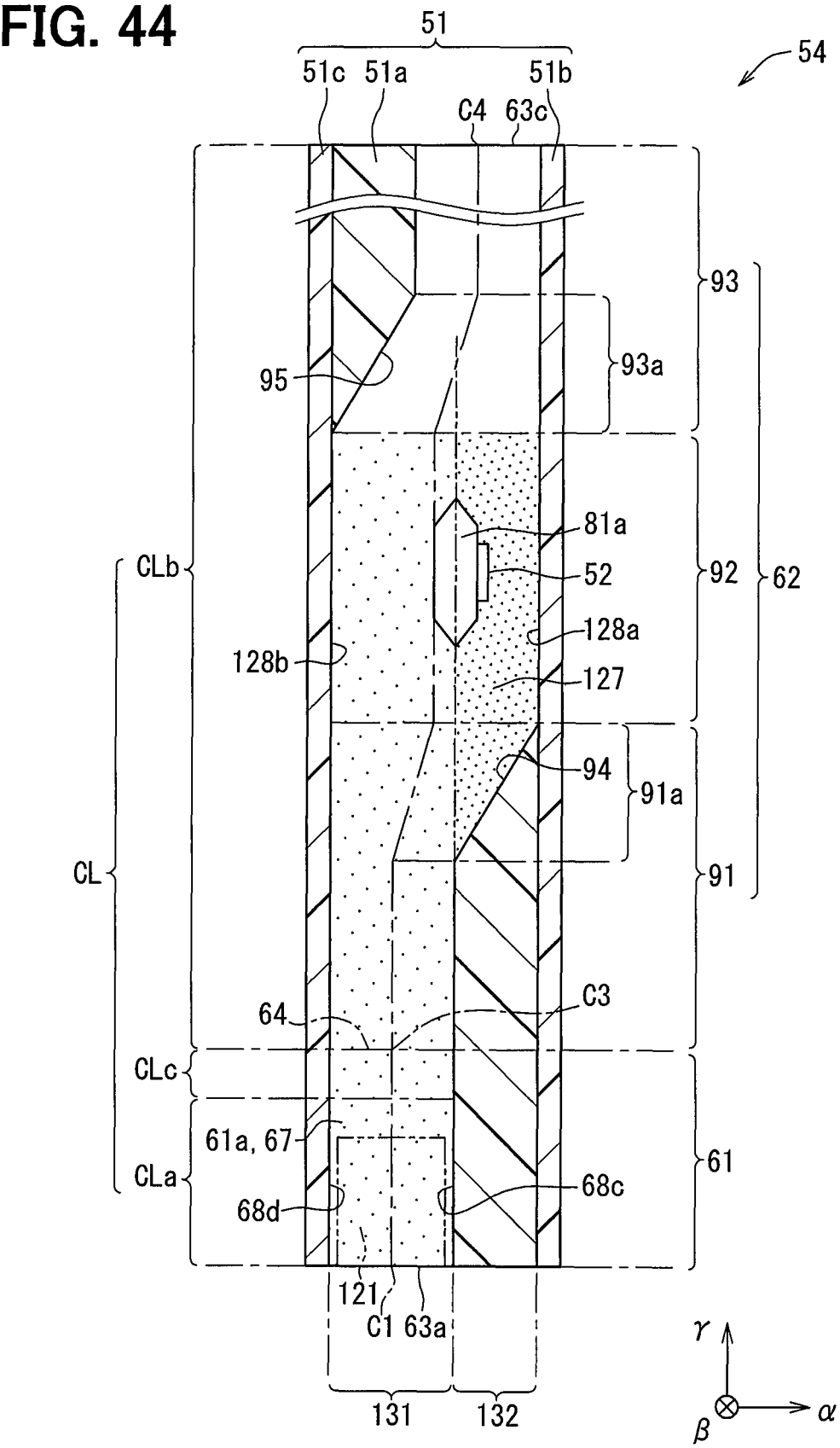
FIG. 44 is a diagram illustrating an inflow region and a lateral region.

As shown in FIGS. 42 to 44, in the present embodiment, the pair of passage wall surfaces 68 in the second embodiment is a pair of passage wall surfaces 68c and 68d, and those passage wall surfaces 68c and 68d correspond to passage facing surfaces. One front passage wall surface 68c is formed by a front cover 51b and a housing main body 51a, and the other back passage wall surface 68d is formed by a back cover 51c and the housing main body 51a. An inner peripheral surface 61a of the passage flow channel 61 has a guiding surface 121. The guiding surface 121 is included in the inflow ceiling surface portion 66a, and is provided in a state of being extended over the pair of passage wall surfaces 68c and 68d, similarly to an inflow restriction portion 85. In the width direction X, one end portion of the guiding surface 121 is disposed closer to the bottom than the other end. The housing main body 51a corresponds to a partition wall portion that partitions the passage flow channel 61 and the measurement flow channel 62 in the width direction X.

In the present embodiment, the guiding surface 121 has an end close to the front passage wall surface 68c is disposed to be closer to the bottom side than another end close to the back passage wall surface 68d. In that case, the guiding surface 121 is an inclined surface gradually away from the bottom surface 67 as the guiding surface 121 comes closer to the back passage wall surface 68d in the width direction X. The inclination angle of the guiding surface 121 with respect to the width direction X is set to, for example, several degrees to several tens of degrees less than 45 degrees. A width dimension of the guiding surface 121 in the width direction X is larger than the height dimension in the height direction Y. The guiding surface 121 extends from an inflow port 63a toward the downstream side, and forms substantially the entire inflow ceiling surface portion 66a.

The center line of the passage flow channel 61 is referred to as a passage center line CLa. The passage center line CLa is a virtual line connecting the center C1 of the inflow port 63a and the center C2 of the outflow port 63b (refer to FIG. 42). The center line of the measurement flow channel 62 is referred to as a measurement center line CLb. The measurement center line CLb is a virtual line connecting the center C3 of the flow channel boundary portion 64 and a center C4 of a measurement outlet 63c (refer to FIG. 44). In this example, a virtual line connecting the center C1 of the inflow port 63a and the center C4 of the measurement outlet 63c is referred to as a flow channel center line CL, and the flow channel center line CL includes the entire passage center line CLa and a part of the measurement center line CLb. The flow channel center line CL includes a connecting center line CLc as a virtual line connecting the passage center line CLa and the measurement center line CLb. The connection center line CLc is connected to the passage center line CLa by extending from the center C3 of the flow channel boundary portion 64 toward the upstream side of the passage flow channel 61.

The inner peripheral surface 62a of the measurement flow channel 62 has a measurement ceiling surface 126, a measurement bottom surface 127, and a pair of measurement wall surfaces 128a and 128b. The pair of measurement wall surfaces 128a and 128b are opposed to each other across the flow channel boundary portion 64 and the measurement outlet 63c in the width direction X, and correspond to branch facing surfaces. The front measurement wall surface 128a is formed by the front cover 51b and the housing main body 51a, similarly to the front passage wall surface 68c, and the back measurement wall surface 128b is formed by the back cover 51c and the housing main body 51a, similarly to the back passage wall surface 68d. The front measurement wall surface 128a has a width increasing surface 94, and the back measurement wall surface 128b has a width decreasing surface 95. The width increasing surface 94 and the width decreasing surface 95 are formed by the housing main body 51a.

The measurement ceiling surface 126 extends from the downstream end portion of the inflow ceiling surface portion 66a toward the downstream side of the measurement flow channel 62, and is in a state of being extended over the inflow ceiling surface portion 66a and the measurement outlet 63c. The measurement bottom surface 127 extends from the upstream end portion of the outflow ceiling surface portion 66b toward the downstream side of the measurement flow channel 62, and is in a state of being extended to the outflow ceiling surface portion 66b and the measurement outlet 63c. In that case, the measurement ceiling surface 126 and the measurement bottom surface 127 face each other across the measurement wall surfaces 128a and 128b.

In the present embodiment, in addition to the width direction X, the height direction Y, and the depth direction Z, the lateral direction α, the longitudinal direction β, and the flow channel direction γ are used to describe the configurations of the passage flow channel 61 and the measurement flow channel 62. The lateral direction α has only a component in the width direction X. In the lateral direction α, a pair of passage wall surfaces 68c and 68d are aligned with each other, and a pair of measurement wall surfaces 128a and 128b are aligned with each other. The flow channel direction γ is basically a direction in which the passage flow channel 61 and the measurement flow channel 62 extend, does not have a component in the width direction X, and has a component in the height direction Y and a component in the depth direction Z. The longitudinal direction β is orthogonal to both the lateral direction α and the flow channel direction γ, and has no component in the width direction X, but has a component in the height direction Y and a component in the depth direction Z, similarly to the flow channel direction γ. In the longitudinal direction β, the passage ceiling surface 66 and the passage bottom surface 67 face each other, and the measurement ceiling surface 126 and the measurement bottom surface 127 face each other. The longitudinal direction β and the flow channel direction γ are different from the lateral direction α, and change at positions of the flow channels 61 and 62 because the passage flow channel 61 and the measurement flow channel 62 are curved.

FIG. 44 shows a diagram in which the passage flow channel 61 and the measurement flow channel 62 are extended along the flow channel center line CL with respect to the longitudinal direction β in the region between the inflow port 63a and the measurement outlet 63b, when the measurement bottom surface 127 is viewed from the measurement ceiling surface 126 side. In FIG. 43, because the flow channel direction γ of the inflow port 63a coincides with the depth direction Z, the width direction X coincides with the lateral direction α, the height direction Y coincides with the longitudinal direction β, and the depth direction Z coincides with the flow channel direction γ.

As shown in FIG. 44, the passage flow channel 61 and the measurement flow channel 62 include an inflow region 131 and a lateral region 132, and those regions 131 and 132 extend along the flow channel direction γ. The inflow region 131 is a region in which the inflow port 63a is projected in the flow channel direction γ, and extends from the inflow port 63a toward the measurement outlet 63c. In the present embodiment, the inflow region 131 extends to the downstream end portion of the intermediate measurement path 92.

The lateral region 132 is disposed side by side in the lateral direction α in the inflow region 131. The lateral region 132 is disposed on the side of the front measurement wall surface 128a, and the inflow region 131 is disposed on the side of the back measurement wall surface 128b. The lateral region 132 is disposed on the downstream side of the width increasing surface 94 in the flow channel direction γ, and does not extend from the inflow port 63a. For that reason, the lateral region 132 does not include a region in which the inflow port 63a is projected in the flow channel direction γ. The lateral region 132 is a region increased in the measurement flow channel 62, including a portion in which the width dimension of each of the width increasing portion 91a and the intermediate measurement path 92 in the lateral direction α is larger than the width dimension of the upstream-side portion of the width increasing portion 91a in the upstream measurement path 91. In the lateral direction α, the width dimension of the inflow region 131 is larger than the width dimension of the lateral region 132. The width dimension of the inflow region 131 may be the same as or smaller than the width dimension of the lateral region 132. In this description, the width dimensions of the portions having the largest width dimensions in each of the inflow region 131 and the lateral region 132 are compared with each other.

The upstream measurement path 91 corresponds to an upstream branch path, the intermediate measurement path 92 corresponds to an intermediate branch path, and the downstream measurement path 93 corresponds to a downstream branch path.

Like the parallel region 101 and the like, the inflow region 131 and the lateral region 132 are virtual regions, and the passage flow channel 61 and the measurement flow channel 62 are not actually divided into the inflow region 131 and the lateral region 132. Further, in FIG. 44, the inflow region 131 is illustrated by lighter dot hatching, and the lateral region 132 is illustrated by darker dot hatching.

The flow rate detection unit 52 is disposed in the lateral region 132 in the intermediate measurement path 92. The measurement board portion 81a is disposed at a position extending across the inflow region 131 and the lateral region 132 in the lateral direction α so that the substrate surface on which the flow rate detection unit 52 is mounted is included in the lateral region 132. The flow rate detection unit 52 is disposed at a position not overlapping with the inflow port 63a in the flow channel direction γ. In other words, the flow rate detection unit 52 is hidden from the upstream side by a portion forming the width increasing surface 94 in the housing main body 51a or the width increasing surface 94 in the flow channel direction γ. The measurement board portion 81a may be disposed in a position in which the entire measurement substrate portion is included in the lateral region 132.

In the flow channel direction γ, a separation distance between the flow rate detection unit 52 and the width increasing surface 94 and a separation distance between the measurement board portion 81a and the width increasing surface 94 are both smaller than a length dimension of the width increasing surface 94. As a result, the measurement board portion 81a and the flow rate detection unit 52 are disposed at positions relatively close to the width increasing surface 94. An inclination angle of the width increasing surface 94 with respect to the flow channel direction γ is smaller than 45 degrees, for example. In that case, since a width dimension of the measurement flow channel 62 in the lateral direction α does not increase abruptly as the measurement flow channel 62 approaches the intermediate measurement path 92 but gradually increases, turbulence of the air flow such as a vortex is less likely to occur in the intake air reaching the lateral region 132.

The guiding surface 121 of the passage flow channel 61 is inclined toward the back cover 51c in a state facing the bottom side, and thus is not orthogonal to the longitudinal direction β. The guiding surface 121 is gradually inclined toward the bottom as the inflow ceiling surface portion 66a comes closer to the flow channel boundary portion 64 as described above, so that the guiding surface 121 is exposed upstream from the inflow port 63a in the depth direction Z. Therefore, as shown in FIG. 43, when a large foreign matter F10 traveling linearly in the depth direction Z collides with the guiding surface 121, the traveling direction of the large foreign matter F10 is changed toward the back passage wall surface 68d side and the passage bottom surface 67 side with respect to the width direction X and the height direction Y. In other words, the traveling direction of the large foreign matter F10 is not a direction parallel to the flow channel direction γ, but a direction inclined with respect to the flow channel direction γ so as to include the components of the lateral direction α and the longitudinal direction β.

Next, the way of how the foreign matter whose traveling direction is changed by the guiding surface 121 travels will be described with reference to FIG. 45. It should be noted the foreign matter entering the measurement flow channel 62 from the passage flow channel 61 is an object to be described hereafter, and therefore a description of a change in the traveling direction of the foreign matter in the longitudinal direction β will be omitted. In this example, both situations where the traveling direction of the foreign matter is changed and unchanged in the longitudinal direction β are assumed, and in either case, the foreign matter may be traveling along the flow channel direction γ.

Figure 45:
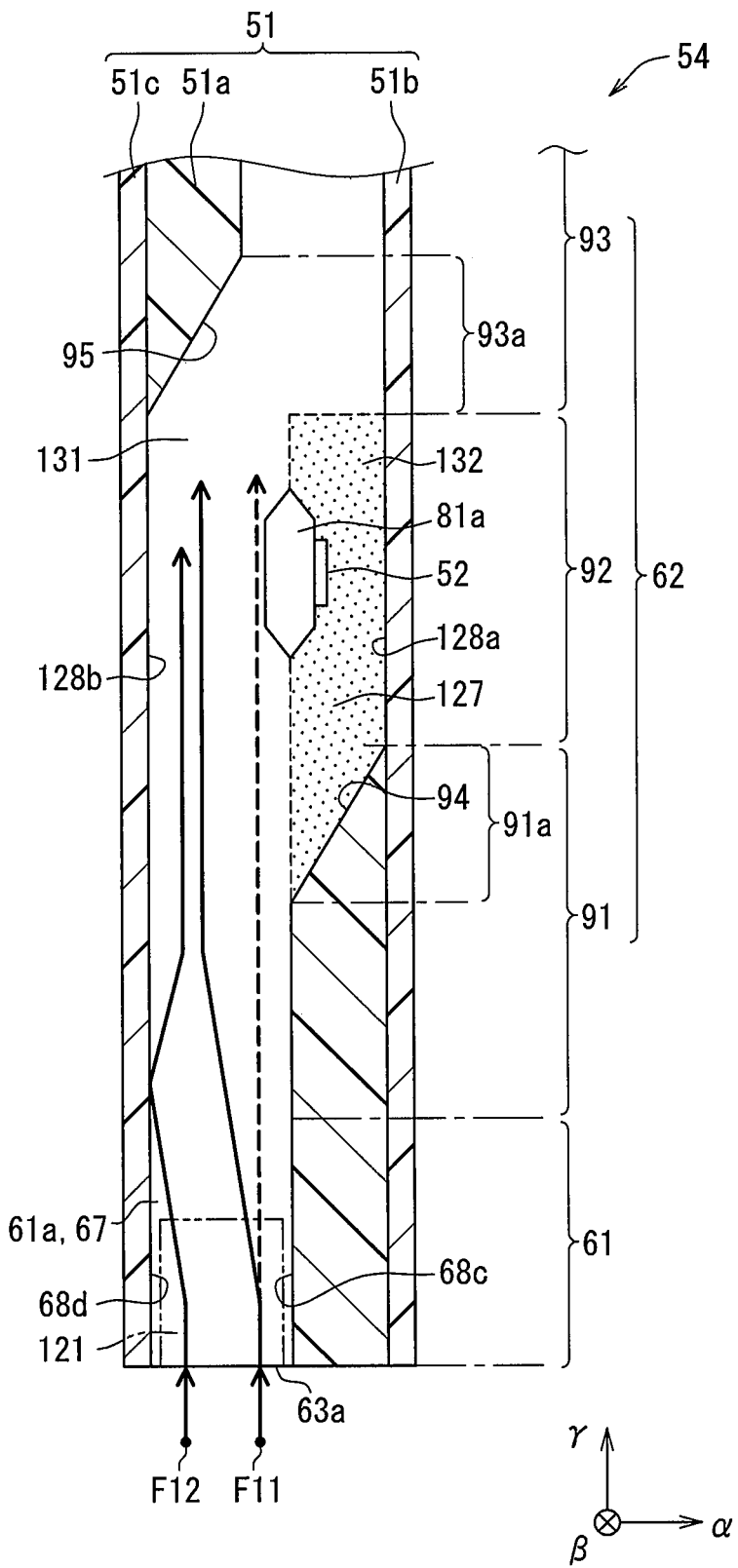
FIG. 45 is a diagram illustrating how a large foreign matter advances.

As shown in FIG. 45, when large foreign matter F11, F12 traveling linearly in the flow channel direction γ collides with the guiding surface 121, like the large foreign matter F10 described in FIG. 43, both the large foreign matter F11, F12 travel in a direction angled with respect to the flow channel direction γ toward the back cover 51c. In this example, the large foreign matter F11 collides with the guiding surface 121 at a position closer to the front cover 51b in the lateral direction α, and the large foreign matter F12 collides with the guiding surface 121 at a position closer to the back cover 51c. An inclination angle of the guiding surface 121 with respect to the lateral direction α is relatively small, and this causes the change in the traveling direction of the large foreign matter F11 and F12 by the guiding surface 121 to be relatively small. For that reason, the traveling directions of the large foreign matter F11 and F12 are changed by the guiding surface 121, and then proceed along a flow of the intake air, so that the large foreign matter F11 and F12 is likely to coincide with each other in the flow channel direction γ again.

Specifically, the large foreign matter F11 that has collided with the guiding surface 121 proceeds obliquely from the position closer to the front cover 51b toward the back cover 51c, and then proceeds in the flow channel direction γ by gradually changing the traveling direction by the flow of the intake air at a position before reaching the back cover 51c. In that case, even when the large foreign matter F11 reaches the intermediate measurement path 92 and is closest to the measurement circuit board portion 81a, the large foreign matter F11 passes through a position closer to the back cover 51c that is relatively distant from the measurement board portion 81a or the lateral region 132 in the lateral direction α. For that reason, even if the traveling direction of the large foreign matter F11 slightly changes in the direction facing the front cover 51b side, it is difficult for the large foreign matter F1 to enter from the inflow region 131 into the lateral region 132.

On the other hand, unlike the present embodiment, for example, in a configuration in which the guiding surface 121 is not provided, the large foreign matter F11 passes through a position relatively close to the measurement board portion 81a or the lateral region 132 in the lateral direction α as it is as shown by a dashed line in FIG. 45. For that reason, even if the traveling direction of the large foreign matter F11 is slightly changed to the direction of the front cover 51b, the large foreign matter F11 is likely to enter the lateral region 132 from the inflow region 131. In that case, there is a concern that the large foreign matter F11 passes between the flow rate detection unit 52 and the front cover 51b and adheres to the flow rate detection unit 52.

In addition, the large foreign matter F12 that has collided with the guiding surface 121 at a position closer to the back cover 51c than the large foreign matter F11 travels obliquely toward the back cover 51c as indicated by a solid line in FIG. 45, collides with the back cover 51c, and accordingly travels obliquely toward the front cover 51b. Thereafter, the large foreign matter F12 travels along the flow of the intake air at a position slightly distant from the back cover 51c, thereby traveling in the flow channel direction γ. Even in that case, even when the large foreign matter F12 reaches the intermediate measurement path 92 and is closest to the measurement board portion 81a, as in the case of the large foreign matter F11, the large foreign matter F12 passes through the position closer to the back cover 51c which is relatively distant from the measurement board portion 81a or the lateral region 132 in the lateral direction α.

According to the present embodiment described so far, since the flow rate detection unit 52 is provided in the lateral region 132 which is a region not projected along the flow channel direction γ from the inflow port 63a, the foreign matter traveling in the inflow region 131 can be inhibited from reaching the flow rate detection unit 52. In addition, since the guiding surface 121 for bringing the foreign matter away from the lateral region 132 in the lateral direction α is provided in the passage flow channel 61, the foreign matter reaching the intermediate measurement path 92 is less likely to pass through a position close to the lateral region 132. As a result, the foreign matter can be more surely inhibited from reaching the flow rate detection unit 52.

According to the present embodiment, since the guiding surface 121 is extended over the pair of wall surfaces 128a and 128b, in the passage flow channel 61, the foreign matter can be brought in closer to the guiding surface 121 in the entire range in the lateral direction α. For that reason, the probability that the foreign matter that has entered the measurement flow channel 62 passes through the position close to the lateral region 132 in the lateral direction α can be reduced.

According to the present embodiment, since the guiding surface 121 is disposed on the upstream side of the flow channel boundary portion 64 in the passage flow channel 61, the separation distance between the guiding surface 121 and the lateral region 132 in the flow channel direction γ can be appropriately ensured. In that case, after the traveling direction of the foreign matter has changed due to the collision of the foreign matter with the guiding surface 121, a distance and a time for the traveling direction of the foreign matter to coincide with the flow channel direction γ again by the flow of the intake air can be secured until the foreign matter reaches the intermediate measurement path 92. This makes it difficult for the foreign matter to reach the intermediate measurement path 92 and enter the lateral region 132 while the traveling direction of the foreign matter is inclined with respect to the flow channel direction γ by the guiding surface 121.

According to the present embodiment, the width increasing surface 94 included in the front measurement wall surface 128a is gradually away from the back measurement wall surface 128b as the width increasing surface 94 comes closer to the measurement outlet 63c, thereby forming the lateral region 132. In that case, for example, as compared with a configuration in which the width increasing surface 94 extends in parallel with the lateral direction α, the turbulence such as a vortex flow is less likely to occur in the intake air reaching the lateral region 132. For that reason, the foreign matter can be inhibited from entering the lateral region 132 by being entrained in the disturbance of the intake air.

According to the present embodiment, the inflow region 131 and the lateral region 132 are reserved by leveraging a difference in the structure that the upstream measurement path 91 is located between the housing main body 51a and the back cover 51c, while the intermediate measurement path 92 is placed between the front cover 51b and the back cover 51c. In that case, since there is no need to newly install a dedicated member or a dedicated portion for forming the lateral region 132 in the housing 51, the structure of the housing 51 is avoided from becoming complicated, the disturbance of the flow of the intake air by the dedicated member or the like in the measurement flow channel 62, and the like can be avoided.

In the present embodiment, a separation distance between the flow rate detection unit 52 and the width increasing surface 94 in the flow channel direction γ is smaller than a length dimension of the width increasing surface 94. In other words, the flow rate detection unit 52 is disposed at a position relatively close to the width increasing surface 94. In that configuration, when the foreign matter such as the large foreign matter F11 and F12 or the like reaches the intermediate measurement path 92, the foreign matter immediately passes through the opposite side of the flow rate detection unit 52 across the measurement board portion 81a. For that reason, the foreign matter is less likely to enter the lateral region 132 on the upstream side of the flow rate detection unit 52.

The fifth embodiment can be applied to various embodiments and combinations without departing from the scope of the present disclosure.

As a modification E1, the guiding surface 121 may be included in the passage bottom surface 67 and the passage wall surfaces 68c and 68d, instead of being included in the passage ceiling surface 66. For example, a configuration in which the guiding surface 121 is included in the passage bottom surface 67 in a state of being extended over a pair of wall surfaces 68c, 68d is applied, or a configuration in which the guiding surface 121 is included in the front passage wall surface 68c is applied. In the configuration in which the guiding surface 121 is included in the front passage wall surface 68c, the front passage wall surface 68c protrudes toward the back passage wall surface 68d, and the guiding surface 121 is formed by a surface of the protruding portion on the back passage wall surface 68d side. Also in that configuration, the traveling direction of the foreign matter colliding with the guiding surface 121 is temporarily inclined toward the back cover 51c, so that the position of the foreign matter in the lateral direction α can be moved to a position closer to the back cover 51c.

As a modification E2, the guiding surface 121 may be provided at a position downstream of the inflow port 63a in the passage flow channel 61. For example, the guiding surface 121 is provided at an intermediate position between the inflow port 63a and the flow channel boundary portion 64. In that configuration, a part of the inflow ceiling surface portion 66a protrudes toward the bottom side at an intermediate position between the inflow port 63a and the flow channel boundary portion 64, and the guiding surface 121 is formed by the bottom side surface of the protruding portion.

Figure 46:
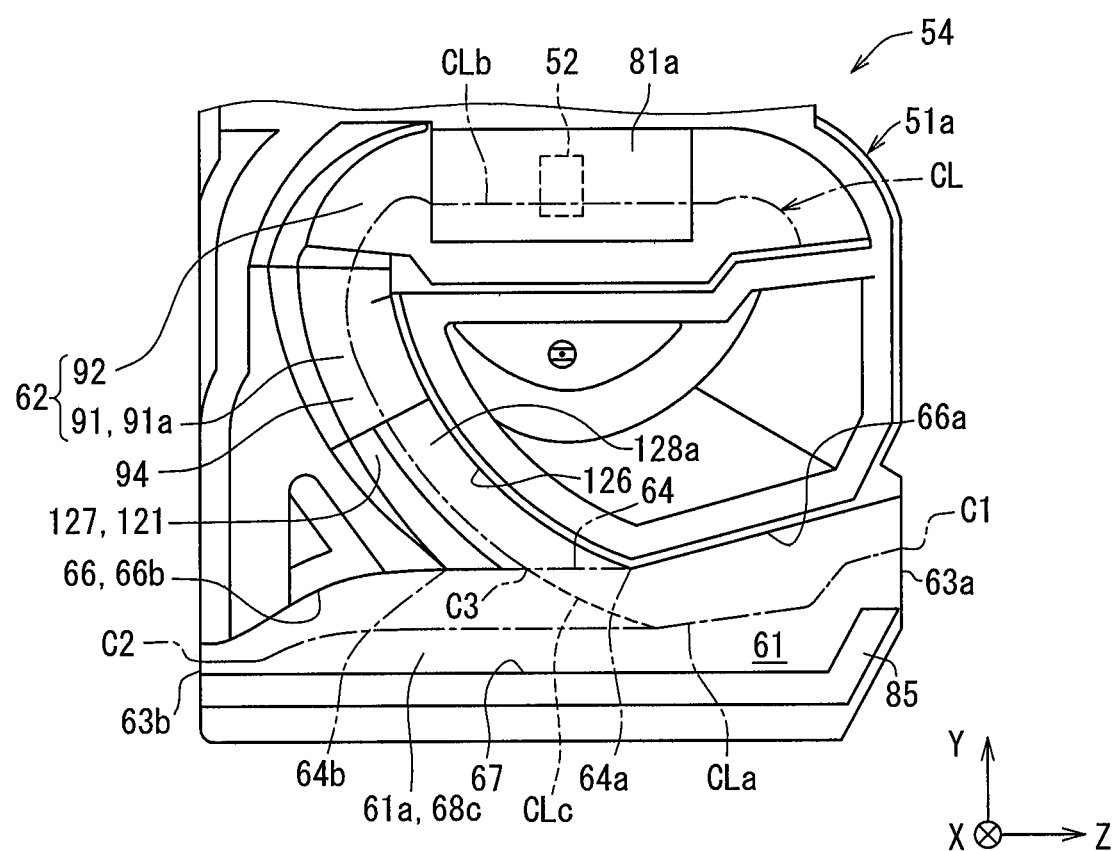
FIG. 46 is a diagram of the periphery of a passage flow channel in a modification E3.
Figure 47:
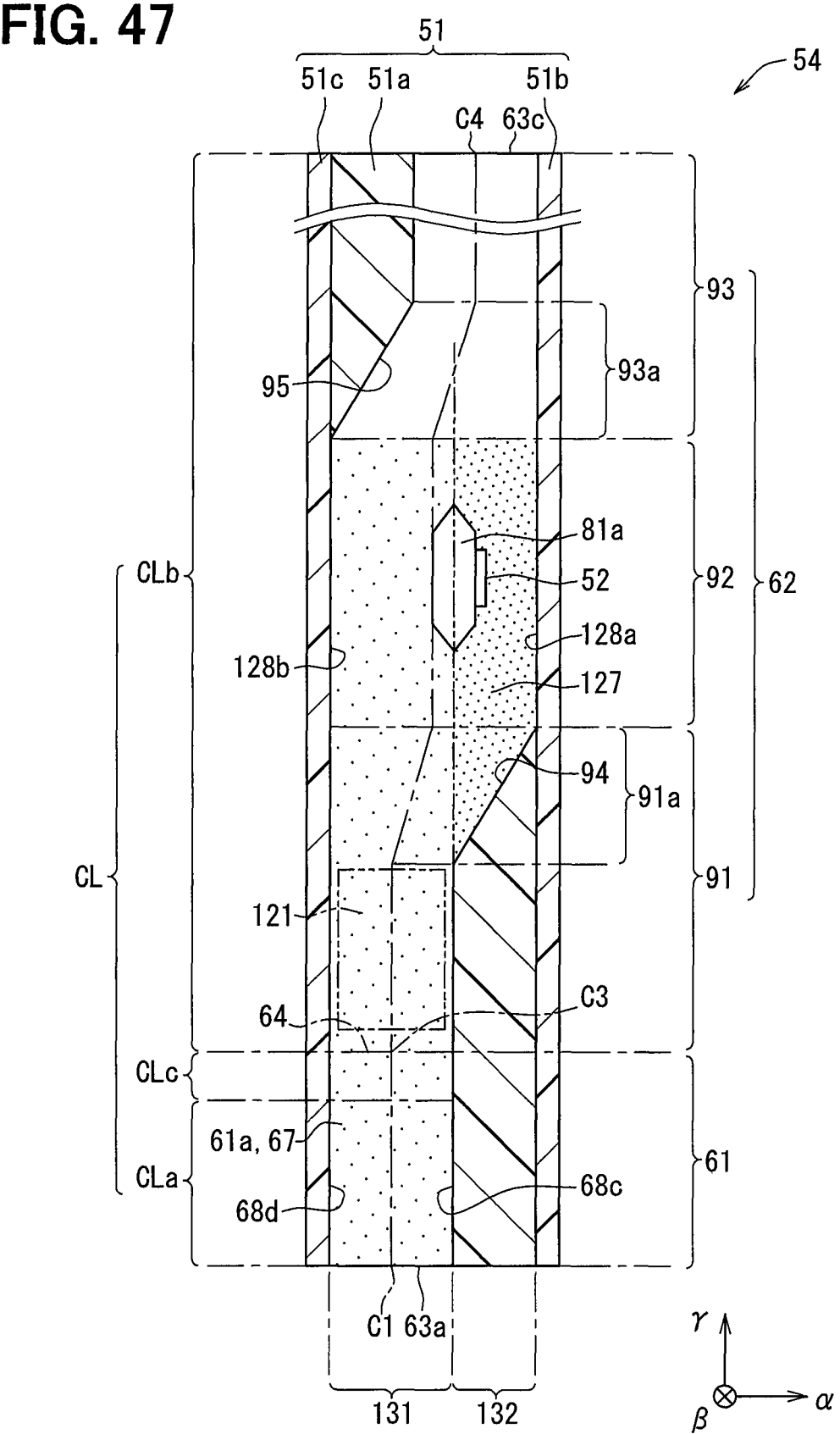
FIG. 47 is a diagram illustrating a positional relationship between the inflow region, the lateral region, and an guiding surface.

As a modification E3, the guiding surface 121 may be included in the inner peripheral surface 62a of the measurement flow channel 62. For example, as shown in FIGS. 46 and 47, the guiding surface 121 is included in the measurement bottom surface 127. In that configuration, the guiding surface 121 extends over the pair of measurement wall surfaces 128a and 128b in the lateral direction α. The guiding surface 121 extends from the flow channel boundary portion 64 to the width increasing surface 94 in the flow channel direction γ, and is formed almost entirely on the measurement bottom surface 127. In that configuration, as compared with the configuration in which the guiding surface 121 is included in the inflow ceiling surface portion 66a as in the fifth embodiment, the separation distance between the lateral region 132 and the guiding surface 121 in the flow channel direction γ is reduced. For that reason, it is assumed that the foreign matter whose traveling direction is inclined toward the back cover 51c side by the guiding surface 121 passes through the flow rate detection unit 52 at a timing earlier than when the traveling direction coincides with the flow channel direction γ. Even in that case, since the entry of the foreign matter into the lateral region 132 is unlikely to occur, the detection accuracy of the flow rate detection unit 52 can be inhibited from being lowered due to the adhesion of the foreign matter or the like.

Also, in the modification E3, the modifications E1 and E2 may be applied, and the guiding surface 121 may be included in the measurement bottom surface 127 and the measurement wall surfaces 128a and 128b in the measurement flow channel 62.

Figure 48:
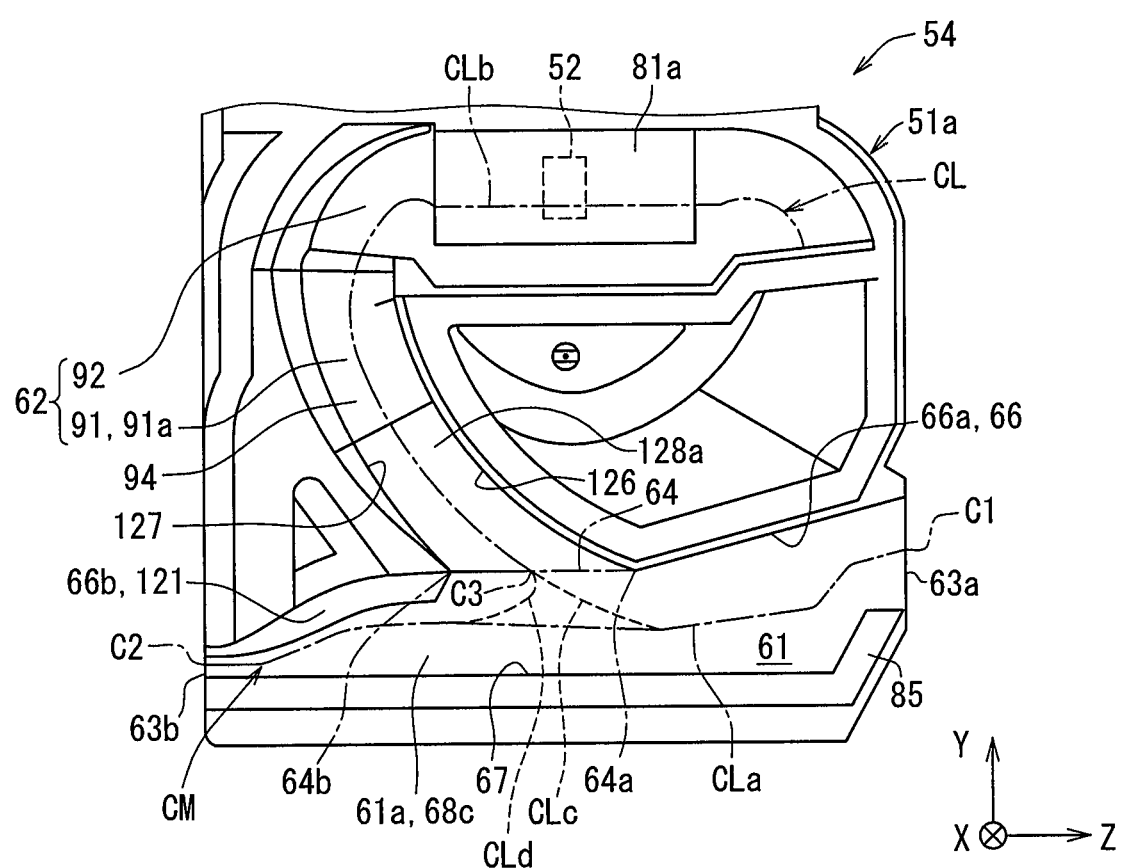
FIG. 48 is a diagram of the periphery of a passage flow channel in a modification E4.
Figure 49:
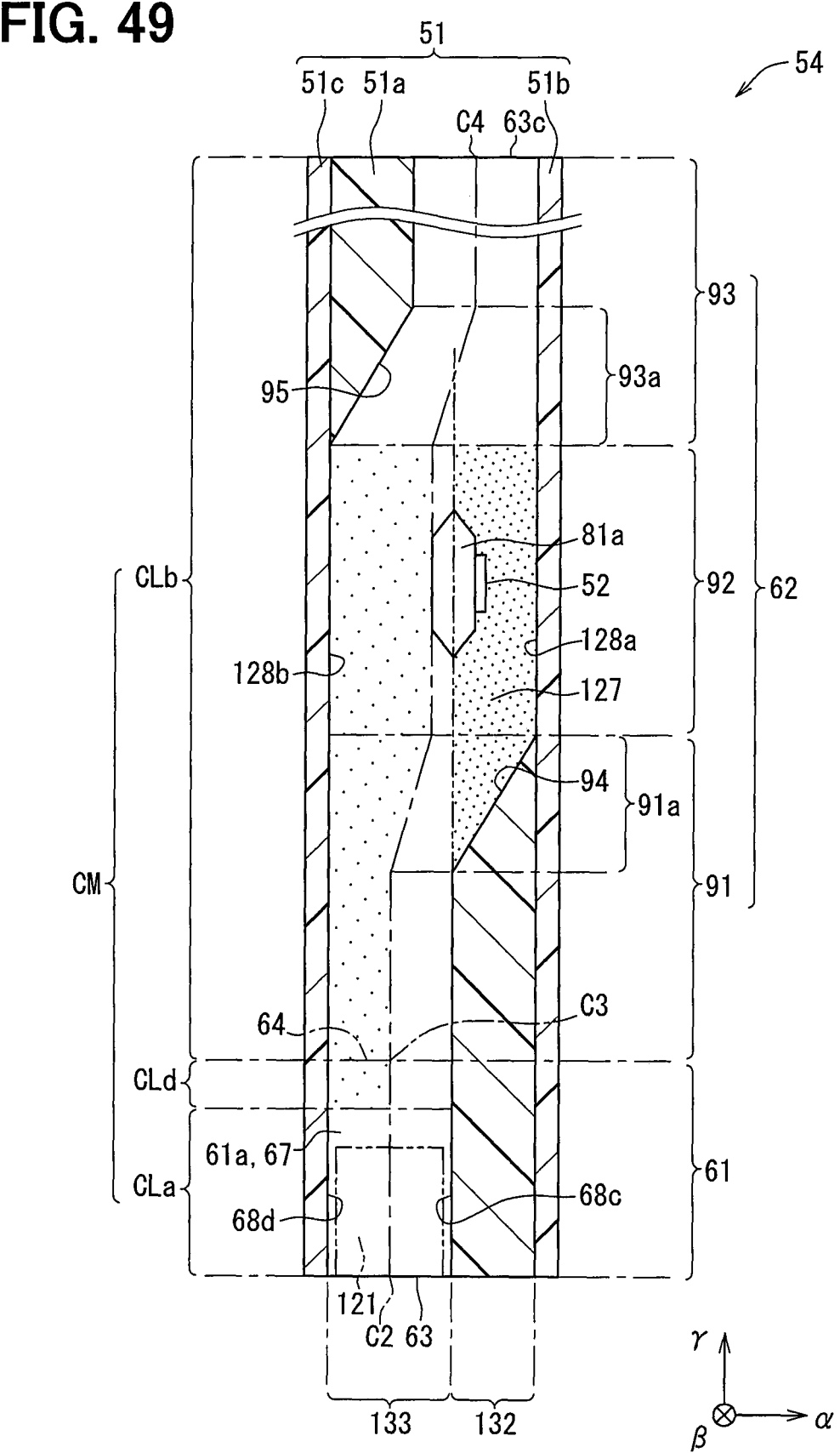
FIG. 49 is a diagram illustrating a positional relationship between the inflow region, the lateral region, and the guiding surface.

As a modification E4, the guiding surface 121 may be disposed on the downstream side of the flow channel boundary portion 64 in the passage flow channel 61. For example, as shown in FIGS. 48 and 49, the guiding surface 121 is included in the outflow ceiling surface portion 66b. Also in the above configuration, as in the fifth embodiment, the guiding surface 121 is extended over the pair of passage wall surfaces 68c and 68d. The guiding surface 121 extends from the flow channel boundary portion 64 to the outflow port 63b in the flow channel direction γ, and is formed almost entirely on the outflow ceiling surface portion 66b.

In the above modification E4, a virtual line connecting the center C2 of the outflow port 63b and the center C4 of the measurement outlet 63c is referred to as an outflow center line CM. The outflow center line CM includes a return center line CLd as a virtual line connecting the passage center line CLa and the measurement center line CLb. The return center line CLd is connected to the passage center line CLa by extending from the center C3 of the flow channel boundary portion 64 toward the downstream side in the passage flow channel 61.

In the above configuration, even if the foreign matter traveling through the passage flow channel 61 returns to the upstream side and enters the measurement flow channel 62 due to collision with the outflow ceiling surface portion 66b, the position of the foreign matter is easily changed to a position closer to the back cover 51c so as to move away from the lateral region 132. For that reason, the foreign matter that has returned from the outflow port 63b to the upstream side and has entered the measurement flow channel 62 is also less likely to pass through the position close to the lateral region 132 when reaching the intermediate measurement path 92, as in the fifth embodiment.

In the above modification E4, the above-described modifications E1 and E2 may be applied, and the guiding surface 121 may be included in the passage bottom surface 67 and the passage wall surfaces 68c and 68d on the downstream side of the flow channel boundary portion 64 in the passage flow channel 61.

Figure 50:
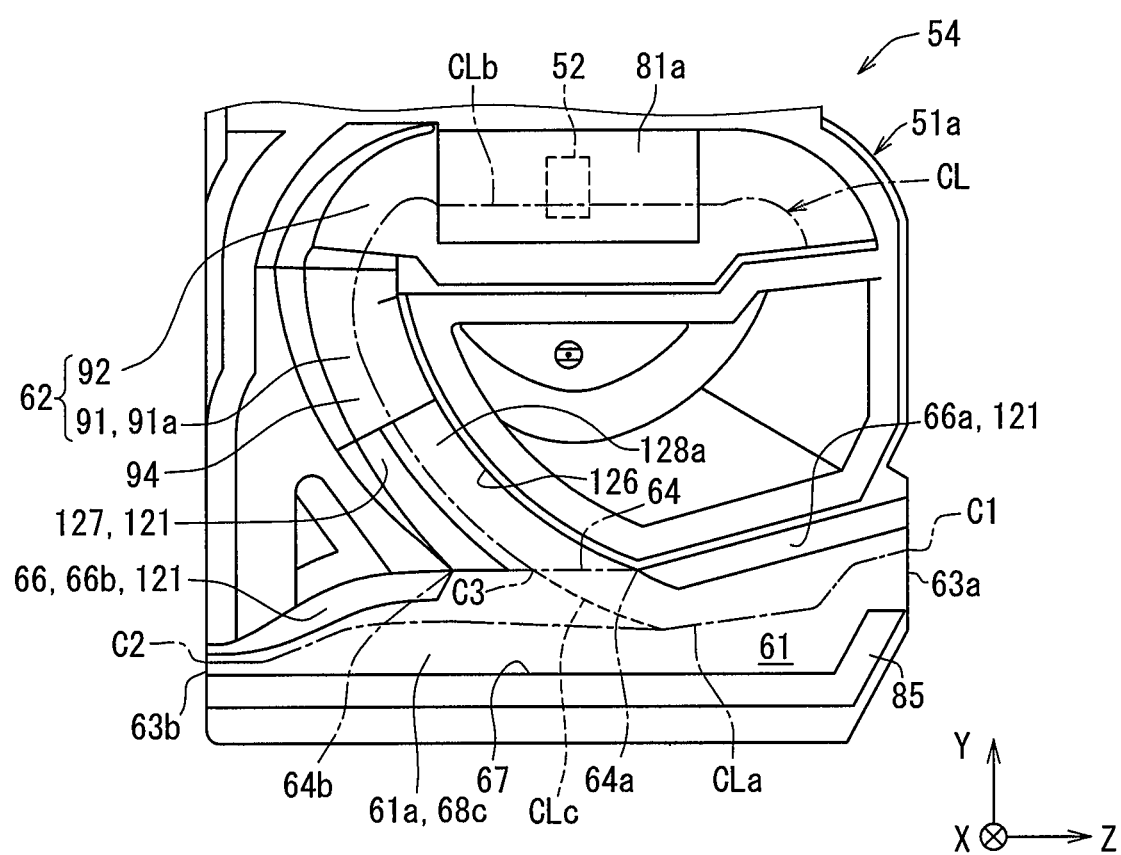
FIG. 50 is a diagram of the periphery of a passage flow channel in a modification E5.

As a modification E5, multiple guiding surfaces 121 may be provided. For example, as shown in FIG. 50, the guiding surface 121 is included in each of the inflow ceiling surface portion 66a, the outflow ceiling surface portion 66b, and the measurement bottom surface 127. In the above configuration, the foreign matter that has entered the measurement flow channel 62 from the upstream side in the passage flow channel 61 can be brought in closer to the back cover 51c by the two guiding surfaces 121. In addition, both of the foreign matter that has entered the measurement flow channel 62 by returning from the downstream side to the upstream side can be positioned toward the back cover 51c by the three guiding surfaces 121. This makes it possible to more reliably inhibit the foreign matter that has reached the intermediate measurement path 92 from entering the lateral region 132.

Figure 51:
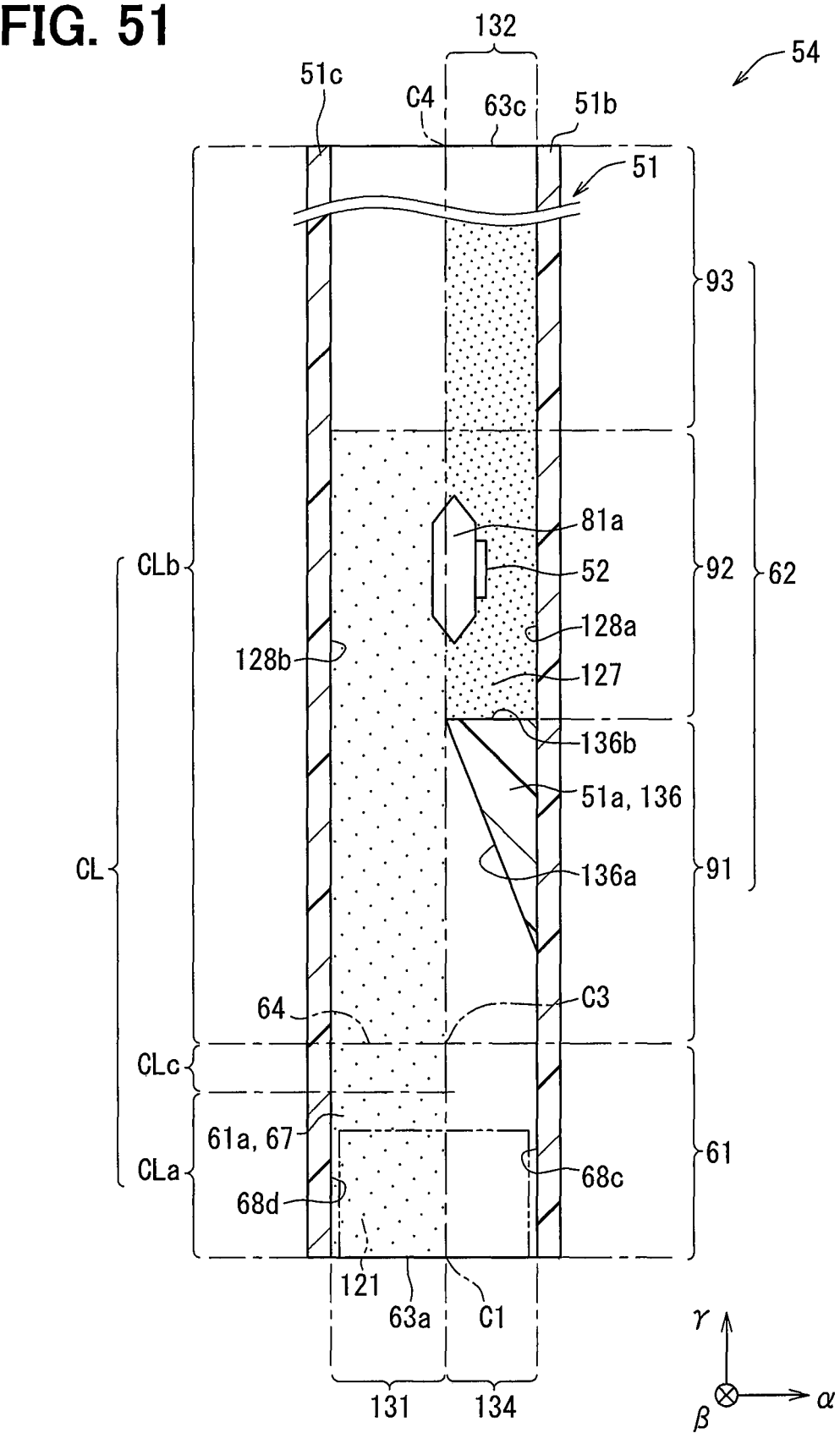
FIG. 51 is a diagram illustrating a cover portion in a modification E6.
Figure 52:
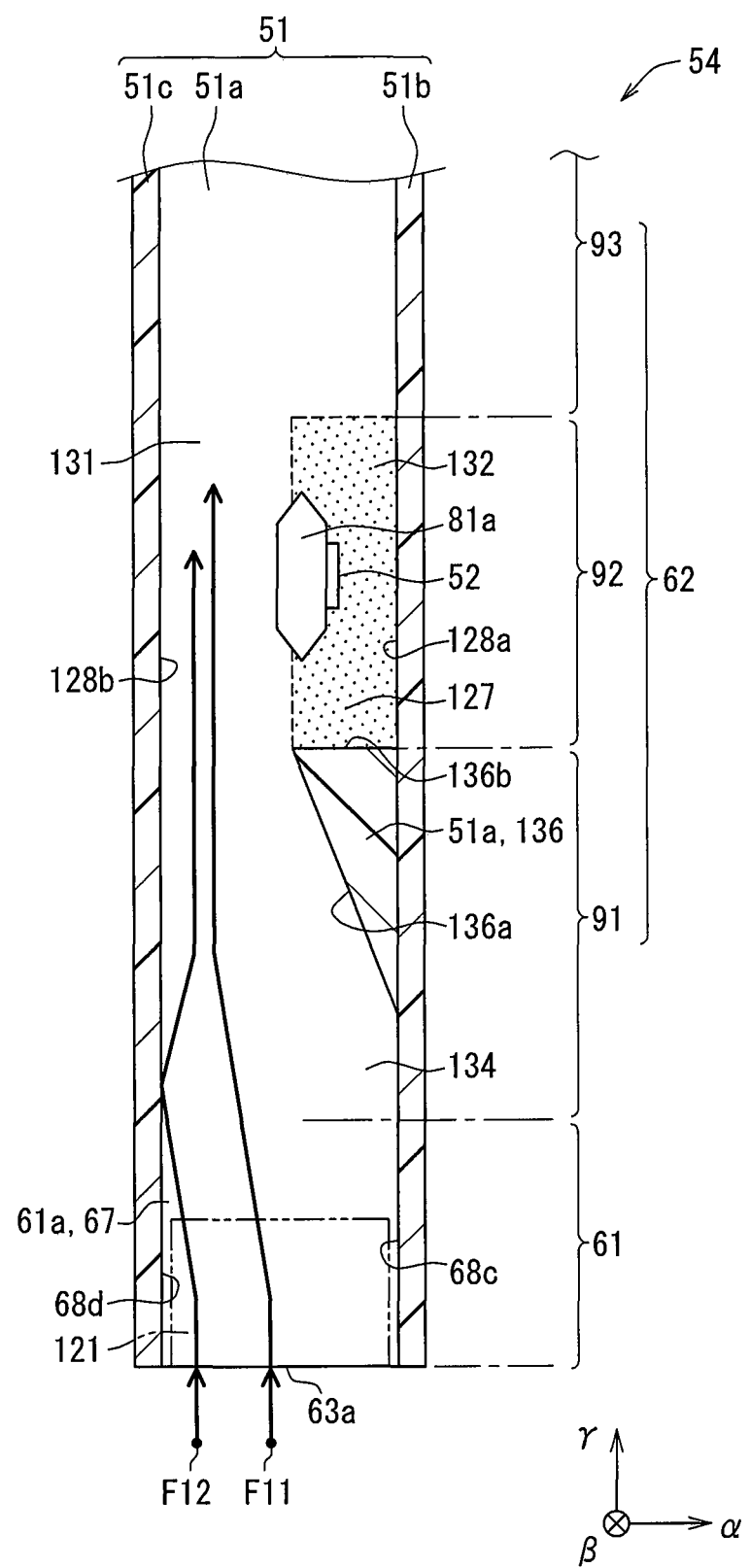
FIG. 52 is a diagram illustrating how a large foreign matter advances.

As a modification E6, a cover portion 136 may be provided to cover the flow rate detection unit 52 from the upstream side. For example, as shown in FIGS. 51 and 52, the cover portion 136 is provided in the measurement flow channel 62. In the above configuration, the cover portion 136 is disposed at a position spaced downstream from the inflow port 63a in the flow channel direction γ, and the cover portion 136 is disposed between the inflow port 63a and the lateral region 132. In that case, the lateral region 132 is hidden downstream of the cover portion 136 so that the inflow port 63a is not included in a region projected in the flow channel direction γ. In the passage flow channel 61 and the measurement flow channel 62, a region formed closer to the inflow port 63a than the cover portion 136 is referred to as a near-side region 134. The near-side region 134 is disposed laterally with the lateral region 132 in the lateral direction α in the inflow region 131.

The cover portion 136 has a cover surface 136a and an orthogonal surface 136b. The cover surface 136a has a function of guiding the foreign matter advancing toward the downstream side to the back cover 51c, and faces the back cover 51c side. The cover surface 136a is an inclined surface that moves away from the back cover 51c as the cover surface 136a comes closer to the inflow port 63a, and is inclined so as to face the inflow port 63a side with respect to the flow channel direction γ. In the lateral direction α, a width dimension of the cover portion 136 gradually decreases as the cover portion 136 approaches the inflow port 63a. The cover portion 136 is included in the housing main body 51a, and the cover surface 136a is included in the front measurement wall surface 128a. The inclination angle of the cover surface 136a with respect to the front cover 51b is, for example, several degrees to several tens of degrees smaller than 45 degrees.

The orthogonal surface 136b is orthogonal to the flow channel direction γ and faces the measurement outlet 63c in the flow channel direction γ. In the flow channel direction γ, the flow rate detection unit 52 is disposed between the orthogonal surface 136b and the measurement outlet 63c. The orthogonal surface 136b extends parallel to the lateral direction α, but may be inclined with respect to the lateral direction α.

In the above configuration as well, as in the fifth embodiment, when the large foreign matter F11 and F12 traveling linearly in the flow channel direction γ collides with the guiding surface 121, as shown in FIG. 52, both the large foreign matter F11 and F12 travel in a direction inclined with respect to the flow channel direction γ toward the back cover 51c. For that reason, even when the large foreign matter F11 and F12 reach the intermediate measurement path 92 and is closest to the measurement board portion 81a, the large foreign matter F11 and F12 passes through a position in the lateral direction α, which is relatively distant from the lateral region 132, from the measurement board portion 81a. Even if the foreign matter such as the large foreign matter F11 advances in the near-side region 134 instead of the inflow region 131, the foreign matter is guided to the back cover 51c side by colliding with the cover surface 136a. In other words, the foreign matter is guided to a position away from the lateral region 132 in the lateral direction α. This makes it possible to inhibit the foreign matter advancing in the inflow region 131 and the foreign matter advancing in the near-side region 134 from entering the lateral region 132.

Figure 53:
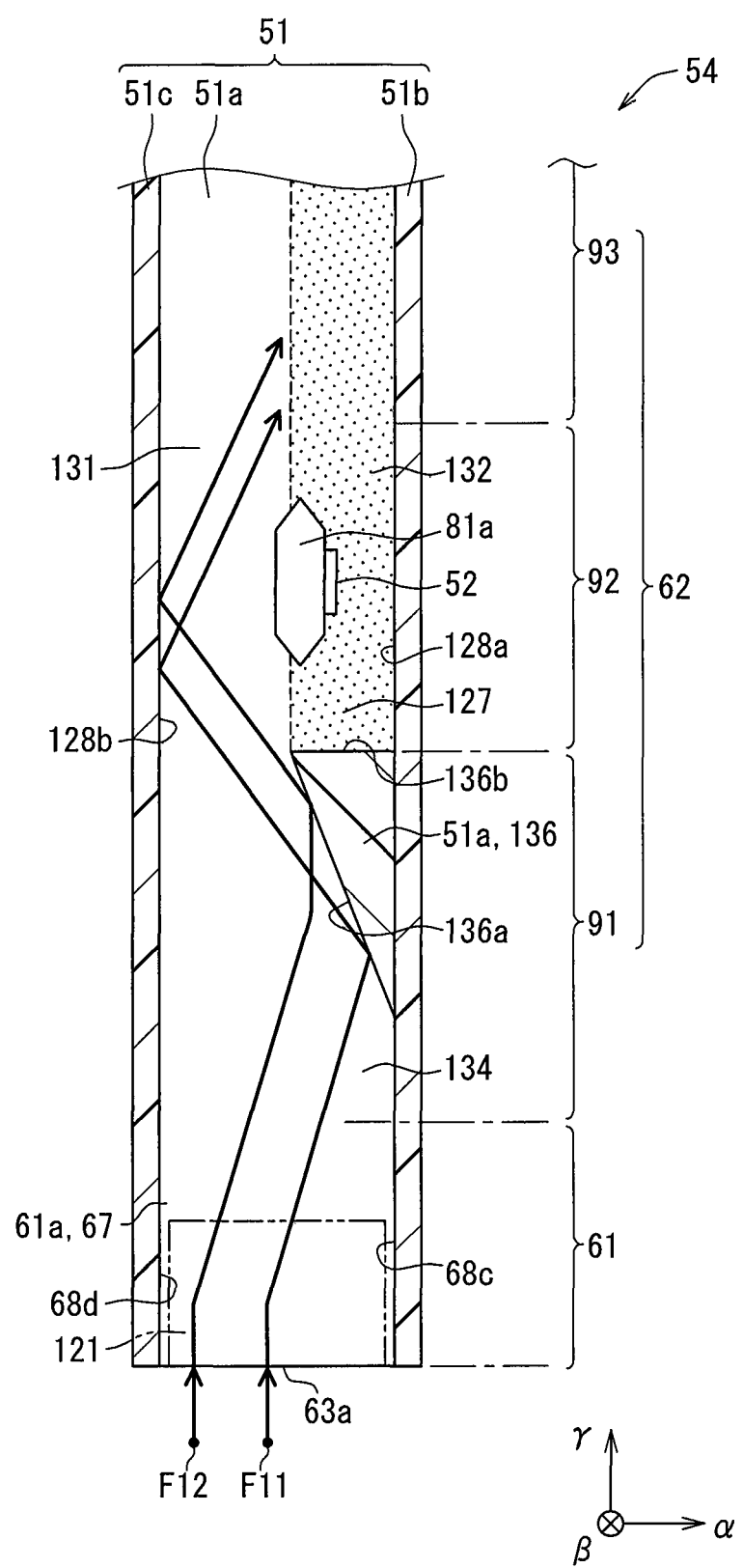
FIG. 53 is a diagram illustrating how a large foreign matter advances in a modification E7.

As a modification E7, the guiding surface 121 may not bring the foreign matter closer to the inflow region 131 in the lateral direction α, but may bring the foreign matter closer to the lateral region 132. In other words, the guiding surface 121 may face the front cover 51b instead of the back cover 51c. In the above configuration, as shown in FIG. 53, when the large foreign matter F11 and F12 traveling linearly in the flow channel direction γ collides with the guiding surface 121, the large foreign matter F11 and F12 travels in a direction inclined with respect to the flow channel direction γ toward the front cover 51b, which is opposite to the fifth embodiment. In that case, the large foreign matter F11 and F12 reaches the cover surface 136a by traveling through the near-side region 134 instead of the inflow region 131, and is likely to be guided to the back cover 51c side by colliding with the cover surface 136a. For that reason, the large foreign matter F11 and F12 passes through a position relatively far from the lateral region 132, and therefore, the large foreign matter F11 and F12 can be inhibited from entering the lateral region 132.

As a modification F8, the flow rate detection unit 52 may not be separated from the width increasing surface 94 toward the measurement outlet 63c in the flow channel direction γ, but at least a part of the flow rate detection unit 52 may be aligned with the width increasing surface 94 in the lateral direction α. In that case, since the flow rate detection unit 52 can be disposed in the immediate vicinity of the width increasing surface 94, the foreign matter can be more surely inhibited from entering the lateral region 132 at a position before passing through the flow rate detection unit 52 in the inflow region 131.

Sixth Embodiment

An air flow meter 50 according to a sixth embodiment has inflow step surfaces 71a of the second embodiment, a parallel region 101 and a height narrowing surface 105 of the third embodiment, a configuration in which a partition top portion 111a of the fourth embodiment is not exposed from an inflow port 63a, and a lateral region 132 of the fifth embodiment. In the present embodiment, differences from the fifth embodiment will be mainly described.

Figure 54:
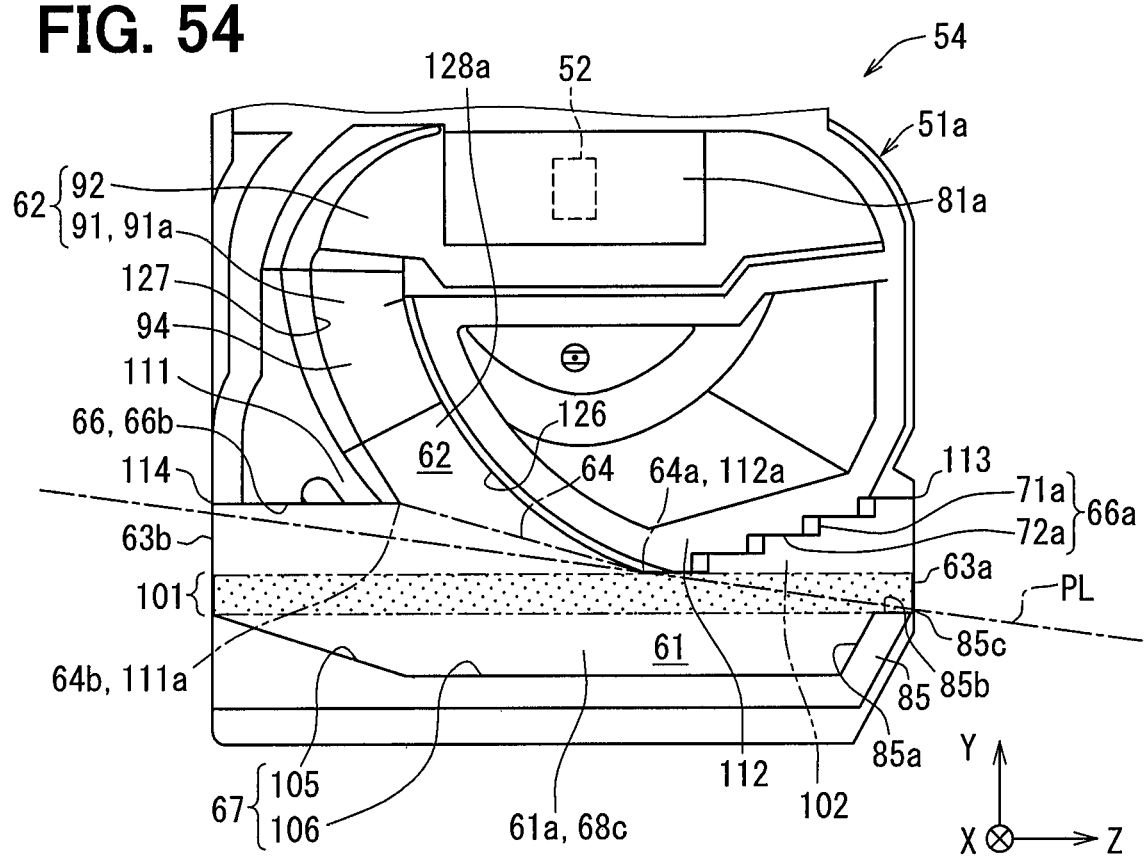
FIG. 54 is a diagram of the periphery of a passage flow channel in a sixth embodiment.
Figure 55:
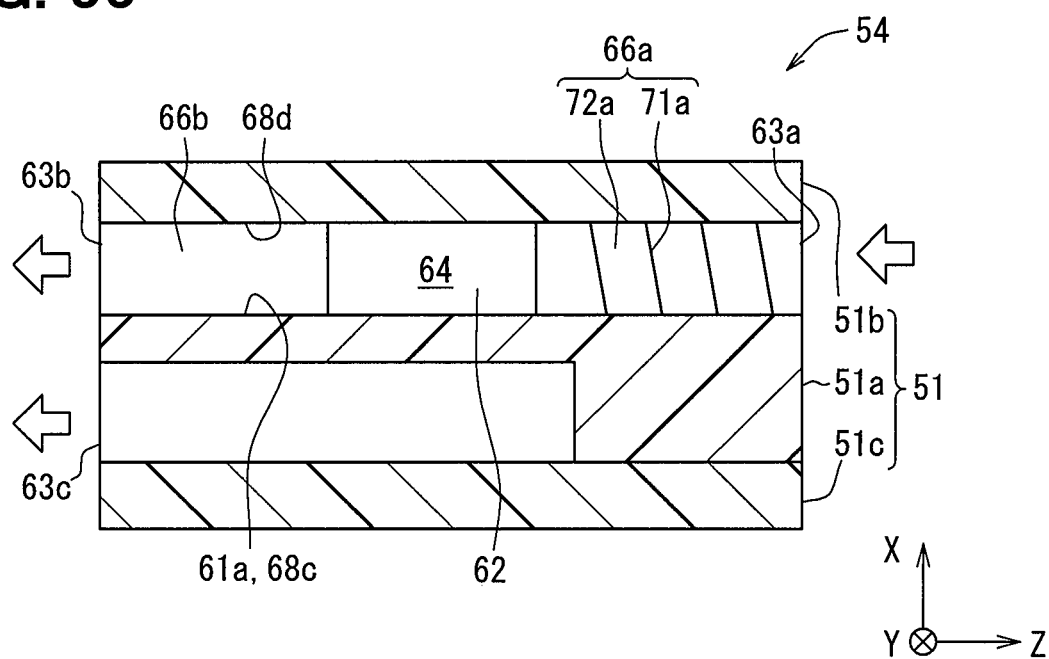
FIG. 55 is a cross-sectional view of the passage flow channel as viewed from a bottom side toward a ceiling side in a direction orthogonal to the height direction.

As shown in FIGS. 54 and 55, in the present embodiment, unlike the second embodiment, all the inflow step surfaces 71a are not orthogonal to the depth direction Z, but are inclined with respect to the depth direction Z. In that case, the inflow step surfaces 71a are inclined with respect to the width direction X, but are not inclined with respect to the height direction Y, and extend parallel to the height direction Y. The inflow step surfaces 71a are inclined so that an end portion on a front passage wall surface 68c side is disposed at a position closer to the inflow port 63a than an end portion on a back passage wall surface 68d side, and the inflow step surfaces 71a are inclined surfaces facing the inflow port 63a and the back passage wall surface 68d. The inclination angle of the inflow step surface 71a with respect to the width direction X is set to, for example, several degrees to several tens of degrees smaller than 45 degrees.

Figure 56:
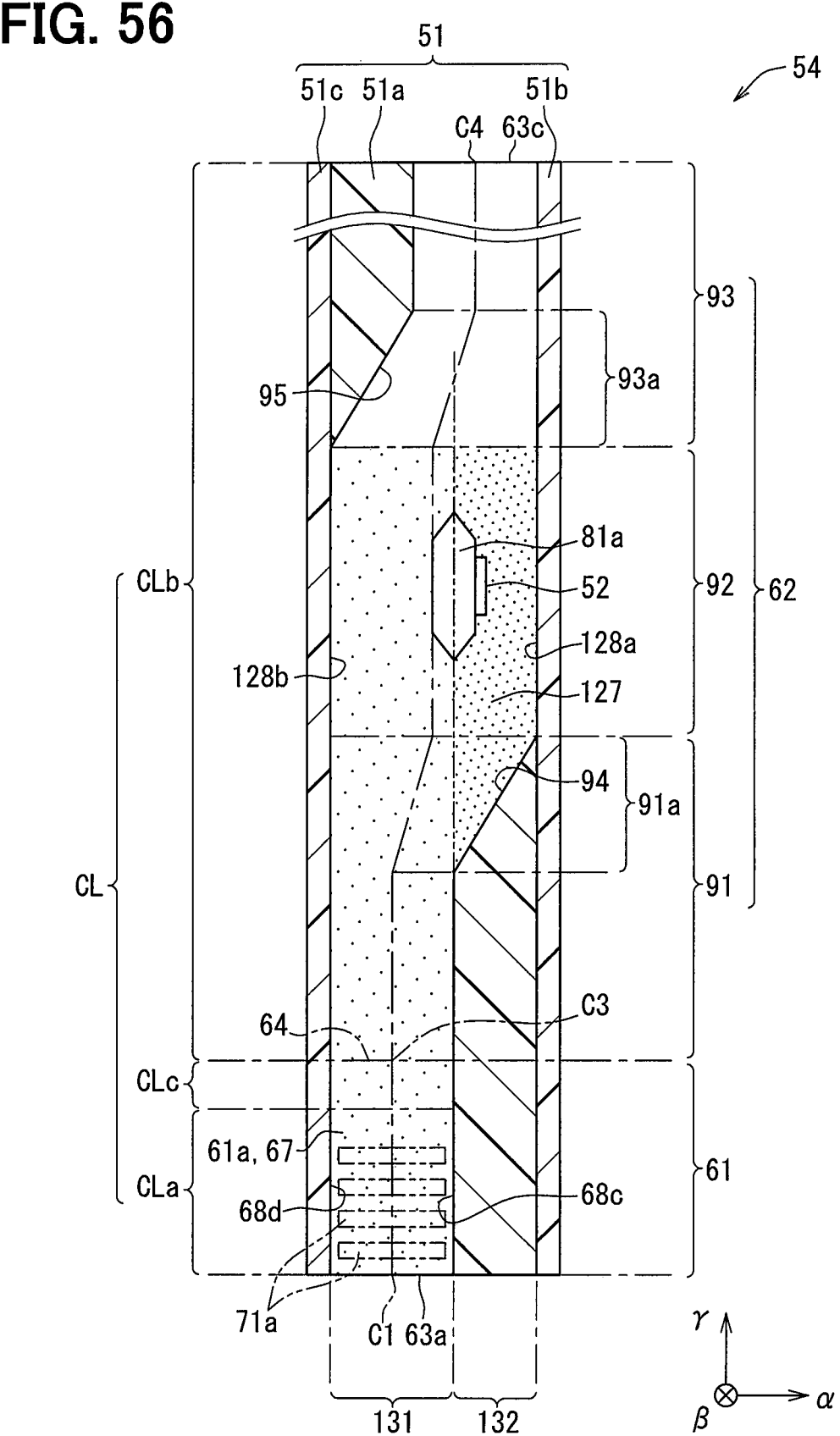
FIG. 56 is a diagram illustrating the inflow region and the lateral region.

The inflow step surfaces 71a have a function as an guiding surface 121 of the fifth embodiment. For example, when a large foreign matter that travels linearly in the depth direction Z collides with the inflow step surfaces 71a and rebounds, the large foreign matter does not travel parallel to the depth direction Z toward the inflow port 63a, but travels toward the back passage wall surface 68d. In that case, for example, even if the large foreign matter rebounded at the inflow step surfaces 71a advances in the passage flow channel 61 again toward the downstream side by the flow of the intake air, the large foreign matter advances to a position closer to the back passage wall surface 68d. As described above, the inflow step surface 71a corresponds to an guiding surface, and as shown in FIG. 56, the provision of the multiple inflow step surfaces 71a in an inflow ceiling surface portion 66a corresponds to the provision of the multiple guiding surfaces.

Like the large foreign matter F11 and F12 of the fifth embodiment, the large foreign matter traveling in the flow channel direction γ at the position close to the back passage wall surface 68d passes through a position relatively distant from the flow rate detection unit 52 in the lateral direction α even if the large foreign matter reaches an intermediate measurement path 92. For that reason, even if the traveling direction of the large foreign matter slightly changes in the direction facing the front cover 51b, the large foreign matter is unlikely to enter from the inflow region 131 into the lateral region 132.

In the present embodiment, the inflow ceiling surface portion 66a partitioning the ceiling-side region 102 has an inflow step surface 71a. In that case, the foreign matter that has entered the ceiling-side region 102 from the inflow port 63a is rebounded to the inflow port 63a side at the inflow ceiling surface portion 66a, thereby inhibiting the passage of the foreign matter to the downstream side of the ceiling-side region 102 in the passage flow channel 61. In addition, the foreign matter that has entered the parallel region 101 from the inflow port 63a advances linearly in the depth direction Z as it is, so that the foreign matter easily comes out from the outflow port 63b to the outside. Further, even with respect to the foreign matter that travels linearly in the direction inclined with respect to the depth direction Z, the partition top portion 111a is not exposed to the upstream side from the inflow port 63a, which makes it difficult to directly enter the measurement flow channel 62 in the state of maintaining the linearly traveling. Even if there is a foreign matter that has entered the measurement flow channel 62, the foreign matter is likely to come closer to a position closer to the back cover 51c by colliding with the inflow step surfaces 71a that function as the guiding surface. For that reason, the foreign matter reaching the intermediate measurement path 92 is inhibited from entering the lateral region 132.

The sixth embodiment can be applied to various embodiments and combinations without departing from the scope of the present disclosure.

As a modification F1, the function as the guiding surface may be imparted to an inflow connection surface 72a. For example, like the guiding surface 121 of the fifth embodiment, the inflow connection surface 72a may not be orthogonal to the height direction Y, but may be an inclined surface facing the passage bottom surface 67 side and the back cover 51c side. In addition, the function as the guiding surface may be imparted to the outflow step surfaces 71b or the outflow connection surface 72b.

As a modification F2, not all of the inflow step surfaces 71a may be provided with a function as the guiding surface, but at least one of the inflow step surfaces 71a may be provided with a function as the guiding surface. For example, the inflow step surface 71a disposed at the most downstream side of the multiple inflow step surfaces 71a is inclined with respect to the depth direction Z, thereby serving as the guiding surface. In the above configuration, the other inflow step surfaces 71a are orthogonal to the depth direction Z and do not have the function as the guiding surface.

A modification F3 may have at least two configurations among the inflow step surfaces 71a of the second embodiment, the parallel region 101 and the height narrowing surface 105 of the third embodiment, the configuration in which the partition top portion 111a is not exposed from the inflow port 63a in the fourth embodiment, and the lateral region 132 of the fifth embodiment. Even in the above case, a deterrent force against the foreign matter reaching the flow rate detection unit 52 can be exerted.

Although the multiple embodiments according to the present disclosure have been described above, the present disclosure is not construed as being limited to the above-mentioned embodiments, and can be applied to various embodiments and combinations within a range not departing from the spirit of the present disclosure.

As a modification example G1, in each of the embodiments described above, the flow rate detection unit is provided in the measurement flow channel as the physical quantity detector, but the physical quantity detector provided in the measurement flow channel may be a humidity detection unit, a temperature detection unit, or a pressure detection unit.

As a modification G2, in each of the above-mentioned embodiments, the measurement flow channel has a circulating shape, but the measurement flow channel may have a shape extending in the depth direction Z without circulating.

Although the present disclosure has been described in accordance with the examples, it is understood that the disclosure is not limited to such examples or structures. The present disclosure encompasses various modifications and variations within the scope of equivalents. In addition, various combinations and configurations, as well as other combinations and configurations that include only one element, more, or less, are within the extent and spirit of the present disclosure.

The invention claimed is:

1. A physical quantity measurement device that measures a physical quantity of a fluid, comprising:
   a passage flow channel that has an inflow port and an outflow port, the fluid entering the passage flow channel through the inflow port and exiting the passage flow channel through the outflow port;
   a branch flow channel that branches off from the passage flow channel, the branch flow channel discharging the fluid having flowed into the branch flow channel from the passage flow channel through a branch outflow port; and
   a physical quantity detector that detects a physical quantity of the fluid in the branch flow channel, wherein
   an imaginary line connecting a center of the inflow port and a center of the branch outflow port and including at least a part of a center line of the passage flow channel and a center line of the branch flow channel is defined as a flow channel center line,
   a boundary between the passage flow channel and the branch flow channel is defined as a flow channel boundary portion,
   a pair of opposing passage surfaces in an inner peripheral surface of the passage flow channel face each other across the flow channel boundary portion and the inflow port,
   a direction along which the pair of opposing passage surfaces are arranged is defined as a lateral direction,
   a direction along which the flow channel center line extends is defined as a flow channel direction,
   a direction orthogonal to both the lateral direction and the flow channel direction is defined as a vertical direction,
   an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, and a guiding surface that guides away from the lateral region in the lateral direction foreign matter entering through the inflow port together with the fluid is included in at least one of the inner peripheral surface of the passage flow channel and an inner peripheral surface of the branch flow channel at a position upstream of the lateral region.

2. The physical quantity measurement device according to claim 1, wherein the guiding surface extends over the pair of opposing passage surfaces.

3. The physical quantity measurement device according to claim 1, wherein the guiding surface is disposed in the inflow region in the passage flow channel.

4. The physical quantity measurement device according to claim 1, wherein the guiding surface is disposed in the inflow region in the branch flow channel.

5. The physical quantity measurement device according to claim 1, wherein the inflow region is included in both the passage flow channel and the branch flow channel by extending across the flow channel boundary portion in the flow channel direction, and the lateral region is disposed at a position downstream of the flow channel boundary portion to be included only in the branch flow channel.

6. The physical quantity measurement device according to claim 1, wherein the inner peripheral surface of the branch flow channel has a pair of opposing branch surfaces facing each other in the lateral direction, one of the pair of opposing branch surfaces includes a width increasing surface that is gradually away from the other of the pair of opposing branch surfaces as approaching the physical quantity detector in the flow channel direction so that a lateral dimension of the branch flow channel in the lateral direction is increased, and the lateral region is at a position downstream of the width increasing surface in the flow channel direction.

7. The physical quantity measurement device according to claim 1, further comprising a cover portion that covers the physical quantity detector from an upstream side of the detector in the branch flow channel, wherein the lateral region is at a position downstream of the cover portion in the flow channel direction.

8. The physical quantity measurement device according to claim 1, wherein the branch flow channel includes:
an upstream branch pass extending downstream from the flow channel boundary portion;
a downstream branch pass at least a part of which is at a position overlapping the upstream branch pass in the lateral direction, the downstream branch pass extending upstream from the branch flow channel; and
an intermediate branch pass disposed between the upstream branch pass and the downstream branch pass in the flow channel direction, the intermediate branch pass connecting the upstream branch pass and the downstream branch pass,
a partition wall portion that partitions the upstream branch pass and the downstream branch pass is disposed between the upstream branch pass and the downstream branch pass in the lateral direction, and
the lateral region is included in the intermediate branch pass.

9. A physical quantity measurement device that measures a physical quantity of fluid, comprising:

a passage flow channel that has an inflow port and an outflow port, the fluid entering the passage flow channel through the inflow port and exiting the passage flow channel through the outflow port;

a branch flow channel that branches off from the passage flow channel, the branch flow channel discharging the fluid having flowed in the branch flow channel from the passage flow channel through a branch outflow port; and a physical quantity detector that detects a physical quantity of the fluid in the branch flow channel, wherein an imaginary line connecting a center of the inflow port and a center of the branch outflow port and including at least a part of a center line of the passage flow channel and a center line of the branch flow channel is defined as a flow channel center line, a boundary between the passage flow channel and the branch flow channel is defined as a flow channel boundary portion, a pair of opposing surfaces in an inner peripheral surface of the passage flow channel face each other across the flow channel boundary portion and the inflow port, a direction along which the pair of opposing surfaces are arranged is defined as a lateral direction, a direction along which the flow channel center line extends is defined as a flow channel direction, and a direction orthogonal to both the lateral direction and the flow channel direction is defined as a vertical direction, an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, a cover portion that covers the physical quantity detector from an upstream side of the detector is disposed in the branch flow channel, the lateral region is disposed at a position downstream of the cover portion in the flow channel direction, and a guiding surface that guides toward the cover portion in the lateral direction foreign matter entering through the inflow port together with the fluid is included in at least one of the inner peripheral surface of the passage flow channel and an inner peripheral surface of the branch flow channel at a position upstream of the lateral region.

10. A physical quantity measurement device that measures a physical quantity of fluid, comprising:

a passage flow channel that has an inflow port and an outflow port, the fluid entering the passage flow channel through the inflow port and exiting the passage flow channel through the outflow port;

a branch flow channel that branches off from the passage flow channel, the branch flow channel discharging the fluid having flowed in the branch flow channel through a branch outflow port; and a physical quantity detector that detects a physical quantity of the fluid in the branch flow channel, wherein an imaginary line connecting a center of the inflow port and a center of the branch outflow port and including at least a part of a center line of the passage flow channel and a center line of the branch flow channel is defined as a flow channel center line, and a boundary between the passage flow channel and the branch flow channel is a flow channel boundary portion, a pair of opposing surfaces in an inner peripheral surface of the passage flow channel face each other across the flow channel boundary portion and the inflow port, a direction along which the pair of opposing surfaces are arranged is defined as a lateral direction, a direction along which the flow channel center line extends is defined as a flow channel direction, a direction orthogonal to both the lateral direction and the flow channel direction is defined as a vertical direction, an inflow region extending from the inflow port along the flow channel center line in the flow channel direction and a lateral region laterally arranged with respect to the inflow region in the lateral direction without extending from the inflow port are included in at least one of the passage flow channel and the branch flow channel, the physical quantity detector is disposed in the lateral region in the branch flow channel, and a guiding surface that guides away from the lateral region in the lateral direction foreign matter entering through the inflow port together with the fluid is included in the inner peripheral surface of the passage flow channel at a position upstream of the flow channel boundary portion in the passage flow channel.

* * * * *